(12) United States Patent
Aoyama

(10) Patent No.: US 11,926,756 B2
(45) Date of Patent: Mar. 12, 2024

(54) FLUORINE-CONTAINING ETHER COMPOUND, FLUORINE-CONTAINING ETHER COMPOSITION, COATING LIQUID, ARTICLE, METHOD FOR PRODUCING ARTICLE, AND METHOD FOR PRODUCING FLUORINE-CONTAINING COMPOUND

(71) Applicant: AGC Inc., Tokyo (JP)

(72) Inventor: Motoshi Aoyama, Tokyo (JP)

(73) Assignee: AGC Inc., Tokyo (JP)

( * ) Notice: Subject to any disclaimer, the term of this patent is extended or adjusted under 35 U.S.C. 154(b) by 289 days.

(21) Appl. No.: 17/305,605

(22) Filed: Jul. 12, 2021

(65) Prior Publication Data

US 2021/0355345 A1 Nov. 18, 2021

Related U.S. Application Data

(63) Continuation of application No. PCT/JP2020/003794, filed on Jan. 31, 2020.

(30) Foreign Application Priority Data

Feb. 8, 2019 (JP) .................................. 2019-022079
Dec. 6, 2019 (JP) .................................. 2019-220995

(51) Int. Cl.
| | | |
|---|---|---|
| C09D 171/00 | (2006.01) | |
| C07F 7/18 | (2006.01) | |
| C08G 65/336 | (2006.01) | |
| C09D 5/00 | (2006.01) | |

(52) U.S. Cl.
CPC .......... *C09D 171/00* (2013.01); *C07F 7/1804* (2013.01); *C08G 65/336* (2013.01); *C09D 5/00* (2013.01)

(58) Field of Classification Search
None
See application file for complete search history.

(56) References Cited

U.S. PATENT DOCUMENTS

| | | | |
|---|---|---|---|
| 3,303,145 A * | 2/1967 | Carlson | C08G 65/226 568/381 |
| 4,889,656 A | 12/1989 | Flynn et al. | |
| 5,021,602 A | 6/1991 | Clement et al. | |
| 5,037,917 A | 8/1991 | Babb et al. | |
| 2007/0114883 A1* | 5/2007 | Chen | B81C 1/0096 310/311 |
| 2016/0221316 A1* | 8/2016 | Yairi | B32B 25/08 |
| 2018/0148606 A1 | 5/2018 | Hoshino et al. | |
| 2019/0040266 A1 | 2/2019 | Hoshino et al. | |

FOREIGN PATENT DOCUMENTS

| | | |
|---|---|---|
| EP | 0 314 380 A1 | 5/1989 |
| JP | 57-059822 A | 4/1982 |
| JP | 01-157932 A | 6/1989 |
| JP | 04-500364 A | 1/1992 |
| JP | 04-500388 A | 1/1992 |
| JP | 2016-037541 A | 3/2016 |
| WO | WO 90/15082 A1 | 12/1990 |
| WO | WO 2017/038830 A1 | 3/2017 |
| WO | WO 2017/187775 A1 | 11/2017 |
| WO | WO 2019/243403 A1 | 12/2019 |
| WO | WO 2019/243404 A1 | 12/2019 |

OTHER PUBLICATIONS

International Search Report dated Arp. 7, 2020 in PCT/JP2020/003794 filed on Jan. 31, 2020, 3 pages.

* cited by examiner

*Primary Examiner* — Ramsey Zacharia
(74) *Attorney, Agent, or Firm* — Oblon, McClelland, Maier & Neustadt, L.L.P.

(57) ABSTRACT

To provide a fluorinated ether compound, a fluorinated ether composition and a coating liquid excellent in chemical resistance, an article having a surface layer excellent in chemical resistance and a method for producing it, and a method for producing a fluorinated ether compound excellent in chemical resistance.

A fluorinated ether compound which has a first partial structure represented by the following formula (1) and a second partial structure represented by the following formula (2), and
 which has at least five first partial structures, or has at least two second partial structures:

$$—OR^{f12}— \quad (1)$$

$$—OR^{f13}— \quad (2)$$

wherein $R^{f12}$ is a $C_{1-6}$ fluoroalkylene group, and
 $R^{f13}$ is a group having a fluorinated cyclic structure which may have a hetero atom.

33 Claims, No Drawings

FLUORINE-CONTAINING ETHER COMPOUND, FLUORINE-CONTAINING ETHER COMPOSITION, COATING LIQUID, ARTICLE, METHOD FOR PRODUCING ARTICLE, AND METHOD FOR PRODUCING FLUORINE-CONTAINING COMPOUND

TECHNICAL FIELD

The present invention relates to a fluorinated ether compound, a fluorinated ether composition, a coating liquid, an article, a method for producing an article, and a method for producing a fluorinated compound.

BACKGROUND ART

A fluorinated ether compound having a fluorine atom is excellent in various properties such as low refractive index, low dielectric constant, water/oil repellency, heat resistance, chemical resistance, chemical stability and transparency, and is utilized in a wide range of fields including electrical and electric materials, semiconductor materials, optical materials and surface treatment agents.

For example, a fluorinated ether compound having a perfluoropolyether chain and a hydrolyzable silyl group is capable of forming on a surface of a substrate a surface layer having high lubricity, water/oil repellency, etc., and is thereby suitably used for a surface treatment agent. A surface treatment agent containing the fluorinated ether compound is used in an application where it is desired to maintain, for a long period of time, a performance (abrasion resistance) whereby water/oil repellency is less likely to be lowered even if the surface layer is rubbed repeatedly with fingers, and a performance (fingerprint stain removability) whereby a fingerprint adhering to the surface layer can be readily removed by wiping, for example, as a surface treatment agent for a member constituting a plane of a touch panel to be touched with fingers, a spectacle lens, a display of a wearable terminal, etc.

As a fluorinated ether compound capable of forming on a surface of a substrate a surface layer excellent in abrasion resistance and fingerprint stain removability, a fluorinated ether compound having a perfluoropolyether chain and a hydrolyzable silyl group has been proposed (Patent Documents 1 and 2).

PRIOR ART DOCUMENTS

Patent Documents

Patent Document 1: JP-A-2016-037541
Patent Document 2: WO2017/038830

DISCLOSURE OF INVENTION

Technical Problem

As described above, a fluorinated ether compound is useful as a surface treatment agent to impart the above-described various properties, and demands for fluorinated ether compounds which can be used in various environments are increasing. Accordingly, fluorinated ether compounds more excellent in chemical resistance have been required.

The object of the present invention is to provide a fluorinated ether compound excellent in chemical resistance, a fluorinated ether composition and a coating liquid capable of forming a surface layer excellent in chemical resistance, an article having a surface layer excellent in chemical resistance and its production method, and a method for producing a fluorinated compound useful as a raw material of the fluorinated ether compound.

Solution to Problem

The present invention provides a fluorinated ether compound, a fluorinated ether composition, a coating liquid, an article, its production method, and a method for producing a fluorinated compound, having the following constructions [1] to [25],

[1] A fluorinated ether compound which has a first partial structure represented by the following formula (1) and a second partial structure represented by the following formula (2), and
which has at least five first partial structures, or has at least two second partial structures:

$$—OR^{f12}— \quad (1)$$

$$—OR^{f13}— \quad (2)$$

wherein $R^{f12}$ is a $C_{1-6}$ fluoroalkylene group, and
$R^{f13}$ is a group having a fluorinated cyclic structure which may have a hetero atom.

[2] The fluorinated ether compound according to [1], which is a compound represented by the following formula (1A):

$$[R^{f}—]_{a1}Q^{1}[-T]_{b1} \quad (1A)$$

wherein $R^{f}$ is a monovalent group the bond terminal of which is constituted by a carbon atom, which has the first partial structure and the second partial structure, and which has at least five first partial structures or has at least two second partial structures, and when there are two or more $R^{f}$, the two or more $R^{f}$ may be the same or different,
$Q^{1}$ is a single bond or a (a1+b1) valent linking group,
T is —$R^{f6}$, —Ar, —$OR^{10}$, —$SR^{10}$, —$NOR^{10}$, —C(=O)$R^{10}$, —N($R^{10}$)$_{2}$, —$N^{+}(R^{10})_{3}X^{3}$, —C≡N, —C(=N$R^{10}$)$R^{10}$, —$N^{+}$≡N, —N=N$R^{10}$, —C(=O)$OR^{10}$, —C(=O)$OX^{2}$, —C(=O)$OX^{4}$, —C(=O)OC(=O)$R^{10}$, —$SO_{2}R^{10}$, —$SO_{3}H$, —$SO_{3}X^{2}$, —O—P(=O)(—$OR^{10}$)$_{2}$, —O—P(=O)(—$OR^{10}$)(—$OX^{2}$), —N=C=O, —Si(R)$_{3-c}$(L)$_{c}$, —C($R^{10}$)=C($R^{10}$)$_{2}$, —C≡C($R^{10}$), —C(=O)N($R^{10}$)$_{2}$, —N($R^{10}$)C(=O)$R^{10}$, —Si($R^{10}$)$_{2}$—O—Si($R^{10}$)$_{3}$, —NH—C(=O)$R^{10}$, —C(=O)NH$R^{10}$, —I, or a group containing

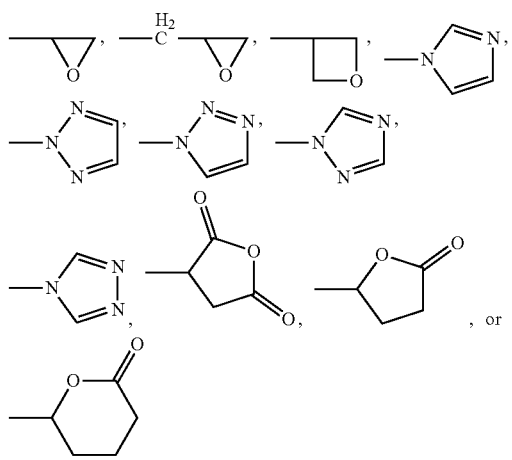

$R^{f6}$ is a $C_{1-6}$ fluoroalkyl group, $R^{10}$ is a hydrogen atom, a $C_{1-6}$ alkyl or fluoroalkyl group, or an aryl group which may have a substituent, and when there are two or more $R^{10}$, the two or more $R^{10}$ may be the same or different, Ar is an aryl group which may have a substituent, $X^2$ is an alkali metal ion or an ammonium ion, $X^3$ is a halide ion, $X^4$ is a halogen atom, R is an alkyl group, L is a hydrolyzable group or a hydroxy group, and the two or more L in T may be the same or different, a1 is an integer of at least 1, b1 is an integer of at least 1, and c is 2 or 3, provided that when there are two or more T, the two or more T may be the same or different.

[3] The fluorinated ether compound according to [2], wherein $R^f$ is a group represented by the following formula (g1a):

$$R^{f1}-(OR^{f2})_m(OR^{f3})_n-\quad\quad (g1a)$$

wherein $R^{f1}$ is a $C_{1-20}$ fluoroalkyl group or a monovalent fluorinated hydrocarbon group having a fluorinated cyclic structure, $R^{f2}$ is a $C_{1-6}$ fluoroalkylene group (provided that to the carbon atom at the terminal on the $Q^1$ side of $R^{f2}$ bonded to $Q^1$, at least one fluorine atom is bonded), $R^{f3}$ is a bivalent fluorinated hydrocarbon group having a fluorinated cyclic structure (provided that to the carbon atom at the terminal on the $Q^1$ side of $R^{f3}$ bonded to $Q^1$, at least one fluorine atom is bonded), n is an integer of from 0 to 500 when $R^{f1}$ has a fluorinated cyclic structure, or an integer of from 1 to 500 when $R^{f1}$ has no fluorinated cyclic structure, and when n is at least 2, $(OR^{f3})_n$ may consist of two or more types of $OR^{f3}$, when n is 0, m is an integer of from 5 to 500, and when n is at least 1, m is an integer of from 2 to 500, provided that when m is at least 2, $(OR^{f2})_m$ may consist of two or more types of $OR^{f2}$, and the bonding order of m $(OR^{f2})$ and n $(OR^{f3})$ is not limited.

[4] The fluorinated ether compound according to [2] or [3], wherein $Q^1$ is a group represented by the formula (g2-1) (provided that a1=d1+d3 and b1=d2+d4), a group represented by the formula (g2-2) (provided that a1=e1 and b1=e2), a group represented by the formula (g2-3) (provided that a1=1 and b1=2), a group represented by the formula (g2-4) (provided that a1=h1 and b1=h2), a group represented by the formula (g2-5) (provided that a1=i1 and b1=i2), a group represented by the formula (g2-6) (provided that a1=1 and b1=1), or a group represented by the formula (g2-7) (provided that a1=1 and b1=3).

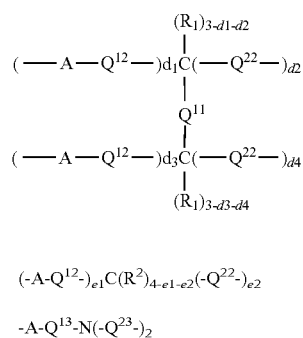

(g2-1)

$(-A-Q^{12}-)_{e1}C(R^2)_{4-e1-e2}(-Q^{22}-)_{e2}$ (g2-2)

$-A-Q^{13}-N(-Q^{23}-)_2$ (g2-3)

$(-A-Q^{14}-)_{h1}Z(-Q^{24}-)_{h2}$ (g2-4)

$(-A-Q^{15}-)_{i1}Si(R^3)_{4-i1-i2}(-Q^{25}-)_{i2}$ (g2-5)

$-A-Q^{26}-$ (g2-6)

$-A-Q^{12}-CH(-Q^{22}-)-Si(R^3)_{3-i3}(-Q^{25}-)_{i3}$ (g2-7)

wherein in the formulae (g2-1) to (g2-7), the A side is bonded to $R^f$, and the $Q^{22}$, $Q^{23}$, $Q^{24}$, $Q^{25}$ $Q^{26}$ side is bonded to T, A is a single bond, $-C(O)NR^6-$, $-C(O)-$, $-OC(O)O-$, $-NHC(O)O-$, $-NHC(O)NR^6-$, $-O-$ or $-SO_2NR^6-$, $Q^{11}$ is a single bond, $-O-$, an alkylene group or a group having $-C(O)NR^6-$, $-C(O)-$, $-NR^6-$ or $-O-$ between carbon atoms of an alkylene group having at least 2 carbon atoms, $Q^{12}$ is a single bond, an alkylene group or a group having $-C(O)NR^6-$, $-C(O)-$, $-NR^6-$ or $-O-$ between carbon atoms of an alkylene group having at least 2 carbon atoms, and when $Q^1$ has two or more $Q^{12}$, the two or more $Q^{12}$ may be the same or different, $Q^{13}$ is a single bond (provided that A is $-C(O)-$), an alkylene group, a group having $-C(O)NR^6-$, $-C(O)-$, $-NR^6-$ or $-O-$ between carbon atoms of an alkylene group having at least 2 carbon atoms, or an alkylene group having $-C(O)-$ at the terminal on the N side, $Q^{14}$ is $Q^{12}$ when the atom in Z to which $Q^{14}$ is bonded is a carbon atom, or $Q^{13}$ when the atom in Z to which $Q^{14}$ is bonded is a nitrogen atom, and when $Q^1$ has two or more $Q^{14}$, the two or more $Q^{14}$ may be the same or different, $Q^{15}$ is an alkylene group or a group having $-C(O)NR^6-$, $-C(O)-$, $-NR^6-$ or $-O-$ between carbon atoms of an alkylene group having at least 2 carbon atoms, and when $Q^1$ has two or more $Q^{15}$, the two or more $Q^{15}$ may be the same or different, $Q^{22}$ is an alkylene group, a group having $-C(O)NR^6-$, $-C(O)-$, $-NR^6-$ or $-O-$ between carbon atoms of an alkylene group having at least 2 carbon atoms, an alkylene group having $-C(O)NR^6-$, $-C(O)-$, $-NR^6-$ or $-O-$ at the terminal on the side not bonded to T, or a group having $-C(O)NR^6-$, $-C(O)-$, $-NR^6-$ or $-O-$ between carbon atoms of an alkylene group having at least 2 carbon atoms and having $-C(O)NR^6-$, $-C(O)-$, $-NR^6-$ or $-O-$ at the terminal on the side not bonded to T, and when $Q^1$ has two or more $Q^{22}$, the two or more $Q^{22}$ may be the same or different, $Q^{23}$ is an alkylene group or a group having $-C(O)NR^6-$, $-C(O)-$, $-NR^6-$ or $-O-$ between carbon atoms of an alkylene group having at least 2 carbon atoms, and the two $Q^{23}$ may be the same or different, $Q^{24}$ is $Q^{22}$ when the atom in Z to which $Q^{24}$ is bonded is a carbon atom, or $Q^{23}$ when the atom in Z to which $Q^{24}$ is bonded is a nitrogen atom, and when $Q^1$ has two or more $Q^{24}$, the two or more $Q^{24}$ may be the same or different, $Q^{25}$ is an alkylene group or a group having $-C(O)NR^6-$, $-C(O)-$, $-NR^6-$ or $-O-$ between carbon atoms of an alkylene group having at least 2 carbon atoms, and when $Q^1$ has two or more $Q^{25}$, the two or more $Q^{25}$ may be the same or different, $Q^{26}$ is an alkylene group or a group having $-C(O)NR^6-$, $-C(O)-$, $-NR^6-$ or $-O-$ between carbon atoms of an alkylene group having at least 2 carbon atoms, Z is a group having a (a1+b1) valent cyclic structure having a carbon atom or a nitrogen atom to which $Q^{14}$ is directly bonded and having a carbon atom or a nitrogen atom to which $Q^{24}$ is directly bonded, $R^1$ is a hydrogen atom or an alkyl group, and when $Q^1$ has two or more $R^1$, the two or more $R^1$ may be the same or different, $R^2$ is a hydrogen atom, a hydroxy group, an alkyl group or an acyloxy group, $R^3$ is an alkyl group, $R^6$ is a hydrogen atom, a $C_{1-6}$ alkyl group or a phenyl group, d1 is an integer of from 0 to 3, d2 is an integer of from 0 to 3, and d1+d2 is an integer of from 1 to 3, d3 is an integer of from 0 to 3, d4 is an integer of from 0 to 3, and d3+d4 is an integer of from 1 to 3, d1+d3 is an integer of from 1 to 5 in $Q^1$, d2+d4 is an integer of from 1 to 5 in $Q^1$, e1+e2 is 3 or 4, e1 is an integer of from 1 to 3 in $Q^1$, e2 is an integer of from 1 to 3 in $Q^1$, h1 is an integer of at least 1 in $Q^1$, h2 is an integer of at least 1, i1+i2 is 3 or 4, i1 is an integer of from 1 to 3 in $Q^1$, i2 is an integer of from 1 to 3 in $Q^1$, and i3 is 2 or 3.

[5] The fluorinated ether compound according to [1], which is a compound represented by the following formula (1B):

$$[T\text{-}]_{b2}Q^2\text{-}Q^f\text{-}Q^2[\text{-}T]_{b2} \qquad (1B)$$

wherein $Q^f$ is a bivalent group both the bond terminals of which are constituted by a carbon atom, which has the first partial structure and the second partial structure, and which has at least five first partial structures or has at least two second partial structures, $Q^2$ is a single bond or a b2+1 valent linking group, and the two $Q^2$ may be the same or different, T is —$R^{f6}$, —Ar, —$OR^{10}$, —$SR^{10}$, —$NOR^{10}$, —C(=O)$R^{10}$, —N($R^{10}$)$_2$, —$N^+(R^{10})_3X^3$, —C≡N, —C(=N$R^{10}$)—$R^{10}$, —$N^+$≡N, —N=N$R^{10}$, —C(=O)$OR^{10}$, —C(=O)$OX^2$, —C(=O)$OX^4$, —C(=O)OC(=O)$R^{10}$, —$SO_2R^{10}$, —$SO_3$H, —$SO_3X^2$, —O—P(=O)(—$OR^{10}$)$_2$, —O—P(=O)(—$OR^{10}$)(—$OX^2$), —N=C=O, —Si(R)$_{3\text{-}c}$(L)$_c$, —C($R^{10}$)=C($R^{10}$)$_2$, —C=C($R^{10}$), —C(=O)N($R^{10}$)$_2$, —N($R^{10}$)C(=O)$R^{10}$, —Si($R^{10}$)$_2$—O—Si($R^{10}$)$_3$, —NH—C(=O)$R^{10}$, —C(=O)NH$R^{10}$, —I, or a group containing

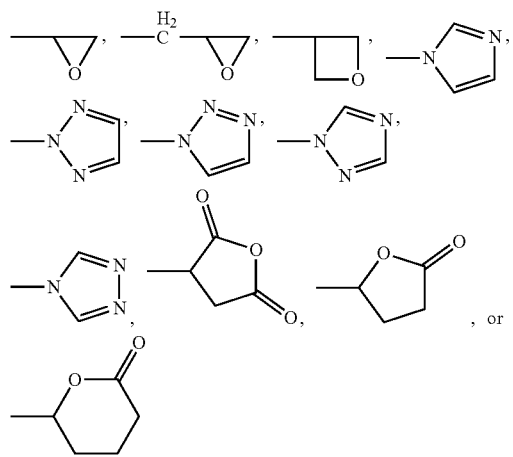

$R^{f6}$ is a $C_{1-6}$ fluoroalkyl group, $R^{10}$ is a hydrogen atom, a $C_{1-6}$ alkyl or fluoroalkyl group, or an aryl group which may have a substituent, and when there are two or more $R^{10}$, the two or more $R^{10}$ may be the same or different, Ar is an aryl group which may have a substituent, $X^2$ is an alkali metal ion or an ammonium ion, $X^3$ is a halide ion, $X^4$ is a halogen atom, R is an alkyl group, L is a hydrolyzable group or a hydroxy group, and the two or more L in T may be the same or different, b2 is an integer of at least 1, and the two b2 may be the same or different, c is 2 or 3, and when there are two or more T, the two or more T may be the same or different.

[6] The fluorinated ether compound according to [5], wherein $Q^f$ is a group represented by the following formula (g1b):

$$\text{—}R^{f4}\text{—}(OR^{f2})_m(OR^{f3})_n\text{—} \qquad (g1b)$$

wherein $R^{f2}$ is a $C_{1-6}$ fluoroalkylene group (provided that to the carbon atom at the terminal on the $Q^2$ side of $R^{f2}$ bonded to $Q^2$, at least one fluorine atom is bonded), $R^{f3}$ is a bivalent fluorinated hydrocarbon group having a fluorinated cyclic structure (provided that to the carbon atom at the terminal on the $Q^2$ side of $R^{f3}$ bonded to $Q^2$, at least one fluorine atom is bonded), $R^{f4}$ is a $C_{1-6}$ fluoroalkylene group or a bivalent fluorinated hydrocarbon group having a fluorinated cyclic structure (provided that to the carbon atom at the terminal on the $Q^2$ side of $R^{f4}$, at least one fluorine atom is bonded), n is an integer of from 0 to 500 when $R^{f4}$ has a fluorinated cyclic structure, or an integer of from 1 to 500 when $R^{f4}$ has no fluorinated cyclic structure, and when n is at least 2, $(OR^{f3})_n$ may consist of two or more types of $OR^{f3}$, when n is 0, m is an integer of from 5 to 500, and when n is at least 1, m is an integer of from 2 to 500, provided that when m is at least 2, $(OR^{f2})_m$ may consist of two or more types of $OR^{f2}$, and the bonding order of m $(OR^{f2})$ and n $(OR^{f3})$ is not limited.

[7] The fluorinated ether compound according to [5] or [6], wherein $Q^2$ is a group represented by the formula (g2-1) (provided that b2=d2+d4), a group represented by the formula (g2-2) (provided that b2=e2), a group represented by the formula (g2-3) (provided that b2=2), a group represented by the formula (g2-4) (provided that b2=h2), a group represented by the formula (g2-5) (provided that b2=i2), a group represented by the formula (g2-6) (provided that b2=1) or a group represented by the formula (g2-7) (provided that b2=i3):

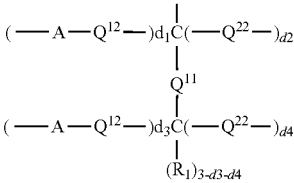
(g2-1)

$$(\text{-A-}Q^{12}\text{-})_{e1}C(R^2)_{4\text{-}e1\text{-}e2}(\text{-}Q^{22}\text{-})_{e2} \qquad (g2\text{-}2)$$

$$\text{-A-}Q^{13}\text{-N}(\text{-}Q^{23}\text{-})_2 \qquad (g2\text{-}3)$$

$$(\text{-A-}Q^{14}\text{-})_{h1}Z(\text{-}Q^{24}\text{-})_{h2} \qquad (g2\text{-}4)$$

$$(\text{-A-}Q^{15}\text{-})_{i1}Si(R^3)_{4\text{-}i1\text{-}i2}(\text{-}Q^{25}\text{-})_{i2} \qquad (g2\text{-}5)$$

-A-Q$^{26}$- (g2-6)

-A-Q$^{12}$-CH(-Q$^{22}$-)—Si(R$^3$)$_{3-i3}$(-Q$^{25}$-)$_{i3}$ (g2-7)

wherein in the formulae (g2-1) to (g2-7), the A side is bonded to Q$^f$, and the Q$^{22}$, Q$^{23}$, Q$^{24}$, Q$^{25}$ and Q$^{26}$ side is bonded to T, A is a single bond, —C(O)NR$^6$—, —C(O)—, —OC(O)O—, —NHC(O)O—, —NHC(O)NR$^6$—, —O— or —SO$_2$NR$^6$—, Q$^{11}$ is a single bond, —O—, an alkylene group or a group having —C(O)NR$^6$—, —C(O)—, —NR$^6$— or —O— between carbon atoms of an alkylene group having at least 2 carbon atoms, Q$^{12}$ is a single bond, an alkylene group or a group having —C(O)NR$^6$—, —C(O)—, —NR$^6$— or —O— between carbon atoms of an alkylene group having at least 2 carbon atoms, and when Q$^2$ has two or more Q$^{12}$, the two or more Q$^{12}$ may be the same or different, Q$^{13}$ is a single bond (provided that A is —C(O)—), an alkylene group, a group having —C(O)NR$^6$—, —C(O)—, —NR$^6$— or —O— between carbon atoms of an alkylene group having at least 2 carbon atoms, or an alkylene group having —C(O)— at the terminal on the N side, Q$^{14}$ is Q$^{12}$ when the atom in Z to which Q$^{14}$ is bonded is a carbon atom, or Q$^{13}$ when the atom in Z to which Q$^{14}$ is bonded is a nitrogen atom, and when Q$^2$ has two or more Q$^{14}$, the two or more Q$^{14}$ may be the same or different, Q$^{15}$ is an alkylene group or a group having —C(O)NR$^6$—, —C(O)—, —NR$^6$— or —O— between carbon atoms of an alkylene group having at least 2 carbon atoms, and when Q$^2$ has two or more Q$^{15}$, the two or more Q$^{15}$ may be the same or different, Q$^{22}$ is an alkylene group, a group having —C(O)NR$^6$—, —C(O)—, —NR$^6$— or —O— between carbon atoms of an alkylene group having at least 2 carbon atoms, an alkylene group having —C(O)NR$^6$—, —C(O)—, —NR$^6$— or —O— at the terminal on the side not bonded to T, or a group having —C(O)NR$^6$—, —C(O)—, —NR$^6$— or —O— between carbon atoms of an alkylene group having at least 2 carbon atoms and having —C(O)NR$^6$—, —C(O)—, —NR$^6$— or —O— at the terminal on the side not bonded to T, and when Q$^2$ has two or more Q$^{22}$, the two or more Q$^{22}$ may be the same or different, Q$^{23}$ is an alkylene group or a group having —C(O)NR$^6$—, —C(O)—, —NR$^6$— or —O— between carbon atoms of an alkylene group having at least 2 carbon atoms, and the two Q$^{23}$ may be the same or different, Q$^{24}$ is Q$^{22}$ when the atom in Z to which Q$^{24}$ is bonded is a carbon atom, or Q$^{23}$ when the atom in Z to which Q$^{24}$ is bonded is a nitrogen atom, and when Q$^2$ has two or more Q$^{24}$, the two or more Q$^{24}$ may be the same or different, Q$^{25}$ is an alkylene group or a group having —C(O)NR$^6$—, —C(O)—, —NR$^6$— or —O— between carbon atoms of an alkylene group having at least 2 carbon atoms, and when Q$^2$ has two or more Q$^{25}$, the two or more Q$^{25}$ may be the same or different, Q$^{26}$ is an alkylene group or a group having —C(O)NR$^6$—, —C(O)—, —NR$^6$— or —O— between carbon atoms of an alkylene group having at least 2 carbon atoms, Z is a group having a b2+1 valent cyclic structure having a carbon atom or a nitrogen atom to which Q$^{14}$ is directly bonded and having a carbon atom or a nitrogen atom to which Q$^{24}$ is directly bonded, R$^1$ is a hydrogen atom or an alkyl group, and when Q$^2$ has two or more R$^1$, the two or more R$^1$ may be the same or different, R$^2$ is a hydrogen atom, a hydroxy group, an alkyl group or an acyloxy group, R$^3$ is an alkyl group, R$^6$ is a hydrogen atom, a C$_{1-6}$ alkyl group or a phenyl group, d1 is an integer of from 0 to 3, d2 is an integer of from 0 to 3, and d1+d2 is an integer of from 1 to 3, d3 is an integer of from 0 to 3, d4 is an integer of from 0 to 3, and d3+d4 is an integer of from 1 to 3, d1+d3 is 1 in Q$^2$, d2+d4 is an integer of from 3 to 5 in Q$^2$, e1+e2 is 3 or 4, e1 is 1 in Q$^2$, e2 is 2 or 3 in Q$^2$, h1 is 1 in Q$^2$, h2 is an integer of at least 1, i1+i2 is 3 or 4, i1 is 1 in Q$^2$, i2 is 2 or 3 in Q$^2$, and i3 is 2 or 3.

[8] The fluorinated ether compound according to any one of [1] to [7], wherein the fluorinated cyclic structure is a four-membered ring.

[9] The fluorinated ether compound according to any one of [1] to [8], which has a number average molecular weight of at least 2,500.

[10] The fluorinated ether compound according to any one of [2] to [9], wherein T is —Si(R)$_{3-c}$(L)$_c$, wherein R is an alkyl group, L is a hydrolyzable group or a hydroxy group, and the two or more L in T may be the same or different, and c is 2 or 3.

[11] A fluorinated ether composition comprising at least one type of the fluorinated ether compound as defined in any one of [1] to [10], and other fluorinated ether compound.

[12] A coating liquid comprising the fluorinated ether compound as defined in any one of [1] to [10] or the fluorinated ether composition as defined in [11], and a liquid medium.

13. An article comprising a substrate and a surface layer formed of the fluorinated ether compound as defined in any one of [1] to [10] or the fluorinated ether composition as defined in [11] on a surface of the substrate.

[14] The article according to [13], which has the surface layer on a surface of a member constituting a plane of a touch panel to be touched with fingers.

[15] A method for producing an article, which comprises treating a surface of a substrate by dry coating method using the fluorinated ether compound as defined in any one of [1] to [10] or the fluorinated ether composition as defined in [11] to form a surface layer formed of the fluorinated ether compound or the fluorinated ether composition on the surface of the substrate.

[16] A method for producing an article, which comprises applying the coating liquid as defined in [12] to a surface of a substrate by wet coating method, followed by drying to form a surface layer formed of the fluorinated ether compound or the fluorinated ether composition on the surface of the substrate.

[17] A fluorinated ether compound, which is a compound represented by the following formula (2A):

[R$^f$—]$_{a1}$Q$^{10}$[—CH=CH$_2$]$_{b1}$ (2A)

wherein R$^f$ is a monovalent polyfluoropolyether chain, the bond terminal of which is constituted by a carbon atom, and which has at least one of a monovalent fluorinated cyclic structure at its free end and a bivalent fluorinated cyclic structure in its main chain (provided that at least one fluorine atom is bonded to the carbon atom at the bond terminal), and when there are two or more $R^f$, the two or more $R^f$ may be the same or different, $Q^{10}$ is a (a1+b1) valent linking group, a1 is an integer of at least 1, and b1 is an integer of at least 1.

[18] A fluorinated ether compound, which is a compound represented by the following formula (2B):

$$[CH_2\!=\!CH\!-\!]_{b2}Q^{20}\text{-}Q^f\text{-}Q^{20}[-CH\!=\!CH_2]_{b2} \quad (2B)$$

wherein $Q^f$ is a bivalent polyfluoropolyether chain, both the bond terminals of which are constituted by a carbon atom, and which has a bivalent fluorinated cyclic structure in its main chain (provided that at least one fluorine atom is bonded to the carbon atom at each of both bond terminals), $Q^{20}$ is a b2+1 valent linking group, and the two $Q^{20}$ may be the same or different, and b2 is an integer of at least 1, and the two b2 may be the same or different.

[19] A method for producing a fluorinated compound, which comprises reacting a compound represented by the following formula (11) and a compound represented by the following formula (12) to obtain a compound represented by the following formula (21):

(11)

(12)

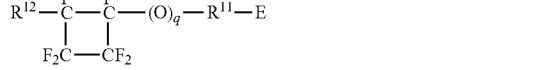
(21)

wherein $R^{11}$ is an alkylene group, a group having —O— between carbon atoms of an alkylene group having at least 2 carbon atoms, a fluoroalkylene group (provided that when E is —OH, the terminal on the E side is $CH_2$) or a group having —O— between carbon atoms of a fluoroalkylene group having at least 2 carbon atoms (provided that when E is —OH, the terminal on the E side is $CH_2$), $R^{12}$ is a halogen atom, a perfluoroalkyl group or a group having —O— between carbon atoms of a perfluoroalkyl group having at least 2 carbon atoms, q is 0 or 1, E is —OH, —OR$^{14}$, —SR$^{14}$, —C(O)OR$^{14}$, —C(O) NHR$^{14}$, —C(O)NR$^{14}$R$^{15}$, —NH$_2$, —NHR$^{14}$, —NR$^{14}$R$^{15}$, —SO$_2$X$^1$, —C(O)X$^1$, or a halogen atom, $R^{14}$ and $R^{15}$ are each independently an alkyl group, and $X^1$ is a halogen atom.

[20] A method for producing a fluorinated compound, which comprises reacting a compound represented by the following formula (11) and a compound represented by the following formula (13) to obtain a compound represented by the following formula (22):

(11)

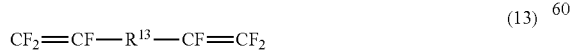
(13)

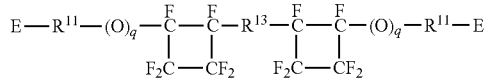
(22)

wherein $R^{11}$ is an alkylene group, a group having —O— between carbon atoms of an alkylene group having at least 2 carbon atoms, a fluoroalkylene group (provided that when E is —OH, the terminal on the E side is $CH_2$) or a group having —O— between carbon atoms of a fluoroalkylene group having at least 2 carbon atoms (provided that when E is —OH, the terminal on the E side is $CH_2$), $R^{13}$ is a fluoroalkylene group, a fluoroalkylene group having —O— at both terminals or a group having —O— between carbon atoms of a fluoroalkylene group having at least 2 carbon atoms, q is 0 or 1, E is —OH, —OR$^{14}$, —SR$^{14}$, —C(O)OR$^{14}$, —C(O) NHR$^{14}$, —C(O)NR$^{14}$R$^{15}$, —NH$_2$, —NHR$^{14}$, —NR$^{14}$R$^{15}$, —SO$_2$X$^1$, —C(O)X$^1$, or a halogen atom, $R^{14}$ and $R^{15}$ are each independently an alkyl group, and $X^1$ is a halogen atom, provided that the two $R^{11}$, the two q and the two E in the formula (22) may be the same or different respectively.

[21] A method for producing a fluorinated compound, which comprises reacting one or more compounds represented by the following formula (11) to obtain a compound represented by the following formula (23):

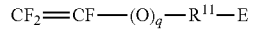
(11)

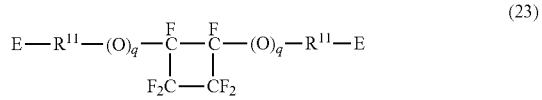
(23)

wherein $R^{11}$ is an alkylene group, a group having —O— between carbon atoms of an alkylene group having at least 2 carbon atoms, a fluoroalkylene group (provided that when E is —OH, the terminal on the E side is $CH_2$) or a group having —O— between carbon atoms of a fluoroalkylene group having at least 2 carbon atoms (provided that when E is —OH, the terminal on the E side is $CH_2$), q is 0 or 1, E is —OH, —OR$^{14}$, —SR$^{14}$, —C(O)OR$^{14}$, —C(O) NHR$^{14}$, —C(O)NR$^{14}$R$^{15}$, —NH$_2$, —NHR$^{14}$, —NR$^{14}$R$^{15}$, —SO$_2$X$^1$, —C(O)X$^1$, or a halogen atom, $R^{14}$ and $R^{15}$ are each independently an alkyl group, and $X^1$ is a halogen atom, provided that the two of $R^{11}$, the two q and the two E in the formula (23) may be the same or different respectively.

[22] A method for producing a fluorinated compound, which comprises reacting one or more compounds represented by the following formula (13) to obtain a compound represented by the following formula (24):

$$CF_2\!=\!CF\!-\!R^{13}\!-\!CF\!=\!CF_2 \quad (13)$$

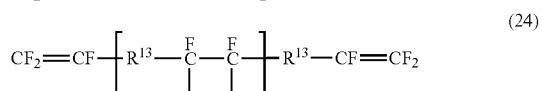
(24)

wherein $R^{13}$ is a fluoroalkylene group, a fluoroalkylene group having —O— at both terminals or a group having —O— between carbon atoms of a fluoroalkylene group having at least 2 carbon atoms, and r is an integer of at least 1, provided that the two or more $R^{13}$ in the formula (24) may be the same or different.

[23] A method for producing a fluorinated compound, which comprises reacting a compound represented by the following formula (11) and a compound represented by the following formula (13) to obtain a compound represented by the following formula (25):

$$CF_2 = CF - (O)_q - R^{11} - E \quad (11)$$

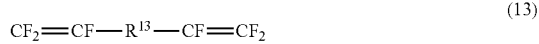

$$CF_2 = CF - R^{13} - CF = CF_2 \quad (13)$$

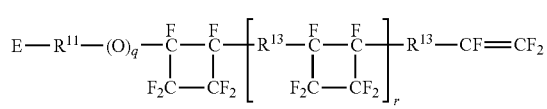

(25)

wherein $R^{11}$ is an alkylene group, a group having —O— between carbon atoms of an alkylene group having at least 2 carbon atoms, a fluoroalkylene group (provided that when E is —OH, the terminal on the E side is $CH_2$) or a group having —O— between carbon atoms of a fluoroalkylene group having at least 2 carbon atoms (provided that when E is —OH, the terminal on the E side is $CH_2$), $R^{13}$ is a fluoroalkylene group, a fluoroalkylene group having —O— at both terminals or a group having —O— between carbon atoms of a fluoroalkylene group having at least 2 carbon atoms, q is 0 or 1, r is an integer of at least 1, E is —OH, —OR$^{14}$, —SR$^{14}$, —C(O)OR$^{14}$, —C(O)NHR$^{14}$, —C(O)NR$^{14}$R$^{15}$, —NH$_2$, —NHR$^{14}$, —NR$^{14}$R$^{15}$, —SO$_2$X$^1$, —C(O)X$^1$, or a halogen atom, $R^{14}$ and $R^{15}$ are each independently an alkyl group, and $X^1$ is a halogen atom, provided that the two or more $R^{13}$ in the formula (25) may be the same or different.

[24] A method for producing a fluorinated compound, which comprises reacting one or more compounds represented by the following formula (12) to obtain a compound represented by the following formula (26):

$$CF_2 = CF - R^{12} \quad (12)$$

(26)

wherein $R^{12}$ is a halogen atom, a perfluoroalkyl group or a group having —O— between carbon atoms of a perfluoroalkyl group having at least 2 carbon atoms, provided that the two $R^{12}$ in the formula (26) may be the same or different.

[25] A method for producing a fluorinated compound, which comprises reacting a compound represented by the following formula (12) and a compound represented by the following formula (13) to obtain a compound represented by the following formula (27):

$$CF_2 = CF - R^{12} \quad (12)$$

$$CF_2 = CF - R^{13} - CF = CF_2 \quad (13)$$

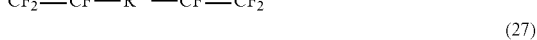

(27)

wherein $R^{12}$ is a halogen atom, a perfluoroalkyl group or a group having —O— between carbon atoms of a perfluoroalkyl group having at least 2 carbon atoms, $R^{13}$ is a fluoroalkylene group, a fluoroalkylene group having —O— at both terminals or a group having —O— between carbon atoms of a fluoroalkylene group having at least 2 carbon atoms, and r2 is an integer of at least 1, provided that the two or more $R^{13}$ in the formula (27) may be the same or different.

Advantageous Effects of Invention

According to the present invention, there are provided a fluorinated ether compound excellent in chemical resistance, a fluorinated ether composition and a coating liquid capable of forming a surface layer excellent in chemical resistance, an article having a surface layer excellent in chemical resistance and its production method, and a method for producing a fluorinated compound useful as a raw material of the fluorinated ether compound.

DESCRIPTION OF EMBODIMENTS

In this specification, a compound represented by the formula (1A) will be referred to as compound (1A). Compounds represented by other formulae will be referred to in the same manner.

Further, a group represented by the formula (g1a) will be referred to as group (g1a). Groups represented by other formulae will be referred to in the same manner.

An "oxyfluoro(cyclo)alkylene" generally means an oxyfluoroalkylene and an oxyfluorocycloalkylene.

The chemical formula of an oxyfluoro(cyclo)alkylene unit is represented so that the oxygen atom is on the left side of a fluoro(cyclo)alkylene group.

In this specification, meanings of the following terms are as follows.

A "free end" means a terminal not on the side to which a reactive silyl group is bonded via a linking group, in a polyfluoropolyether chain.

A "terminal region" means a range constituted by oxyfluoro(cyclo)alkylene units containing the "free end".

A "fluorinated cyclic structure" means a group containing a group having one or more of hydrogen atoms bonded to carbon atoms constituting an alicyclic ring or an aromatic ring, substituted with a fluorine atom, and may contain in its carbon chain a hetero atom such as an oxygen atom, a nitrogen atom or a sulfur atom. A "fluorinated cyclic structure" may, for example, be a group containing a fluoroaryl group, a fluoroarylene group, a fluorocycloalkyl group, a fluorocycloalkylene group or the like.

A "monovalent fluorinated cyclic structure at the free end" means a cyclic structure in which one carbon atom constituting the fluorinated ring is a carbon atom at the terminal of the main chain of the polyfluoropolyether chain, on the side not bonded to the linking group, and means a fluorinated cyclic structure constituting the terminal region. The "monovalent fluorinated cyclic structure at the free end" may be a monovalent group containing a fluorocycloalkyl group, a fluoroaryl group or the like.

A "bivalent fluorinated cyclic structure in the main chain" means a cyclic structure in which at least one carbon atom constituting the fluorinated ring is a carbon atom constituting the main chain of the polyfluoropolyether chain. The "bivalent fluorinated cyclic structure in the main chain" may, for example, be a bivalent group containing a fluorocycloalkylene group, a fluoroarylene group or the like.

The "fluorinated alicyclic structure" means a group in which one or more of hydrogen atoms bonded to carbon atoms constituting the alicyclic ring is substituted with a fluorine atom, and atoms constituting the fluorinated alicyclic ring may include an oxygen atom, a nitrogen atom and the like in addition to the carbon atoms, and preferably consist solely of carbon atoms or carbon atoms and oxygen atoms. The "fluorinated alicyclic structure" may be a group containing a fluorocycloalkyl group, a fluorocycloalkylene group or the like.

A "reactive silyl group" generally means a hydrolyzable silyl group and a silanol group (Si—OH). The reactive silyl group may, for example, be $-Si(R)_{3-c}(L)_c$ described hereinafter.

The "hydrolyzable silyl group" means a group capable of forming a silanol group by being hydrolyzed.

A "surface layer" means a layer formed on the surface of a substrate.

When the fluorinated ether compound is a mixture of fluorinated ether compounds differing in the chain length of the polyfluoropolyether chain ($R^f$ or $Q^f$), the "molecular weight" of the polyfluoropolyether chain ($R^f$ or $Q^f$) is a number average molecular weight calculated from the number (average value) of oxyfluoro(cyclo)alkylene units on the basis of terminal groups, by means of $^1$H-NMR and $^{19}$F-NMR. The terminal group is, for example, $R^{f1}$ in the formula (g1a) or T in the formula (1A) or (1B).

When the fluorinated ether compound is a fluorinated ether compound having a single chain length of the polyfluoropolyether chain ($R^f$ or $Q^f$), the "molecular weight" of the polyfluoropolyether chain ($R^f$ or $Q^f$) is a molecular weight calculated by determining the structure of $R^f$ by means of $^1$H-NMR and $^{19}$F-NMR.

[Fluorinated Ether Compound]

The fluorinated ether compound of the present invention (hereinafter sometimes referred to as "the present compound") is a compound having a polyfluoropolyether chain, and the polyfluoropolyether chain has a fluorinated cyclic structure. The fluorinated cyclic structure may have at least one hetero atom.

By the polyfluoropolyether chain having the above-described specific fluorinated cyclic structure, the compound is excellent in chemical resistance.

In the present compound, when the polyfluoropolyether chain has one fluorinated cyclic structure, the polyfluoropolyether chain has at least 5 oxyfluoroalkylene units, whereby flexibility is imparted to the polyfluoropolyether chain and in addition, a fluorine amount sufficient to impart various properties of the fluorinated ether compound is secured.

Further, in the present compound, when the polyfluoropolyether chain has at least 2 fluorinated cyclic structures, the polyfluoropolyether chain has at least 2 (preferably at least 5) oxyfluoroalkylene units, whereby flexibility is imparted to the polyfluoropolyether chain and in addition, a fluorine amount sufficient to impart various properties of the fluorinated ether compound is secured.

The fluorinated cyclic structure is $OR^{f13}$ (second partial structure) described hereinafter. Further, the oxyfluoroalkylene group is $OR^{f12}$ (first partial structure) described hereinafter.

The polyfluoropolyether chain is preferably a perfluoropolyether chain in view of excellent effect to impart various properties by fluorine. Further, in view of excellent effect to impart various properties by fluorine, the molecular weight of the present compound is preferably at least 2,500, more preferably from 2,500 to 100,000, further preferably from 3,000 to 10,000.

The present compound preferably has a structure having the polyfluoropolyether chain and a group which imparts various functions to the present compound (T in the formula (1A) and the formula (1B) described hereinafter (hereinafter sometimes referred to as function-imparting group T)) connected directly or via a linking group.

The polyfluoropolyether chain in the present invention has a fluorinated cyclic structure which may have a hetero atom.

In the case of a monovalent polyfluoropolyether chain, it has at least one of a monovalent fluorinated cyclic structure at the free end and a bivalent fluorinated cyclic structure in its main chain.

In the case of a bivalent polyfluoropolyether chain, it has a bivalent fluorinated cyclic structure in its main chain.

By the polyfluoropolyether chain having the fluorinated cyclic structure, the compound will be excellent in chemical resistance and will be excellent in various durability such as light resistance.

The fluorinated cyclic structure is, in that the present compound will readily be produced, preferably a 3- to 8-membered ring, and in that the resulting surface layer will be more excellent in abrasion resistance and sliding resistance, more preferably a 4- to 6-membered ring, further preferably a 4- to 5-membered ring, particularly preferably a 4-membered ring.

The present compound is a fluorinated ether compound which has a first partial structure represented by the following formula (1) (hereinafter sometimes referred to as "the partial structure 1") and a second partial structure represented by the following formula (2) (hereinafter sometimes referred to as "the partial structure 2"), and which has at least five first partial structures, or has at least two second partial structures:

   (1)

   (2)

wherein $R^{f12}$ is a $C_{1-6}$ fluoroalkylene group, and $R^{f13}$ is a group having a fluorinated cyclic structure which may have a hetero atom.

The present compound preferably has one partial structure 2 and has at least 5 partial structures 1, in view of high fingerprint stain removability.

In the partial structure 1, since the fluoroalkylene group as $R^{f12}$ has from 1 to 6 carbon atoms, flexibility is imparted to the polyfluoropolyether chain, and the surface layer formed will be excellent in abrasion resistance and fingerprint stain removability.

The fluoroalkylene group as $R^{f12}$ is, in that the resulting surface layer will be more excellent in abrasion resistance and fingerprint stain removability, preferably a linear fluoroalkylene group.

The fluoroalkylene group as $R^{f12}$ is, in that the resulting surface layer will be more excellent in abrasion resistance and fingerprint stain removability, preferably a perfluoroalkylene group.

The proportion of the perfluoroalkylene group in the entire $R^{f12}$ is, in that the resulting surface layer will be more excellent in abrasion resistance and fingerprint stain removability, preferably at least 60 mol %, more preferably at least 80 mol %, particularly preferably 100 mol %.

In the partial structure 2, the group having a fluorinated cyclic structure which may have a hetero atom as $R^{f13}$ may, for example be a fluorocycloalkylene group which may have a hetero atom and which may have a substituent. The hetero atom may, for example, be an oxygen atom, a nitrogen atom or a sulfur atom, and is preferably an oxygen atom. The number of members in the ring containing a hetero atom is, in that the present compound will readily be produced, preferably from 3 to 8, and in that the resulting surface layer will be more excellent in abrasion resistance and sliding resistance, more preferably from 4 to 6, further preferably from 4 to 5, particularly preferably 4. Further, in view of excellent chemical resistance, the fluorinated cyclic structure is preferably a fluorinated cyclic structure having no hetero atom. Further, the fluorinated cyclic structure is preferably a fluorinated alicyclic structure.

The fluorocycloalkylene group which is a bivalent fluorinated alicyclic structure is, in that the resulting surface layer will be more excellent in abrasion resistance and fingerprint stain removability, preferably a perfluorocycloalkylene group. The fluorocycloalkylene group may have, as a substituent, for example, a fluoroalkylene group. The number of carbon atoms in the fluoroalkylene group is preferably from 1 to 6, more preferably from 1 to 4. The fluoroalkylene group is preferably a perfluoroalkylene group.

Further, the fluoroalkylene group as a substituent may be bonded to the oxygen atom in the formula (2). In such a case, the formula (2) is represented by the following formula (2a).

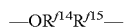   (2a)

wherein $R^{f14}$ is a $C_{1-6}$ fluoroalkylene group, and $R^{f15}$ is a fluorinated cyclic structure which may have a hetero atom. $R^{f14}R^{f15}$ represents $R^{f13}$.

Further, the present compound may have the partial structure 2 at the terminal region of the polyfluoropolyether chain. In such a case, the terminal region is represented by the following formula (2b):

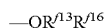   (2b)

wherein $R^{f13}$ is as described above, and $R^{f16}$ is a hydrogen atom, a fluorine atom or a $C_{1-6}$ fluoroalkyl group, hereinafter, $R^{f13}R^{f16}$ may sometimes be referred to as a monovalent fluorinated cyclic structure.

As the monovalent fluorinated cyclic structure, for example, groups of the following formulae may be mentioned. * in the formulae represents a connecting bond.

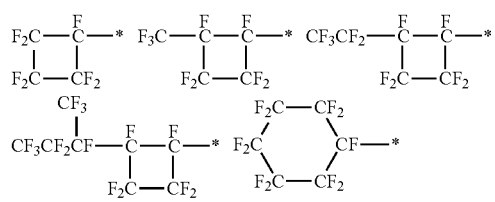

The bivalent fluorinated cyclic structure may, for example, be a fluorocycloalkylene group, or a group having —O— between carbon atoms of a fluorocycloalkylene group. The number of carbon atoms in the fluorocycloalkylene group is, in that the present compound will readily be produced, preferably from 3 to 8, and in that the resulting surface layer will be more excellent in abrasion resistance and sliding resistance, more preferably from 4 to 6, particularly preferably 4.

The fluorocycloalkylene group is, in that the resulting surface layer will be more excellent in abrasion resistance and fingerprint stain removability, preferably a perfluorocycloalkylene group. The fluorocycloalkylene group may have, as a substituent, for example, a fluoroalkyl group.

As the bivalent fluorinated cyclic structure, for example, groups of the following formulae may be mentioned. * in the formulae represent a connecting bond.

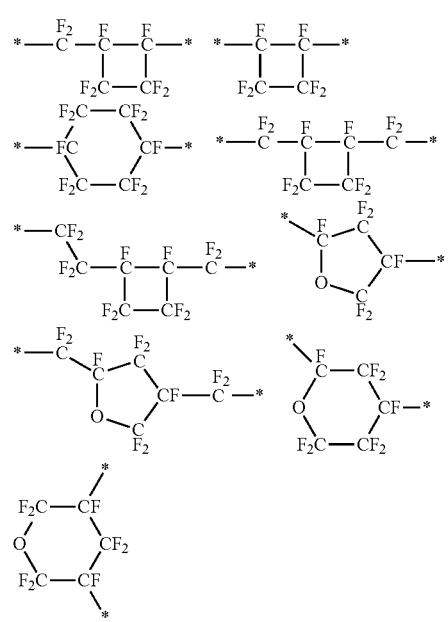

The molecular weight of the polyfluoropolyether chain is, in that the resulting surface layer will be excellent in both fingerprint stain removability and sliding resistance, and in view of chemical resistance, preferably from 100 to 6000, more preferably from 500 to 5000, particularly preferably from 1000 to 4000. When the molecular weight of the polyfluoropolyether chain is at least the lower limit value of the above range, the surface layer will be more excellent in fingerprint stain removability. When the molecular weight of the polyfluoropolyether chain is at most the above upper limit value of the above range, the surface layer will be more excellent in sliding resistance.

The molecular weight of the polyfluoropolyether chain is, in that the resulting surface layer will be more excellent in abrasion resistance and fingerprint stain removability, and in view of chemical resistance, preferably from 1500 to 10000, more preferably from 2000 to 8000, particularly preferably from 2500 to 6000. When the molecular weight of the polyfluoropolyether chain is at least the lower limit value of the above range, the surface layer will be more excellent in abrasion resistance and fingerprint stain removability. When the molecular weight of the polyfluoropolyether chain is at most the upper limit value of the above range, the surface layer will be more excellent in abrasion resistance.

(Compound (1A) and Compound (1B))

The present compound is, in that the resulting surface layer will be more excellent in abrasion resistance and fingerprint stain removability, preferably compound (1A) or compound (1B).

$R^f$ is a monovalent group the bond terminal of which is constituted by a carbon atom, which has the partial structure 1 and the partial structure 2, and which has at least five partial structures 1 or has at least two partial structures 2, and when there are two or more $R^f$, the two or more $R^f$ may be the same or different.

$Q^f$ is a bivalent group both the bond terminals of which are constituted by a carbon atom, which has the partial structure 1 and the partial structure 2, and which has at least five partial structures 1 or has at least two partial structures 2.

Particularly, the compound (1B) preferably has only one partial structure 2 and has at least five partial structures 1, in view of high fingerprint stain removability. Particularly, the total of the molecular weight of the partial structures 1 is preferably from 1000 to 10000, particularly preferably from 2000 to 6000.

$Q^1$ is a single bond or a (a1+b1) valent linking group, and $Q^2$ is a single bond or a b2+1 valent linking group, and the two $Q^2$ may be the same or different.

T is —$R^{f6}$, —Ar, —$OR^{10}$, —$SR^{10}$, —$NOR^{10}$, —C(=O)$R^{10}$, —N($R^{10}$)$_2$, —N$^+$($R^{10}$)$_3$X$^3$, —C≡N, —C(=N$R^{10}$)—$R^{10}$, —N$^+$≡N, —N=N$R^{10}$, —C(=O)O$R^{10}$, —C(=O)OX$^2$, —C(=O)OX$^4$, —C(=O)OC(=O)$R^{10}$, —SO$_2R^{10}$, —SO$_3$H, —SO$_3$X$^2$, —O—P(=O)(—O$R^{10}$)$_2$, —O—P(=O)(—O$R^{10}$)(—OX$^2$), —N=C=O, —Si(R)$_{3-c}$(L)$_c$, —C($R^{10}$)=C($R^{10}$)$_2$, —C≡C($R^{10}$), —C(=O)N($R^{10}$)$_2$, —N($R^{10}$)C(=O)$R^{10}$, —Si($R^{10}$)$_2$—O—Si($R^{10}$)$_3$, —NH—C(=O)$R^{10}$, —C(=O)NHR$^{10}$, —I, or a group containing

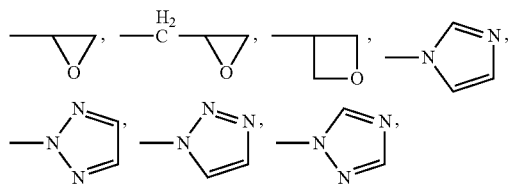

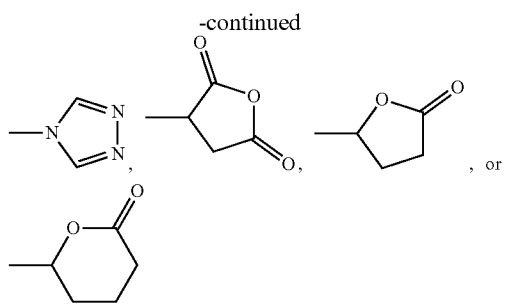

$R^{f6}$ is a $C_{1-6}$ fluoroalkyl group, $R^{10}$ is a hydrogen atom, a $C_{1-6}$ alkyl or fluoroalkyl group which may have a substituent, or an aryl group which may have a substituent, and when there are two or more $R^{10}$, the two or more $R^{10}$ may be the same or different, Ar is an aryl group which may have a substituent, $X^2$ is an alkali metal ion or an ammonium ion, $X^3$ is a halide ion, $X^4$ is a halogen atom, R is an alkyl group, L is a hydrolyzable group or a hydroxy group, and the two or more L in T may be the same or different, b2 is an integer of at least 1, and the two b2 may be the same or different, and c is 2 or 3, provided that when there are two or more T, the two or more T may be the same or different.

The compound (1A) has $R^f$ at its terminal. The compound (1A) having $R^f$ at its terminal is excellent in chemical resistance and provides a surface layer excellent in fingerprint stain removability. The compound (1B) has $Q^f$. The compound (1B) having $Q^f$ is excellent in chemical resistance and provides a surface layer excellent in fingerprint stain removability.

The compound (1A) and the compound (1B) have the above specific function-imparting group T at their terminal. The compound (1A) and the compound (1B) having the function-imparting group T at their terminal have various functions imparted, such that the compounds are strongly chemically bonded to a substrate to provide a surface layer excellent in abrasion resistance.

a1 is, in that the compound (1A) will readily be produced, in view of excellent chemical resistance, and in that the resulting surface layer will be more excellent in abrasion resistance and fingerprint stain removability, preferably from 1 to 6, more preferably from 1 to 4, particularly preferably 1 or 2.

b1 is, in that the compound (1A) will readily be produced, in view of excellent chemical resistance, and in that the resulting surface layer will be more excellent in abrasion resistance and fingerprint stain removability, preferably from 1 to 6, more preferably from 1 to 5, further preferably from 1 to 4, particularly preferably from 2 to 4. b2 is, in that the compound (1B) will readily be produced, in view of excellent chemical resistance, and in that the resulting surface layer will be more excellent in abrasion resistance and fingerprint stain removability, preferably from 1 to 6, more preferably from 1 to 5, further preferably from 1 to 4, particularly preferably from 2 to 4.

$R^f$ is a monovalent polyfluoropolyether chain, the bond terminal of which is constituted by a carbon atom. $R^f$ is, in view of excellent chemical resistance, and in that the resulting surface layer will be more excellent in abrasion resistance and fingerprint stain removability, more preferably a monovalent perfluoropolyether chain.

$Q^f$ is a bivalent polyfluoropolyether chain both the bond terminals of which are constituted by a carbon atom. $Q^f$ is, in view of excellent chemical resistance and in that the resulting surface layer will be more excellent in abrasion resistance and fingerprint stain removability, preferably a bivalent perfluoropolyether chain.

Preferred ranges of the molecular weights of $R^f$ and $Q^f$ are the same as the preferred range of the molecular weight of the polyfluoropolyether chain.

$R^f$ may, for example, be group (g1a). The group (g1a) has at least one fluorinated cyclic structure.

$$R^{f1}\text{—}(OR^{f2})_m(OR^{f3})_n\text{—} \qquad (g1a)$$

wherein $R^{f1}$ is a $C_{1-20}$ fluoroalkyl group, or a monovalent fluorinated hydrocarbon group having a fluorinated cyclic structure. $R^{f2}$ is a $C_{1-6}$ fluoroalkylene group (provided that to the carbon atom at the terminal on the $Q^1$ side of $R^{f2}$ bonded to $Q^1$, at least one fluorine atom is bonded). $R^{f3}$ is a bivalent fluorinated hydrocarbon group having a fluorinated cyclic structure (provided that to the carbon atom at the terminal on the $Q^1$ side of $R^{f3}$ bonded to $Q^1$, at least one fluorine atom is bonded).

n is an integer of from 0 to 500 when $R^{f1}$ has a fluorinated cyclic structure, or an integer of from 1 to 500 when $R^{f1}$ has no fluorinated cyclic structure, and when n is at least 2, $(OR^{f3})_n$ may consist of two or more types of $OR^{f3}$.

Further, when n is 0, m is an integer of from 5 to 500, when n is at least 1, m is an integer of from 2 to 500, and when m is at least 2, $(OR^{f2})_m$ may consist of two or more types of $OR^{f2}$, and the bonding order of m $(OR^{f2})$ and n $(OR^{f3})$ is not limited.

$Q^f$ may, for example, be a group having group (g1b). The group (g1b) has at least one fluorinated cyclic structure.

$$\text{—}R^{f4}\text{—}(OR^{f2})_m(OR^{f3})_n\text{—} \qquad (g1b)$$

wherein $R^{f2}$ is a $C_{1-6}$ fluoroalkylene group (provided that to the carbon atom at the terminal on the $Q^2$ side of $R^{f2}$ bonded to $Q^2$, at least one fluorine atom is bonded). $R^{f3}$ is a bivalent fluorinated hydrocarbon group having a fluorinated cyclic structure (provided that to the carbon atom at the terminal on the $Q^2$ side of $R^{f3}$ bonded to $Q^2$, at least one fluorine atom is bonded). $R^{f4}$ is a $C_{1-6}$ fluoroalkylene group, or a bivalent fluorinated hydrocarbon group having a fluorinated cyclic structure (provided that to the carbon atom at the terminal on the $Q^2$ side of $R^{f4}$, at least one fluorine atom is bonded).

n is an integer of from 0 to 500 when $R^{f4}$ has a fluorinated cyclic structure, or an integer of from 1 to 500 when $R^{f4}$ has no fluorinated cyclic structure, and when n is at least 2, $(OR^{f3})_n$ may consist of two or more types of $OR^{f3}$.

Further, when n is 0, m is an integer of from 5 to 500, when n is at least 1, m is an integer of from 2 to 500, and when m is at least 2, $(OR^{f2})_m$ may consist of two or more types of $OR^{f2}$, and the bonding order of m $(OR^{f2})$ and n $(OR^{f3})$ is not limited.

As $Q^f$, group (g1b1) is particularly preferred.

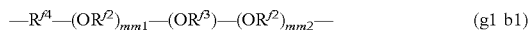
$$\text{—}R^{f4}\text{—}(OR^{f2})_{mm1}\text{—}(OR^{f3})\text{—}(OR^{f2})_{mm2}\text{—} \qquad (g1b1)$$

wherein mm1+mm2=m, and n=1. In the group (g1b1), it is preferred that (mm1+1) and (mm2) are substantially the same, in view of abrasion resistance. "Substantially the same" means that the ratio (mm1+1)/mm2 is from 0.5 to 2, preferably from 0.75 to 1.33.

When the fluoroalkyl group as $R^{f1}$ has from 1 to 20 carbon atoms, excellent chemical resistance will be obtained, and the resulting surface layer will be more excellent in abrasion resistance and fingerprint stain removability. The number of carbon atoms in the fluoroalkyl group as $R^{f1}$ is, in view of excellent chemical resistance and in that the resulting surface layer will be more excellent in abrasion resistance and fingerprint stain removability, preferably from 1 to 6, more preferably from 1 to 4, particularly preferably from 1 to 3.

The fluoroalkyl group as $R^{f1}$ is, in view of excellent chemical resistance and in that the resulting surface layer will be more excellent in abrasion resistance and fingerprint stain removability, preferably a perfluoroalkyl group. The compound (1A) wherein $R^{f1}$ is a perfluoroalkyl group has $CF_3\text{—}$ at its terminal. Since the compound (1A) having $CF_3\text{—}$ at its terminal can form a surface layer having a low surface energy, the resulting surface layer will be more excellent in abrasion resistance and fingerprint stain removability.

As the fluoroalkyl group as $R^{f1}$, for example, $CF_3\text{—}$, $CF_3CF_2\text{—}$, $CF_3CF_2CF_2\text{—}$, $CF_3CF_2CF_2CF_2\text{—}$, $CF_3CF_2CF_2CF_2CF_2\text{—}$, $CF_3CF_2CF_2CF_2CF_2CF_2\text{—}$, $CF_3CF(CF_3)\text{—}$, and $(CF_3CF_2)_2CF\text{—}$ may be mentioned.

The number of carbon atoms in the monovalent fluorinated hydrocarbon group having a fluorinated cyclic structure as $R^{f1}$ is preferably from 3 to 20, more preferably from 4 to 8, particularly preferably from 4 to 6. When the number of carbon atoms in the fluorinated hydrocarbon group is within the above range, excellent chemical resistance will be obtained, and the resulting surface layer will be more excellent in abrasion resistance and fingerprint stain removability.

The fluorinated hydrocarbon group as $R^{f1}$ is, in view of excellent chemical resistance and in that the resulting surface layer will be more excellent in sliding resistance, preferably a fluorocycloalkyl group.

The fluorinated hydrocarbon group as $R^{f1}$ is, in view of excellent chemical resistance and in that the resulting surface layer will be more excellent in abrasion resistance and fingerprint stain removability, preferably a perfluorinated hydrocarbon group.

As the fluorinated hydrocarbon group as $R^{f1}$, for example, the monovalent fluorinated cyclic structure exemplified by the above formula may be mentioned.

When the number of carbon atoms in the fluoroalkylene group as $R^{f2}$ or $R^{f4}$ is from 1 to 6, excellent chemical resistance will be obtained, and the resulting surface layer will be more excellent in abrasion resistance and fingerprint stain removability.

The fluoroalkylene group as $R^{f2}$ or $R^{f4}$ is, in view of excellent chemical resistance and in that the resulting surface layer will be more excellent in abrasion resistance and fingerprint stain removability, preferably a linear fluoroalkylene group.

The fluoroalkylene group as $R^{f2}$ or $R^{f4}$ is, in view of excellent chemical resistance and in that the resulting surface layer will be more excellent in abrasion resistance and fingerprint stain removability, preferably a perfluoroalkylene group.

The proportion of the perfluoroalkylene group in the entire $R^{f2}$ is, in view of excellent chemical resistance and in that the resulting surface layer will be more excellent in abrasion resistance and fingerprint stain removability, preferably at least 60 mol %, more preferably at least 80 mol %, particularly preferably 100 mol %.

The number of carbon atoms in the bivalent fluorinated hydrocarbon group having a fluorinated cyclic structure as $R^{f3}$ or $R^{f4}$ is preferably from 3 to 20, more preferably from 4 to 8, particularly preferably from 4 to 6. When the number of carbon atoms in the fluorinated hydrocarbon group is within the above range, excellent chemical resistance will be obtained, and the resulting surface layer will be more excellent in abrasion resistance and fingerprint stain removability.

The fluorinated hydrocarbon group as $R^{f3}$ or $R^{f4}$ is, in view of excellent chemical resistance and in that the resulting surface layer will be more excellent in sliding resistance, preferably a fluorocycloalkylene group.

The fluorinated hydrocarbon group as $R^{f3}$ or $R^{f4}$ is, in view of excellent chemical resistance and in that the resulting surface layer will be more excellent in abrasion resistance and fingerprint stain removability, preferably a perfluorinated hydrocarbon group.

As the fluorinated hydrocarbon group as $R^{f3}$ or $R^{f4}$, for example the bivalent fluorinated cyclic structure exemplified by the above formula may be mentioned.

In a case where the surface layer is required to have sufficient sliding resistance, m is preferably an integer of from 1 to 30, more preferably an integer of from 1 to 20, particularly preferably an integer of from 1 to 10. When m is at most the upper limit value of the above range, the surface layer will be more excellent in sliding resistance.

In a case where the surface layer is required to have sufficient abrasion resistance and fingerprint stain removability, m is preferably an integer of from 2 to 200, more preferably an integer o from 5 to 150, particularly preferably an integer of from 10 to 100.

When m is at least the lower limit value of the above range, excellent chemical resistance will be obtained, and the resulting surface layer will be more excellent in abrasion resistance and fingerprint stain removability. When m is at most the upper limit value of the above range, the resulting surface layer will be more excellent in abrasion resistance. That is, if the number average molecular weight of the compound (1A) or the compound (1B) is too large, the number of hydrolyzable silyl groups present per unit molecular weight decrease, thus lowering the abrasion resistance of the surface layer.

In a case where the surface layer is required to have sufficient sliding resistance, n is preferably an integer of from 1 to 200, more preferably an integer of from 1 to 150, particularly preferably an integer of from 1 to 100. When n is at most the upper limit value of the above range, excellent chemical resistance will be obtained, and the resulting surface layer will be more excellent in sliding resistance.

Further, in view of excellent chemical resistance and in that the resulting surface layer will be excellent in sliding resistance, when n is 0, it is preferred that $R^{f1}$ or $R^{f4}$ has a fluorinated cyclic structure.

When n is 1 and $R^{f1}$ or $R^{f4}$ has no fluorinated cyclic structure, or when n is 0, in view of excellent chemical resistance and in that the resulting surface layer will be excellent in sliding resistance, m is preferably an integer of from 5 to 30, more preferably an integer of from 6 to 20, particularly preferably an integer of from 7 to 10.

When n is 1 and $R^{f1}$ or $R^{f4}$ has a fluorinated cyclic structure, or when n is an integer of at least 2, in view of excellent chemical resistance and in that the resulting surface layer will be excellent in sliding resistance, m is preferably an integer of from 1 to 30, more preferably an integer of from 2 to 20, particularly preferably an integer of from 3 to 10.

As $OR^{f2}$, that is oxyfluoroalkylene units, for example, $OCHF$, $OCF_2CHF$, $OCHFCF_2$, $OCF_2CH_2$, $OCH_2CF_2$, $OCF_2CF_2CHF$, $OCHFCF_2CF_2$, $OCF_2CF_2CH_2$, $OCH_2CF_2CF_2$, $OCF_2CF_2CF_2CH_2$, $OCH_2CF_2CF_2CF_2$, $OCF_2CF_2CF_2CF_2CH_2$, $OCH_2CF_2CF_2CF_2CF_2$, $OCF_2$, $OCF_2CF_2$, $OCF_2CF_2CF_2$, $OCF(CF_3)CF_2$, $OCF_2CF_2CF_2CF_2$, $OCF(CF_3)CF_2CF_2$, $OCF_2CF_2CF_2CF_2CF_2$, and $OCF_2CF_2CF_2CF_2CF_2CF_2$ may be mentioned.

As $OR^{f3}$, for example, oxyfluorocycloalkylene units of the following formulae may be mentioned. * in the formulae represents a connecting bond.

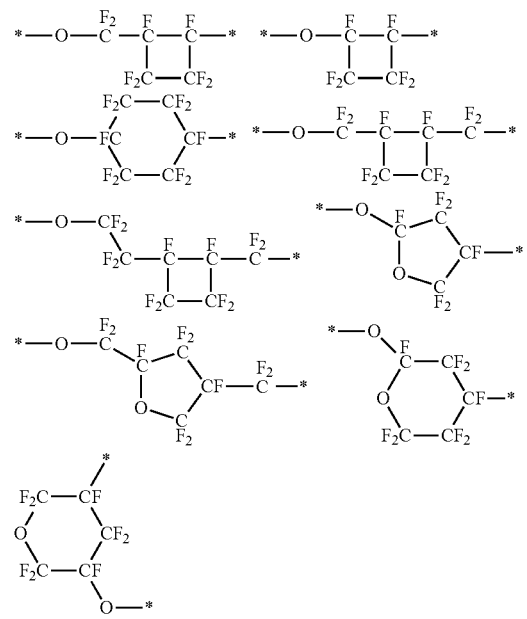

In a case where in $(OR^{f2})_m (OR^{f3})_n$, there are two or more types of oxyfluoro(cyclo)alkylene units, the bonding order of the respective oxyfluoro(cyclo)alkylene units is not limited. For example, in a case where $OCF_2CF_2$ and $OCF_2CF_2CF_2CF_2$ are present, $OCF_2CF_2$ and $OCF_2CF_2CF_2CF_2$ may be arranged randomly, alternately or in blocks. In a case where $OCF_2$ and $OCF_2CF_2$ are present, it is preferred that both are arranged randomly.

"There are two or more types of oxyfluoro(cyclo)alkylene units" means that two or more types of oxyfluoro(cyclo)alkylene units differing in the number of carbon atoms are present, that two or more types of oxyfluoro(cyclo)alkylene units differing in the number of hydrogen atoms are present, that two or more types of oxyfluoro(cyclo)alkylene units differing in the positions of hydrogen atoms are present, and that two or more types of oxyfluoro(cyclo)alkylene units having the same number of carbon atoms but differing in whether the units have a side chain or not or in the type of the side chain (the number of side chains or the number of carbon atoms in the side chain) are present.

With respect to the arrangement of the two or more types of oxyfluoro(cyclo)alkylene units, for example, a structure represented by $\{(OCF_2)_{m1}(OCF_2CF_2)_{m2}\}$ means that m1 ($OCF_2$) and m2 ($OCF_2CF_2$) are randomly arranged. Further, a structure represented by $(OCF_2CF_2\text{—}OCF_2CF_2CF_2 CF_2)_{m5}$ means that m5 ($OCF_2CF_2$) and m5 ($OCF_2CF_2CF_2CF_2$) are alternately arranged.

As $(OR^{f2})_m(OR^{f3})_n$ wherein n is 0, preferred are ones having the following structures at least in a part thereof.
$\{(OCF_2)_{m1}(OCF_2CF_2)_{m2}\}$,
$(OCF_2CF_2)_{m3}$,
$(OCF_2CF_2CF_2)_{m4}$, $(OCF_2CF_2-OCF_2CF_2CF_2CF_2)_{m5}$,
$(OCF_2CF_2CF_2CF_2CF_2)_{m6}(OCF_2)_{m7}$,
$(OCF_2CF_2CF_2CF_2CF_2)_{m6}$ $(OCF_2CF_2)_{m7}$,
$(OCF_2CF_2CF_2CF_2CF_2CF_2)_{m6}$ $(OCF_2)_{m7}$,
$(OCF_2CF_2CF_2CF_2CF_2CF_2)_{m6}(OCF_2CF_2)_{m7}$,
$(OCF_2CF_2CF_2CF_2CF_2-OCF_2)_{m8}$,
$(OCF_2CF_2CF_2CF_2CF_2-OCF_2CF_2)_{m8}$,
$(OCF_2CF_2CF_2CF_2CF_2CF_2-OCF_2)_{m8}$,
$(OCF_2CF_2CF_2CF_2CF_2CF_2-OCF_2CF_2)_{m8}$,
$(OCF_2-OCF_2CF_2CF_2CF_2CF_2)_{m8}$,
$(OCF_2-OCF_2CF_2CF_2CF_2CF_2CF_2)_{m8}$,
$(OCF_2CF_2-OCF_2CF_2CF_2CF_2CF_2)_{m8}$,
$(OCF_2CF_2-OCF_2CF_2CF_2CF_2CF_2CF_2)_{m8}$,
$(OCF(CF_3)CF_2)_{m9}$.

In the formulae, m1, m2, m3, m4, m5, m6, m7, m8 and m9 are an integer of at least 1. The upper limit values of m1, m2, m3, m4, m5, m6, m7, m8 and m9 are adjusted in accordance with the upper limit value of m.

As $(OR^{f2})_m(OR^{f3})_n$ wherein n is 0, in that the compound (1A) and the compound (1B) will readily be produced, the following are preferred.

$\{(OCF_2)_{m1}(OCF_2CF_2)_{m2}\}OCF_2$,
$(OCF_2CF_2)_{m3}OCF_2$,
$(OCF_2CF_2CF_2)_{m4}OCF_2CF_2$,
$(OCF_2CF_2)_2\{(OCF_2)_{m1}(OCF_2CF_2)_{m2}\}OCF_2$,
$(OCF_2CF_2-OCF_2CF_2CF_2CF_2)_{m5}OCF_2CF_2OCF_2CF_2CF_2$,
$(OCF_2-OCF_2CF_2CF_2CF_2CF_2)_{m8}OCF_2OCF_2CF_2CF_2CF_2$,
$(OCF_2-OCF_2CF_2CF_2CF_2CF_2CF_2)_{m8}OCF_2OCF_2CF_2CF_2CF_2CF_2$,
$(OCF_2CF_2-OCF_2CF_2CF_2CF_2CF_2)_{m8}OCF_2CF_2OCF_2CF_2CF_2CF_2$,
$(OCF_2CF_2-OCF_2CF_2CF_2CF_2CF_2CF_2)_{m8}OCF_2CF_2OCF_2CF_2CF_2CF_2CF_2$,
$(OCF(CF_3)CF_2)_{m9}OCF(CF_3)$.

As $(OR^{f2})_m(OR^{f3})_n$ wherein n is at least 1, preferred are ones having the following structures at least in a part thereof.

$(OCF_2CF_2-OCF_2CF_2CF_2CF_2)_{m11}-O(c-C_4F_6)-(OCF_2CF_2CF_2CF_2-OCF_2CF_2)_{m12}$,
$(OCF_2CF_2CF_2CF_2-O(c-C_4F_6))_{m13}$,
$(OCF_2CF_2-OCF_2CF_2CF_2CF_2CF_2CF_2)_{m14}-O(c-C_4F_6)-(OCF_2CF_2CF_2CF_2CF_2CF_2-OCF_2CF_2)_{m15}$.

In the formulae, c-$C_4F_6$ is a perfluoro-1,2-cyclobutylene group, and m11, m12, m13, m14 and m15 are an integer of at least 1. The upper limit values of m11, m12, m13, m14 and m15 are adjusted in accordance with the upper limit values of m and n.

As $(OR^{f2})_m(OR^{f3})_n$ wherein n is at least 1, in that the compound (1A) and the compound (1B) will readily be produced, the following are preferred.

$OCF_2CF_2CF_2$ $(OCF_2CF_2-OCF_2CF_2CF_2CF_2)_{m11}-O(c-C_4F_6)-(OCF_2CF_2CF_2CF_2-OCF_2CF_2)_{m12}OCF_2CF_2CF_2$,
$OCF_2CF_2(OCF_2CF_2CF_2CF_2-O(c-C_4F_6))_{m13}OCF_2CF_2CF_2$,
$O(c-C_4F_6)(OCF_2CF_2CF_2CF_2-O(c-C_4F_6))_{m13}OCF_2CF_2CF_2$,
$OCF_2CF_2CF_2$ $(OCF_2CF_2-OCF_2CF_2CF_2CF_2CF_2CF_2)_{m11}-O(c-C_4F_6)-(OCF_2CF_2CF_2CF_2CF_2CF_2-OCF_2CF_2)_{m12}OCF_2CF_2CF_2$.

$Q^1$ is a single bond, or a (a1+b1) valent linear or branched linking group. $Q^2$ is a single bond, or a b2+1 valent linear or branched linking group. The linking group is a bivalent or higher organic group.

When $Q^1$ or $Q^2$ is a single bond, the present compound has a structure having the function-imparting group T directly bonded to the polyfluoroalkylene chain ($R^f$ or $Q^f$).

$Q^1$ preferably further has, when a1+b1 is at least 3, at least one branch point (hereinafter sometimes referred to as branch point P) selected from the group consisting of C, N, Si, a cyclic structure, and a (a1+b1) valent organopolysiloxane residue. $Q^2$ preferably has, when b2+1 is at least 3, at least one branch point (hereinafter sometimes referred to as branch point P') selected from the group consisting of C, N, Si, a cyclic structure, and a b2+1 valent organopolysiloxane residue.

The cyclic structure is, in that the compound (1A) and the compound (1B) will readily be produced, and in that the resulting surface layer will be more excellent in abrasion resistance, light resistance and chemical resistance, preferably at least one member selected from the group consisting of a 3 to 8-membered alicyclic ring, a 3 to 8-membered aromatic ring, a 3 to 8-membered heterocyclic ring, and a condensed ring comprising two or more of such rings, particularly preferably any one of the following cyclic structures. The cyclic structure may have a substituent such as a halogen atom, an alkyl group (which may contain an etheric oxygen atom between carbon atoms), a cycloalkyl group, an alkenyl group, an allyl group, an alkoxy group or an oxo group (=O).

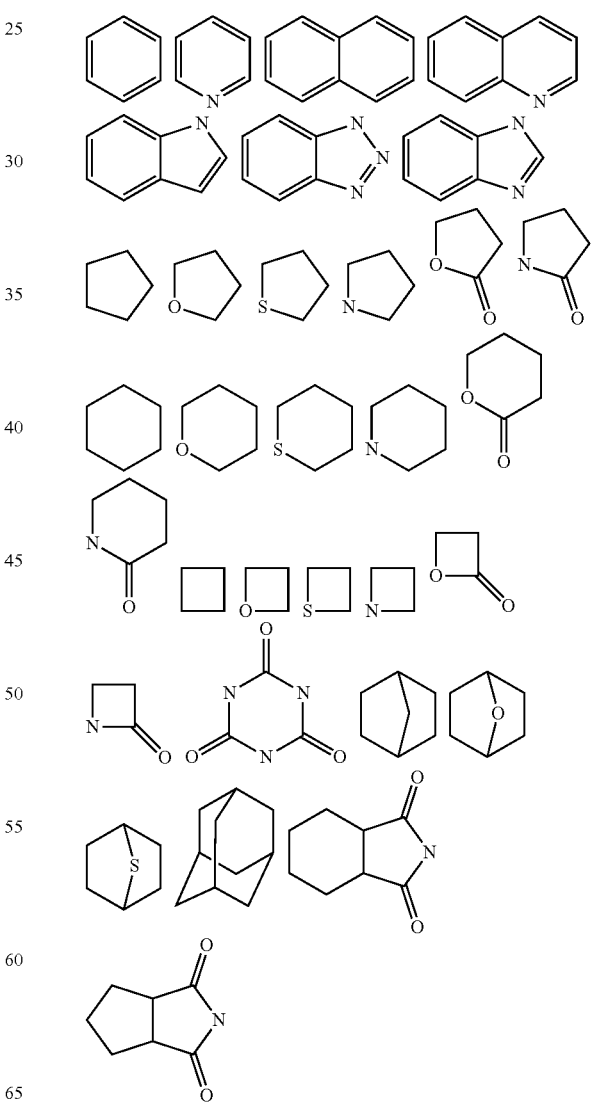

As the (a1+b1) valent organopolysiloxane residue or the b2+1 valent organopolysiloxane residue, for example, the following groups may be mentioned. In the following formulae, $R^5$ is a hydrogen atom, an alkyl group, an alkoxy group or a phenyl group. The number of carbon atoms in the alkyl group and the alkoxy group as $R^5$ is preferably from 1 to 10, particularly preferably 1.

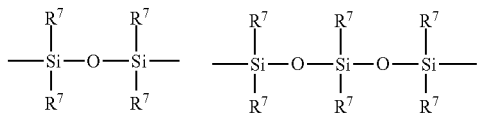

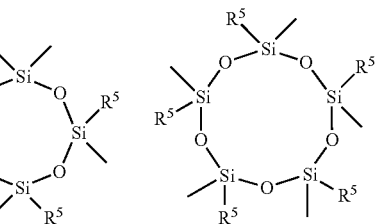

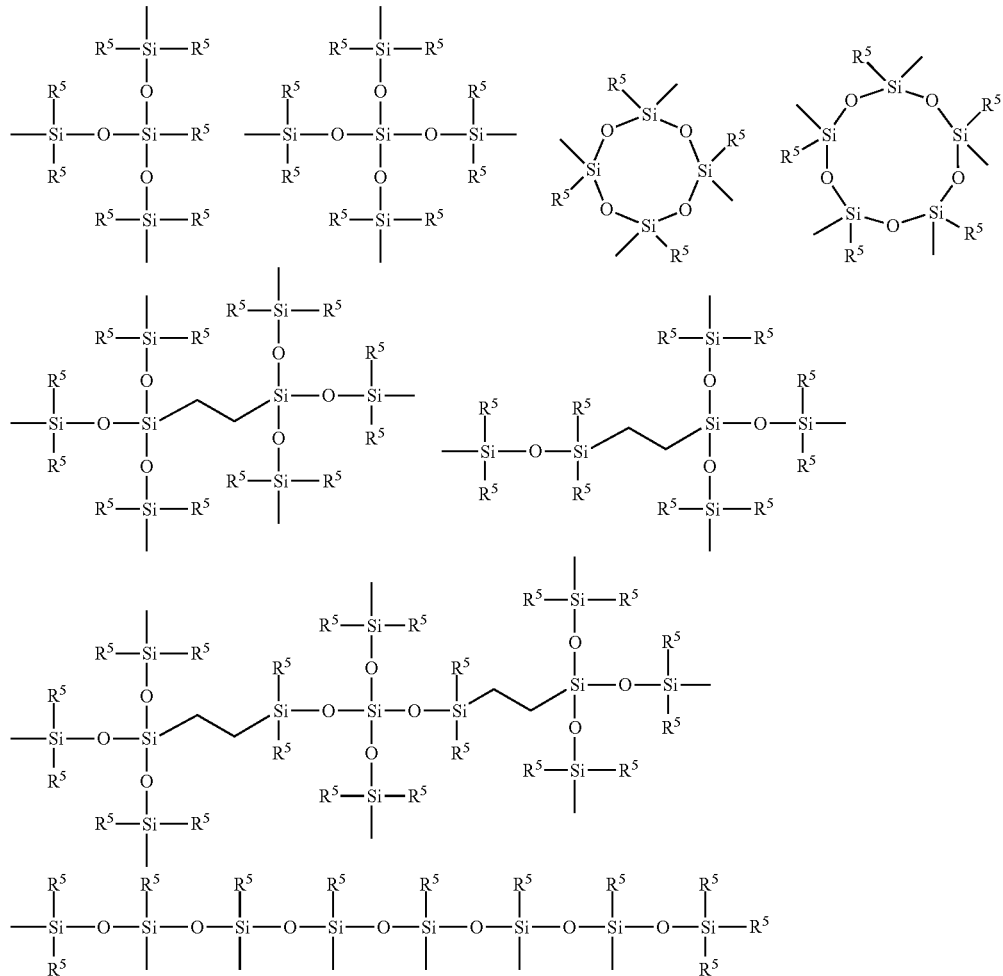

$Q^1$ and $Q^2$ may further have at least one bond (hereinafter sometimes referred to as "bond B") selected from the group consisting of —C(O)NR$^6$—, —C(O)O—, —C(O)—, —O—, —NR$^6$—, —S—, —OC(O)O—, —NHC(O)O—, —NHC(O)NR$^6$—, —SO$_2$NR$^6$—, —Si(R$^6$)$_2$—, —OSi(R$^6$)$_2$—, —Si(CH$_3$)$_2$-Ph-Si(CH$_3$)$_2$— and a bivalent organopolysiloxane residue. In the formulae, $R^6$ is a hydrogen atom, a $C_{1-6}$ alkyl group or a phenyl group, and Ph is a phenylene group. The number of carbon atoms in the alkyl group as $R^6$ is, in that the compound (1A) and the compound (1B) will readily be produced, preferably from 1 to 3, particularly preferably from 1 to 2.

As the bivalent organopolysiloxane residue, for example, the following groups may be mentioned. In the following formulae, $R^7$ is a hydrogen atom, an alkyl group, an alkoxy group or a phenyl group. The number of carbon atoms in the alkyl group or the alkoxy group as $R^7$ is preferably from 1 to 10, particularly preferably 1.

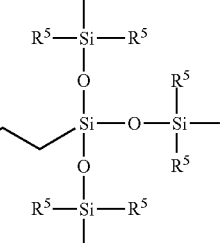

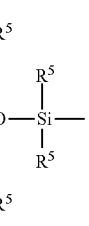

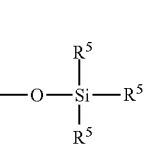

-continued

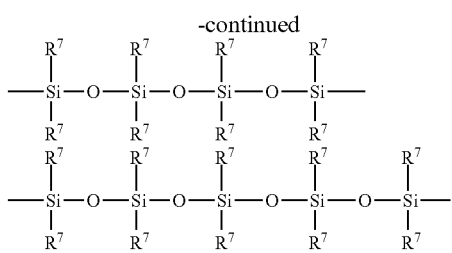

The bond B is, in that the compound (1A) and the compound (1B) will readily be produced, preferably at least one bond selected from the group consisting of —C(O)NR$^6$—, —C(O)—, —NR$^6$— and —O—, and in that the resulting surface layer will be more excellent in light resistance and chemical resistance, particularly preferably —C(O)NR$^6$— or —C(O)—.

As $Q^1$, a combination of at least two bivalent hydrocarbon groups and at least one branch point P, or a combination of at least two hydrocarbon groups, at least one branch point P' and at least one bond B may be mentioned.

As $Q^2$, a combination of at least two bivalent hydrocarbon groups and at least one branch point P', or a combination of at least two hydrocarbon groups, at least one branch point P' and at least one bond B may be mentioned.

As the bivalent hydrocarbon group, for example, a bivalent aliphatic hydrocarbon group (such as an alkylene group or a cycloalkylene group) or a bivalent aromatic hydrocarbon group (such as a phenylene group) may be mentioned. The number of carbon atoms in the bivalent hydrocarbon group is preferably from 1 to 10, more preferably from 1 to 6, particularly preferably from 1 to 4.

As the combination as $Q^1$, in that the compound (1A) will readily be produced, preferred is group (g2-1) (provided that a1=d1+d3 and b1=d2+d4), group (g2-2) (provided that a1=e1 and b1=e2), group (g2-3) (provided that a1=1 and b1=2), group (g2-4) (provided that a1=h1 and b1=h2), group (g2-5) (provided that a1=i1 and b1=i2), group (g2-6) (provided that a1=1 and b1=1), or group (g2-7) (provided that a1=1 and b1=i3).

As the combination as $Q^2$, in that the compound (1B) will readily be produced, preferred is group (g2-1) (provided that b2=d2+d4), group (g2-2) (provided that b2=e2), group (g2-3) (provided that b2=2), group (g2-4) (provided that b2=h2), group (g2-5) (provided that b2=i2), group (g2-6) (provided that b2=1), or group (g2-7) (provided that b2=i3).

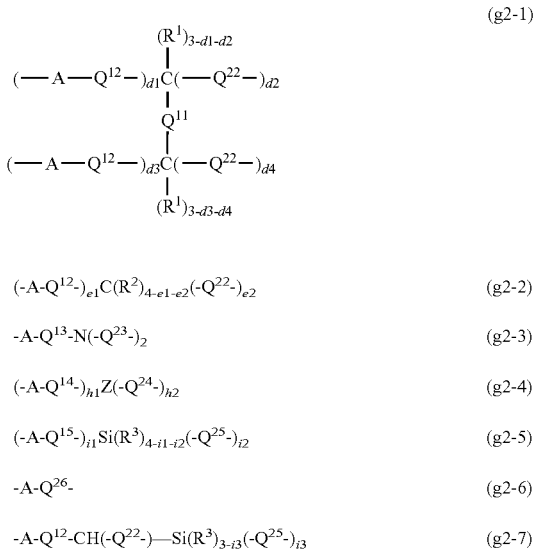

$$(-A-Q^{12}-)_{e1}C(R^2)_{4-e1-e2}(-Q^{22}-)_{e2} \quad (g2-2)$$

$$-A-Q^{13}-N(-Q^{23}-)_2 \quad (g2-3)$$

$$(-A-Q^{14}-)_{h1}Z(-Q^{24}-)_{h2} \quad (g2-4)$$

$$(-A-Q^{15}-)_{i1}Si(R^3)_{4-i1-i2}(-Q^{25}-)_{i2} \quad (g2-5)$$

$$-A-Q^{26}- \quad (g2-6)$$

$$-A-Q^{12}-CH(-Q^{22}-)-Si(R^3)_{3-i3}(-Q^{25}-)_{i3} \quad (g2-7)$$

In the formulae (g2-1) to (g2-7), the A side is bonded to $R^f$ or $Q^f$, and the $Q^{22}$, $Q^{23}$, $Q^{24}$, $Q^{25}$ and $Q^{26}$ side is bonded to T. A is a single bond, —C(O)NR$^6$—, —C(O)—, —OC(O)O—, —NHC(O)O—, —NHC(O)NR$^6$—, —O— or —SO$_2$NR$^6$Q$^{11}$ is a single bond, —O—, an alkylene group, or a group having —C(O)NR$^6$—, —C(O)—, —NR$^6$— or —O— between carbon atoms of an alkylene group having at least 2 carbon atoms. $Q^{12}$ is a single bond, an Oalkylene group, or a group having —C(O)NR$^6$—, —C(O)—, —NR$^6$— or —O— between carbon atoms of an alkylene group having at least 2 carbon atoms, and when $Q^1$ or $Q^2$ has two or more $Q^{12}$, the two or more $Q^{12}$ may be the same or different. $Q^{13}$ is a single bond (provided that A is —C(O)—), an alkylene group, a group having —C(O)NR$^6$—, —C(O)—, —NR$^6$— or —O— between carbon atoms of an alkylene group having at least 2 carbon atoms, or an alkylene group having —C(O)— at the terminal on the N side. $Q^{14}$ is $Q^{12}$ when the atom in Z to which $Q^{14}$ is bonded is a carbon atom, or $Q^{13}$ when the atom in Z to which $Q^{14}$ is bonded is a nitrogen atom, and when $Q^1$ or $Q^2$ has two or more $Q^{14}$, the two or more $Q^{14}$ may be the same or different. $Q^{15}$ is an alkylene group, or a group having —C(O)NR$^6$—, —C(O)—, —NR$^6$— or —O— between carbon atoms of an alkylene group having at least 2 carbon atoms, and when $Q^1$ or $Q^2$ has two or more $Q^{15}$, the two or more $Q^{15}$ may be the same or different. $Q^{22}$ is an alkylene group, a group having —C(O)NR$^6$—, —C(O)—, —NR$^6$— or —O— between carbon atoms of an alkylene group having at least 2 carbon atoms, an alkylene group having —C(O)NR$^6$—, —C(O)—, —NR$^6$— or —O— at the terminal on the side not bonded to T, or a group having —C(O)NR$^6$—, —C(O)—, —NR$^6$— or —O— between carbon atoms of an alkylene group having at least 2 carbon atoms and having —C(O)NR$^6$—, —C(O)—, —NR$^6$— or —O— at the terminal on the side not bonded to T, and when $Q^1$ or $Q^2$ has two or more $Q^{22}$, the two or more $Q^{22}$ may be the same or different.

$Q^{23}$ is an alkylene group, or a group having —C(O)NR$^6$—, —C(O)—, —NR$^6$— or —O— between carbon atoms of an alkylene group having at least 2 carbon atoms, and the two $Q^{23}$ may be the same or different. $Q^{24}$ is $Q^{22}$ when the atom in Z to which $Q^{24}$ is bonded is a carbon atom, or $Q^{23}$ when the atom in Z to which $Q^{24}$ is bonded is a nitrogen atom, and when $Q^1$ or $Q^2$ has two or more $Q^{24}$, the two or more $Q^{24}$ may be the same or different. $Q^{25}$ is an alkylene group, or a group having —C(O)NR$^6$—, —C(O)—, —NR$^6$— or —O— between carbon atoms of an alkylene group having at least 2 carbon atoms, and when $Q^1$ or $Q^2$ has two or more $Q^{25}$, the two or more $Q^{25}$ may be the same or different. $Q^{26}$ is an alkylene group, or a group having —C(O)NR$^6$—, —C(O)—, —NR$^6$— or —O— between carbon atoms of an alkylene group having at least 2 carbon atoms.

Z is a group having a (a1+b1) valent or (b2+1) valent cyclic structure having a carbon atom or a nitrogen atom to which $Q^{14}$ is directly bonded and having a carbon atom or a nitrogen atom to which $Q^{24}$ is directly bonded. $R^1$ is a hydrogen atom or an alkyl group, and when $Q^1$ or $Q^2$ has two or more $R^1$, the two or more $R^1$ may be the same or different. $R^2$ is a hydrogen atom, a hydroxy group, an alkyl group or an acyloxy group. $R^3$ is an alkyl group. $R^6$ is a hydrogen atom, a $C_{1-6}$ alkyl group or a phenyl group. d1 is an integer of from 0 to 3, preferably 1 or 2.

d2 is an integer of from 0 to 3, preferably 1 or 2. d1+d2 is an integer of from 1 to 3. d3 is an integer of from 0 to 3, preferably 0 or 1. d4 is an integer of from 0 to 3, preferably 2 or 3. d3+d4 is an integer of from 1 to 3. d1+d3 is an integer of from 1 to 5, preferably 1 or 2 in $Q^1$, and 1 in $Q^2$. d2+d4 is an integer of from 1 to 5, preferably 4 or 5 in $Q^1$, and is an integer of from 3 to 5, preferably 4 or 5 in $Q^2$. e1+e2 is 3 or 4. e1 is an integer of from 1 to 3, preferably 1 or 2 in $Q^1$, and 1 in $Q^2$. e2 is an integer of from 1 to 3, preferably 2 or 3 in $Q^1$, and 2 or 3 in $Q^2$. h1 is an integer of at least 1, preferably 1 or 2 in $Q^1$, and 1 in $Q^2$.

h2 is an integer of at least 1, preferably 2 or 3. i1+i2 is 3 or 4. i1 is an integer of from 1 to 3 in $Q^1$, preferably 1 or 2, and 1 in $Q^2$. i2 is an integer of from 1 to 3, preferably 2 or 3 in $Q^1$, and, 2 or 3 in $Q^2$. i3 is 2 or 3.

The number of carbon atoms in the alkylene group as each of $Q^{11}$, $Q^{12}$, $Q^{13}$, $Q^{14}$, $Q^{15}$, $Q^{22}$, $Q^{23}$, $Q^{24}$, $Q^{25}$ and $Q^{26}$ is, in that the compound (1A) and the compound (1B) will readily be produced, and in that the resulting surface layer will be more excellent in abrasion resistance, light resistance and chemical resistance, preferably from 1 to 10, more preferably from 1 to 6, particularly preferably from 1 to 4, provided that when the alkylene group has a specific bond between carbon atoms, the lower limit value of the number of carbon atoms in such an alkylene group is 2.

As the cyclic structure in Z, the above described cyclic structure may be mentioned, and the preferred embodiments are also the same.

Since $Q^{14}$ and $Q^{24}$ are directly bonded to the cyclic structure in Z, $Q^{14}$ and $Q^{24}$ will not be connected to, for example, an alkylene group connected to the cyclic structure.

The number of carbon atoms in the alkyl group as $R^1$, $R^2$ and $R^3$ is, in that the compound (1A) and the compound (1B) will readily be produced, preferably from 1 to 6, more preferably from 1 to 3, particularly preferably from 1 to 2.

The number of carbon atoms in the alkyl group moiety in the acyloxy group as $R^2$ is, in that the compound 1 will readily be produced, preferably from 1 to 6, more preferably from 1 to 3, particularly preferably from 1 to 2.

h1 is, in that the compound (1A) and the compound (1B) will readily be produced, and in that the resulting surface layer will be more excellent in abrasion resistance and fingerprint stain removability, preferably from 1 to 6, more preferably from 1 to 4, further preferably from 1 or 2, particularly preferably 1.

h2 is, in that the compound (1A) and the compound (1B) will readily be produced, and in that the resulting surface layer will be more excellent in abrasion resistance and fingerprint stain removability, preferably from 2 to 6, more preferably from 2 to 4, particularly preferably 2 or 3.

As other embodiment of $Q^1$, group (g2-8) (provided that a1=d1+d3 and b1=the total of k), group (g2-9) (provided that a1=e1 and b1=e2), group (g2-10) (provided that a1=1 and b1=the total of k), group (g2-11) (provided that a1=h1 and b1=the total of k), group (g2-12) (provided that a1=i1 and b1=the total of k), group (g2-13) (provided that a1=1 and b1=k), and group (g2-14) (provided that a1=1 and b1=the total of k) may be mentioned.

As other embodiment of $Q^2$, group (g2-8) (provided that b2=the total of k), group (g2-9) (provided that b2=e2), group (g2-10) (provided that b2=the total of k), group (g2-11) (provided that b2=the total of k), group (g2-12) (provided that b2=the total of k), group (g2-13) (provided that b2=k), and group (g2-14) (provided that b2=the total of k) may be mentioned.

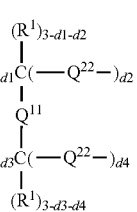  (g2-8)

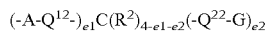 (g2-9)

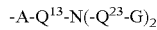 (g2-10)

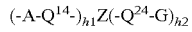 (g2-11)

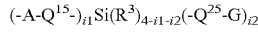 (g2-12)

 (g2-13)

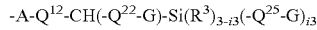 (g2-14)

In the formulae (g2-8) to (g2-14), the A side is bonded to $R^f$ or $Q^f$, and the G side is bonded to T. G is group (g3), and the two or more G in $Q^1$ or $Q^2$ may be the same or different. Reference symbols other than G are the same as the reference symbols in the formulae (g2-1) to (g2-7).

 (g3)

In the formula (g3), the Si side is bonded to $Q^{22}$, $Q^{23}$, $Q^{24}$, $Q^{25}$ or $Q^{26}$, and the $Q^3$ side is bonded to T. $R^8$ is an alkyl group. $Q^3$ is an alkylene group, a group having —C(O)NR$^6$—, —C(O)—, —NR$^6$— or —O— between carbon atoms of an alkylene group having at least 2 carbon atoms, or —(OSi(R$^9$)$_2$)$_p$—O—, the two or more $Q^3$ may be the same or different, k is 2 or 3. $R^6$ is a hydrogen atom, a $C_{1-6}$ alkyl group or a phenyl group. $R^9$ is an alkyl group, a phenyl group or an alkoxy group, and the two $R^9$ may be the same or different, p is an integer of from 0 to 5, and when p is at least 2, the two or more (OSi(R$^9$)$_2$) may be the same or different.

The number of carbon atoms in the alkylene group as $Q^3$ is, in that the compound (1A) and the compound (1B) will readily be produced, and in that the resulting surface layer will be more excellent in abrasion resistance, light resistance and chemical resistance, preferably from 1 to 10, more preferably from 1 to 6, particularly preferably from 1 to 4, provided that when the alkylene group has a specific bond between carbon atoms, the lower limit value of the number of carbon atoms in such an alkylene group is 2.

The number of carbon atoms in the alkyl group as $R^8$ is, in that the compound (1A) and the compound (1B) will readily be produced, preferably from 1 to 6, more preferably from 1 to 3, particularly preferably from 1 to 2.

The number of carbon atoms in the alkyl group as $R^9$ is, in that the compound (1A) and the compound (1B) will readily be produced, preferably from 1 to 6, more preferably from 1 to 3, particularly preferably from 1 to 2.

The number of carbon atoms in the alkoxy group as $R^9$ is, in that the compound (1A) and the compound (1B) are excellent in storage stability, preferably from 1 to 6, more preferably from 1 to 3, particularly preferably from 1 to 2.

p is preferably 0 or 1.

T is a function-imparting group which imparts various functions to the present compound. Such functions may, for example, be a function to improve the adhesion to the substrate surface, a function to impart photo-curing property or heat curing property to the present compound, a function to impart acidity or alkalinity to the present compound, a function to adjust the solubility of the present compound in a specific solvent, and a function as a reactive group to prepare other compound using the present compound as a material.

The fluoroalkyl group as $R^{f6}$ and $R^{10}$ preferably has from 1 to 6 carbon atoms. The fluoroalkyl group may have other substituent. The present compound having the fluoroalkyl group as T is a compound having a high fluorine content and is excellent in various properties such as low refractive index, low dielectric constant, water/oil repellency, heat resistance, chemical resistance, chemical stability, and transparency. As the substituent which the fluoroalkyl group may have, a halogen atom such as a fluorine atom or a chlorine atom, a $C_{1-6}$ alkyl group, and the same group exemplified as the function-imparting group T may be mentioned.

The aryl group as Ar or $R^{10}$ may, for example be a phenyl group or a naphthyl group, and may further have a substituent. As the substituent which the aryl group may have, a halogen atom such as a fluorine atom or a chlorin atom, a $C_{1-6}$ alkyl group, and the same group exemplified as the function-imparting group T may be mentioned.

The alkyl group as $R^{10}$ preferably has from 1 to 6 carbon atoms. The alkyl group may have other substituent. As the substituent which the alkyl group may have, a halogen atom such as a chlorin atom, a $C_{1-6}$ alkyl group, and the same group exemplified as the function-imparting group T may be mentioned.

The present compound having as T a hydroxy group, a N-hydroxy group, an aldehyde group, a ketone group, an amino group, a quaternary ammonium group, a nitrile group, an imino group, a diazo group, a carboxy group, a carboxylate, an acid anhydride group, a sulfo group, a sulfonate, a phosphoric acid group or a phosphate, has, by the function-imparting group T, various properties such as acidity, alkalinity or hydrophilicity imparted, and for example, has a function imparted such that the solubility in a specific solvent is improved or adhesion to a specific substrate is improved. The counter ion of the quaternary ammonium salt may, for example, be a halide ion. The counter ion of the carboxylate, the sulfate and the phosphate may, for example, be an alkali metal ion or an ammonium ion.

The group having a carbon-carbon double bond may, for example, be a vinyl group, an acryloyloxy group, a methacryloyloxy group, or an olefin. With the present compound having a carbon-carbon double bond, in combination with a photo initiator or the like, a photocurable composition can be prepared, and a cured coating film obtained by the composition has both water/oil repellency and hard coat property.

Further, with the present compound having an isocyanate group, an epoxy group, a glycidyl group, an oxetanyl group or a mercapto group, in combination with an epoxy curing agent, a thermosetting or photocurable composition can be prepared, and a cured coating film obtained by the composition has both water/oil repellency and hard coat property.

An amide bond, an ester bond, an ether bond, a thioether bond, a siloxane bond and a urea bond in T are bonds linking an alkyl group, a fluoroalkyl group, an aryl group, a heteroaryl group and the like contained in T. T may further have other function-imparting group via such a bond.

The function-imparting group T in the present compound is, in view of synthesis, chemical stability, adhesion to a substrate, etc., preferably a hydroxy group, an amino group or a group having a carbon-carbon double bond. Among groups having a carbon-carbon double bond, an acryloyl group, a methacryloyl group, a vinyl group, an allyl group, and an olefin are preferred.

Further, when the present compound is used as a surface treatment agent to form a surface layer excellent in durability such as abrasion resistance, T is preferably a group having a reactive silyl group. The group having a reactive silyl group is preferably —Si(R)$_{3-c}$(L)$_c$, wherein a1 is an integer of at least 1, b1 is an integer of at least 1, R is an alkyl group, L is a hydrolyzable group or a hydroxy group, the two or more L in T may be the same or different, and c is 2 or 3.

The number of carbon atoms in the alkyl group as R is, in that the compound (1A) and the compound (1B) will readily be produced, preferably from 1 to 6, more preferably from 1 to 3, particularly preferably from 1 to 2.

As the hydrolyzable group as L, the same group as the above-described hydrolyzable group may be mentioned, and the preferred embodiments are also the same.

c is, in that the surface layer will have stronger adhesion to a substrate, particularly preferably 3.

Two or more T in the compound (1A) and the compound (1B) may be the same or different. In that the compound (1A) and the compound (1B) will readily be produced, they are preferably the same group.

As specific examples of T, the following structures may be mentioned. In the formulae, $R^a$ is an alkyl, fluoroalkyl or aryl group which may have a substituent, $R^b$ is a fluoroalkyl or aryl group which may have a substituent, and * represents a connecting bond.

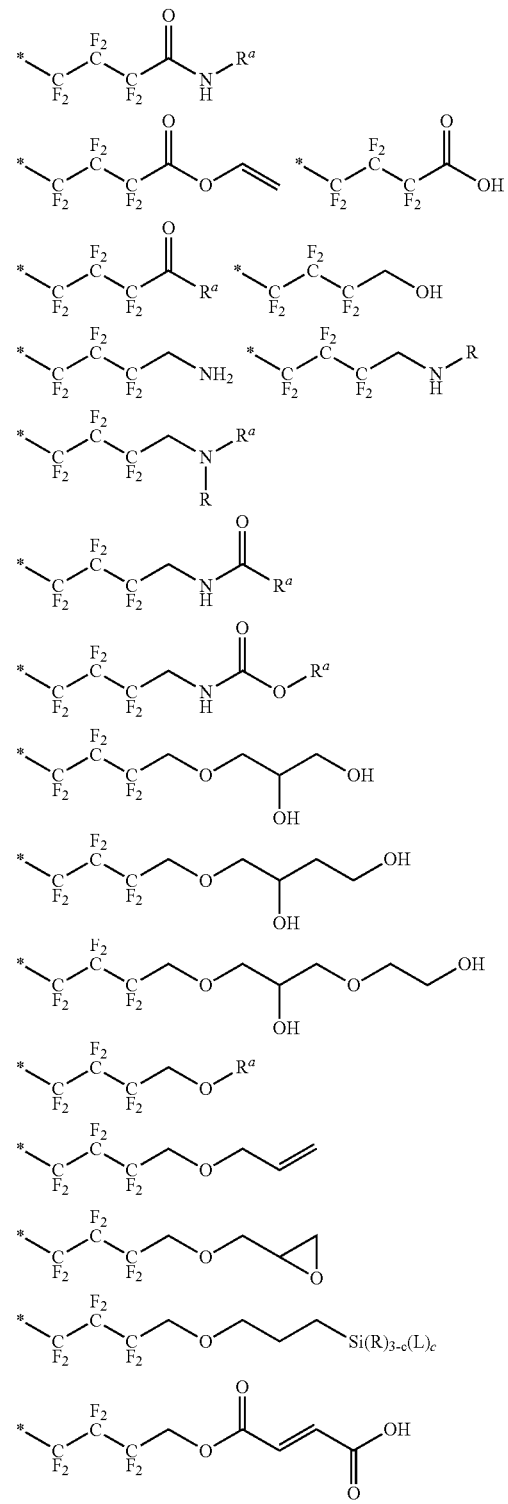

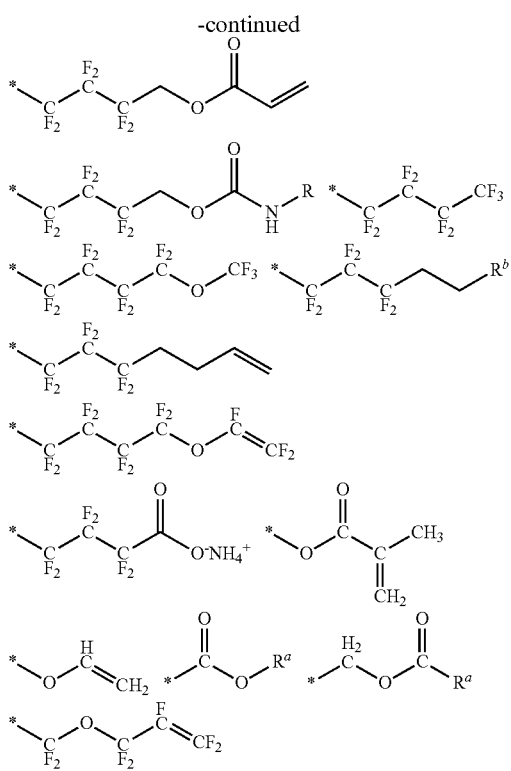

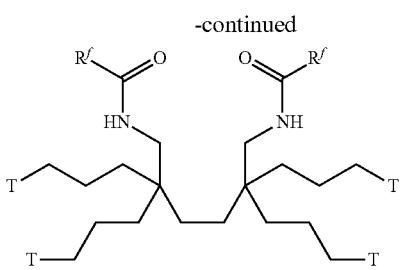

As the compound (1A) wherein $Q^1$ is group (g2-2), the following compounds may, for example, be mentioned.

As the compound (1A) and the compound (1B), for example, the following compounds may be mentioned. The following compounds are industrially readily produced, are easy to handle, are capable of forming a surface layer more excellent in water/oil repellency, abrasion resistance, fingerprint stain removability, lubricity, chemical resistance, light resistance and chemical resistance, particularly excellent in light resistance. $R^f$, $Q^f$ and T in the compounds of the following formulae are the same as $R^f$ in the above-described formula (1A) or $Q^f$ in the formula 2A, and the preferred embodiments are also the same.

As the compound (1A) wherein $Q^1$ is group (g2-1), the following compounds may, for example, be mentioned.

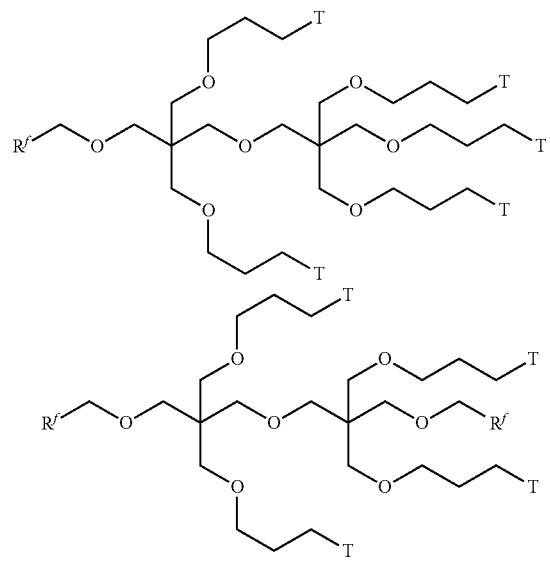

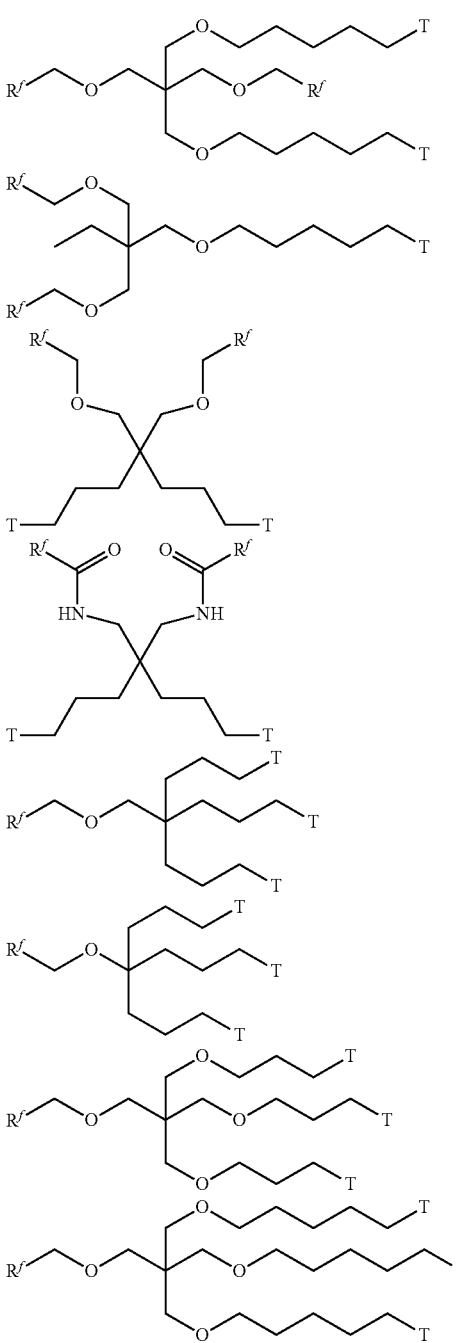

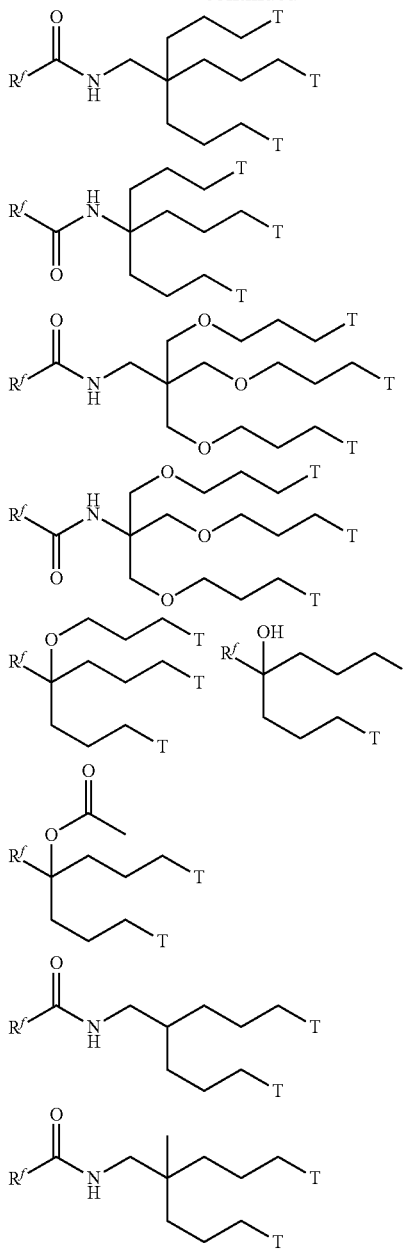
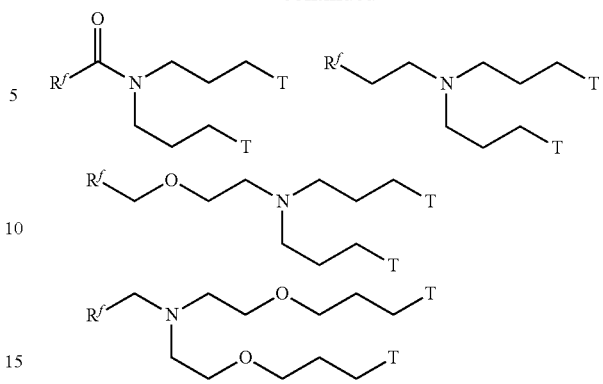
As the compound (1A) wherein $Q^1$ is group (g2-4), the following compounds may, for example, be mentioned.
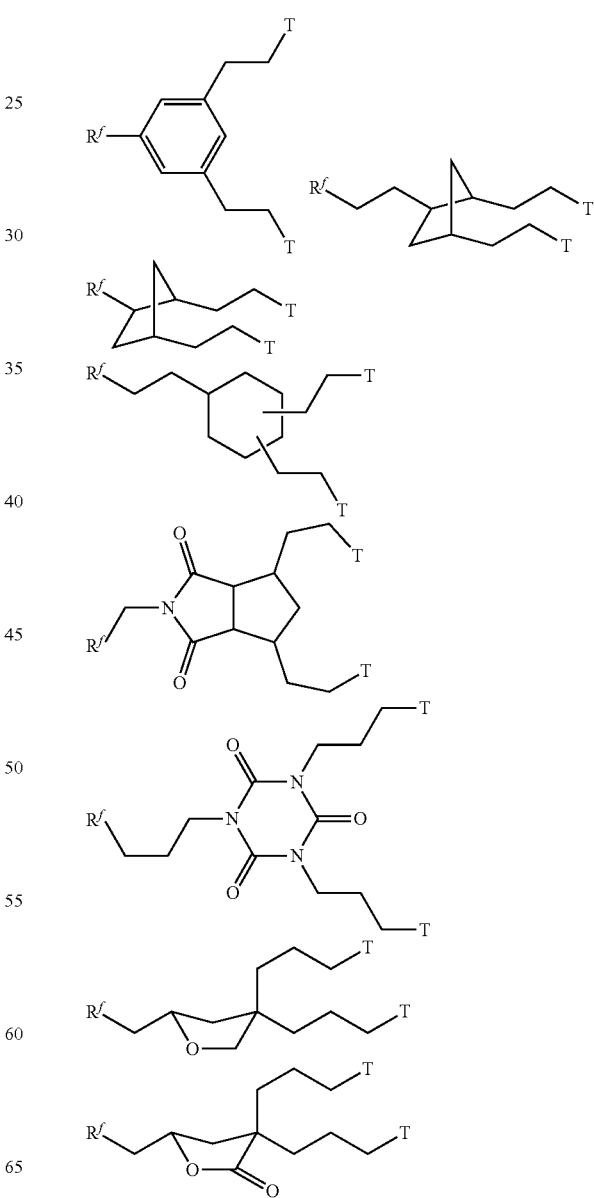
As the compound (1A) wherein $Q^1$ is group (g2-3), the following compounds may, for example, be mentioned.

-continued

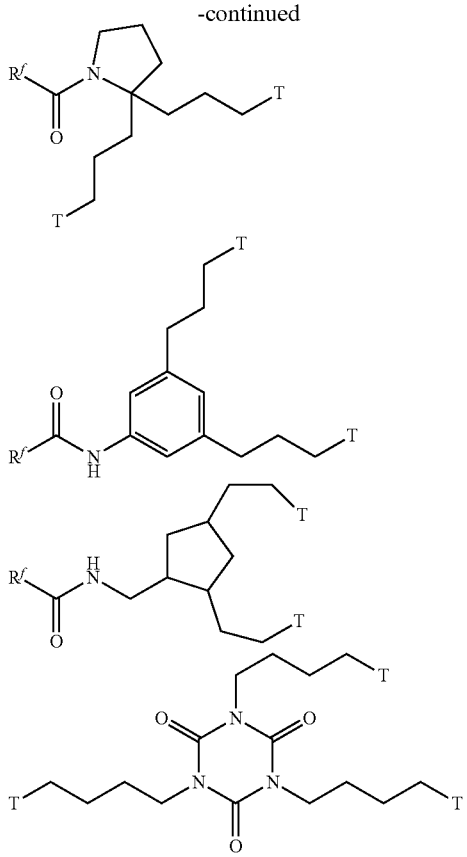

As the compound (1A) wherein $Q^1$ is group (g2-5), the following compounds may, for example, be mentioned.

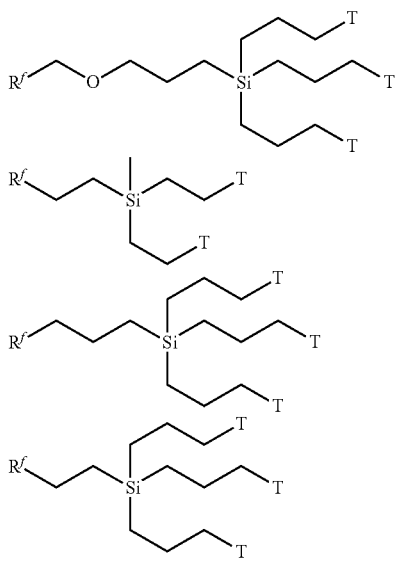

As the compound (1A) wherein $Q^1$ is group (g2-6), the following compounds may, for example, be mentioned.

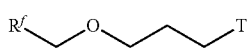

-continued

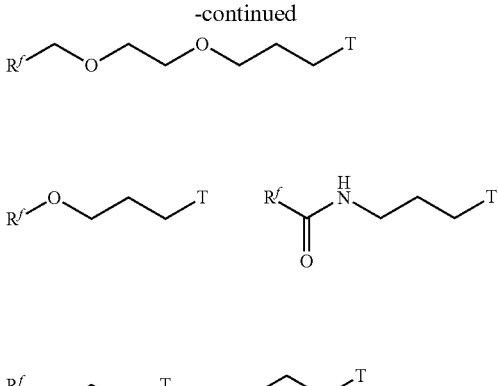

As the compound (1A) wherein $Q^1$ is group (g2-7), the following compounds may, for example, be mentioned.

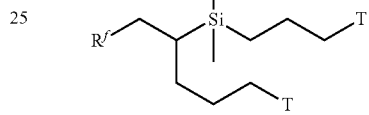

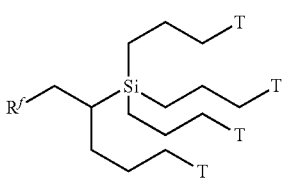

As the compound (1A) wherein $Q^1$ is group (g2-8), the following compounds may, for example, be mentioned.

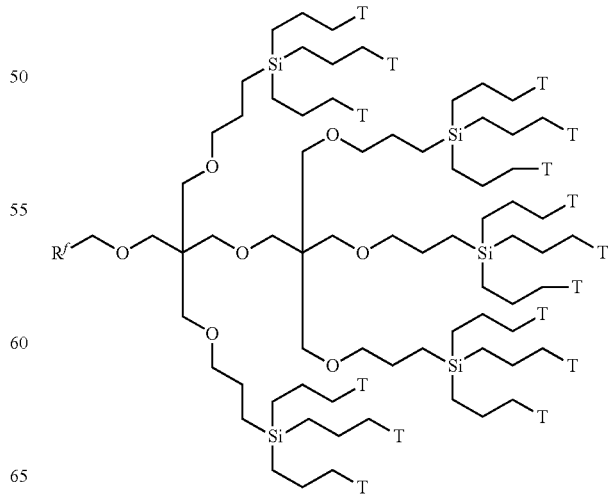

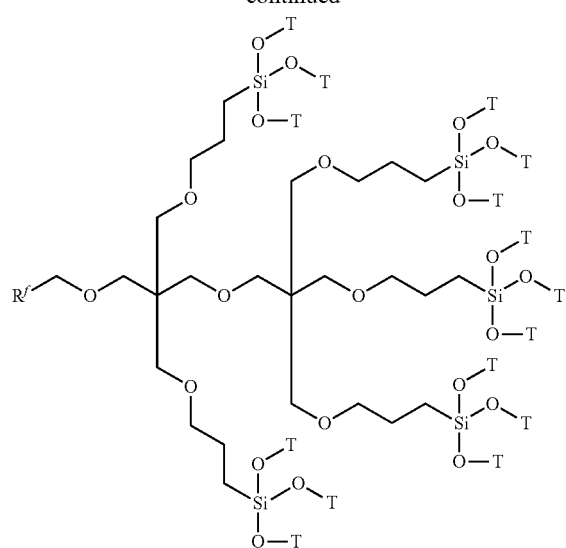
As the compound (1A) wherein Q¹ is group (g2-9), the following compounds may, for example, be mentioned.
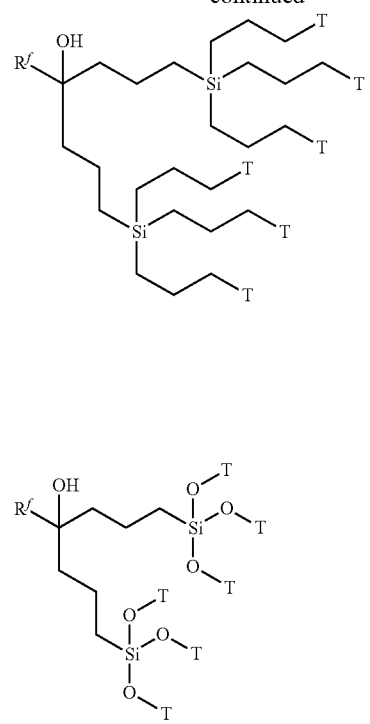
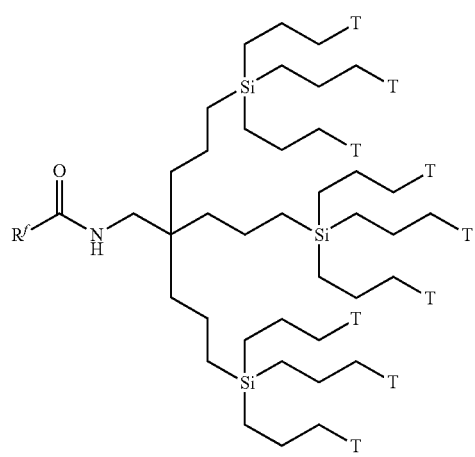
As the compound (1A) wherein Q¹ is group (g2-10), the following compounds may, for example, be mentioned.
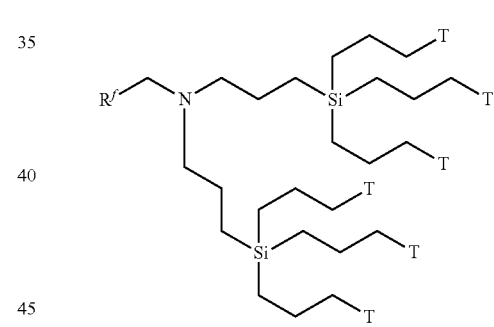
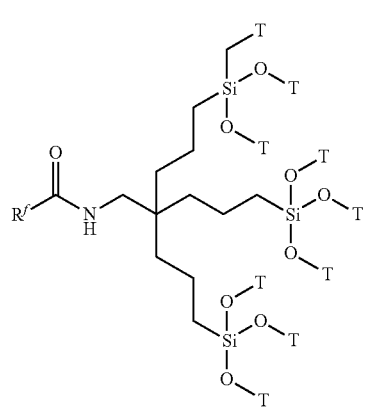
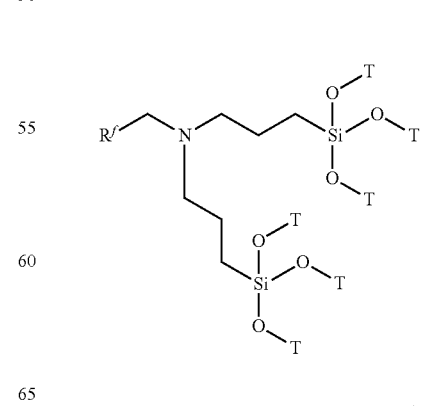
As the compound (1A) wherein Q¹ is group (g2-11), the following compounds may, for example, be mentioned.

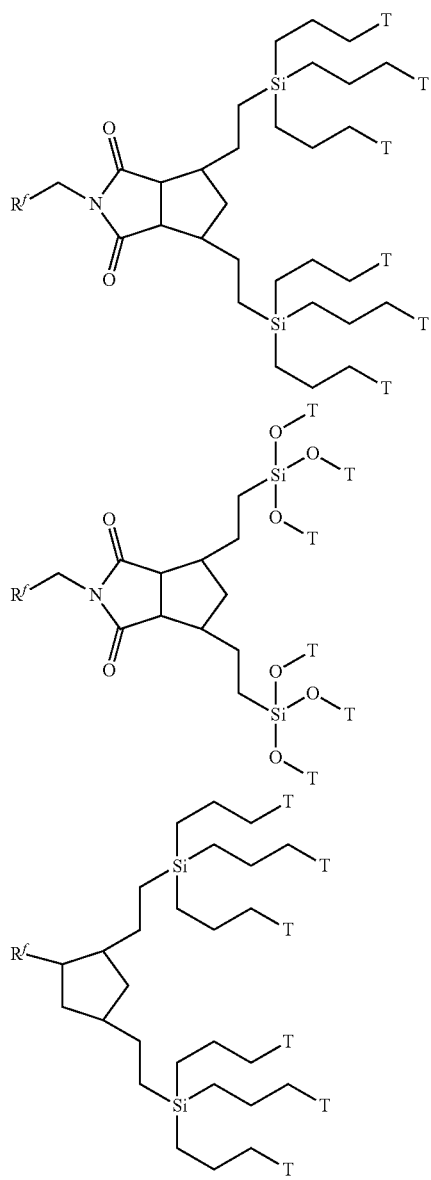
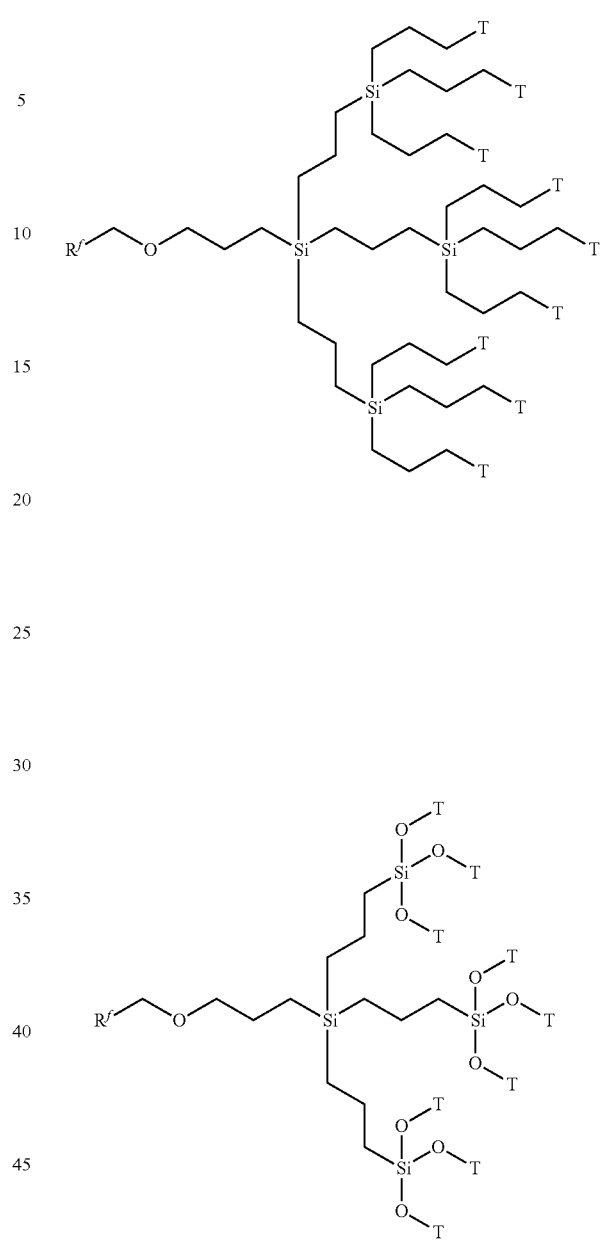
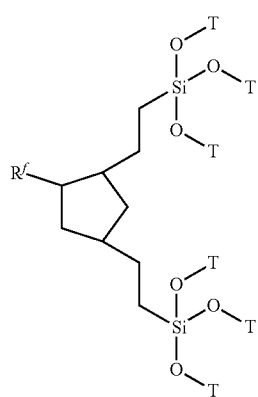
As the compound (1A) wherein $Q^1$ is group (g2-12), the following compounds may, for example, be mentioned.
As the compound (1A) wherein $Q^1$ is group (g2-13), the following compounds may, for example, be mentioned.
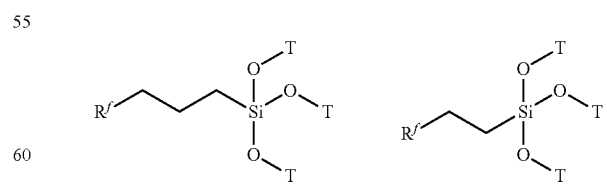
As the compound (1A) wherein $Q^1$ is group (g2-14), the following compounds may, for example, be mentioned.

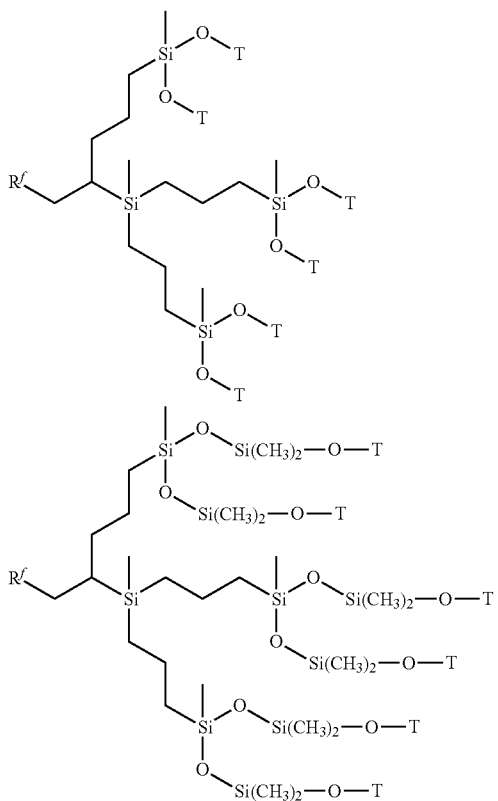

As the compound (1B) wherein $Q^2$ is group (g2-1), the following compound may, for example, be mentioned.

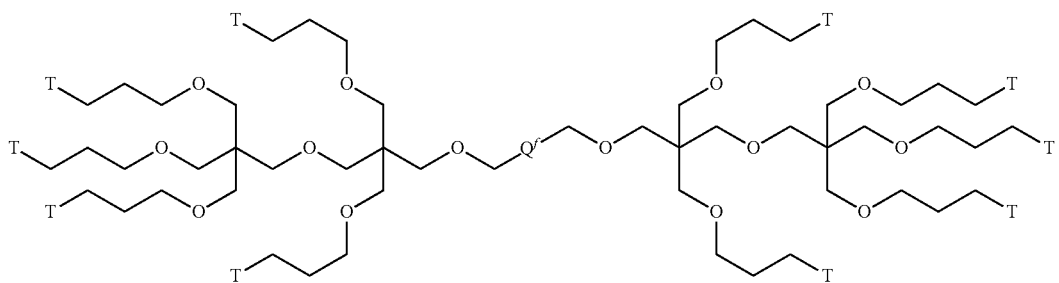

As the compound (1B) wherein $Q^2$ is group (g2-2), the following compounds may, for example, be mentioned.

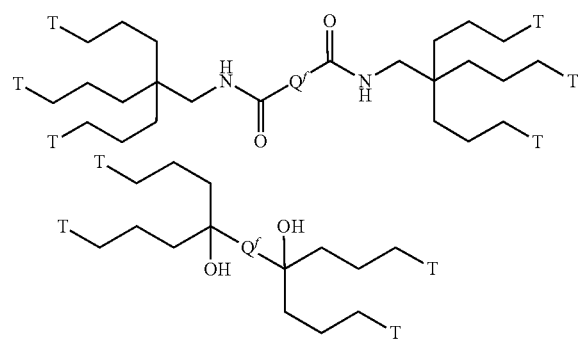

As the compound (1B) wherein $Q^2$ is group (g2-3), the following compound may, for example, be mentioned.

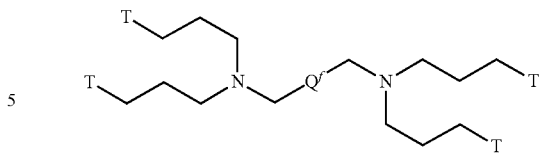

As the compound (1B) wherein $Q^2$ is group (g2-4), the following compound may, for example, be mentioned.

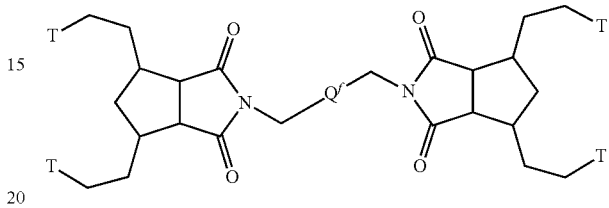

As the compound (1B) wherein $Q^2$ is group (g2-5), the following compound may, for example, be mentioned.

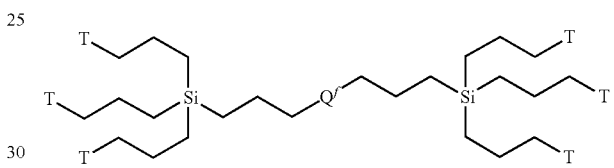

As the compound (1B) wherein $Q^2$ is group (g2-6), the following compound may, for example, be mentioned.

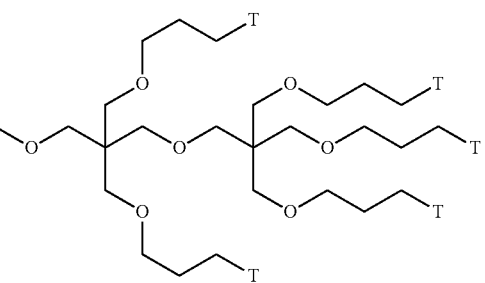

As the compound (1B) wherein $Q^2$ is group (g2-7), the following compound may, for example, be mentioned.

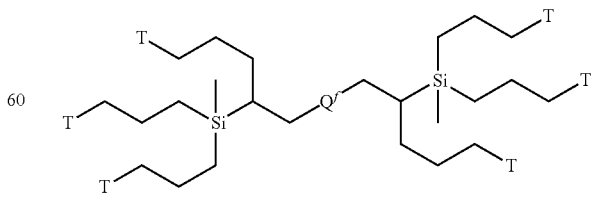

As the compound (1B) wherein $Q^2$ is group (g2-9), the following compounds may, for example, be mentioned.

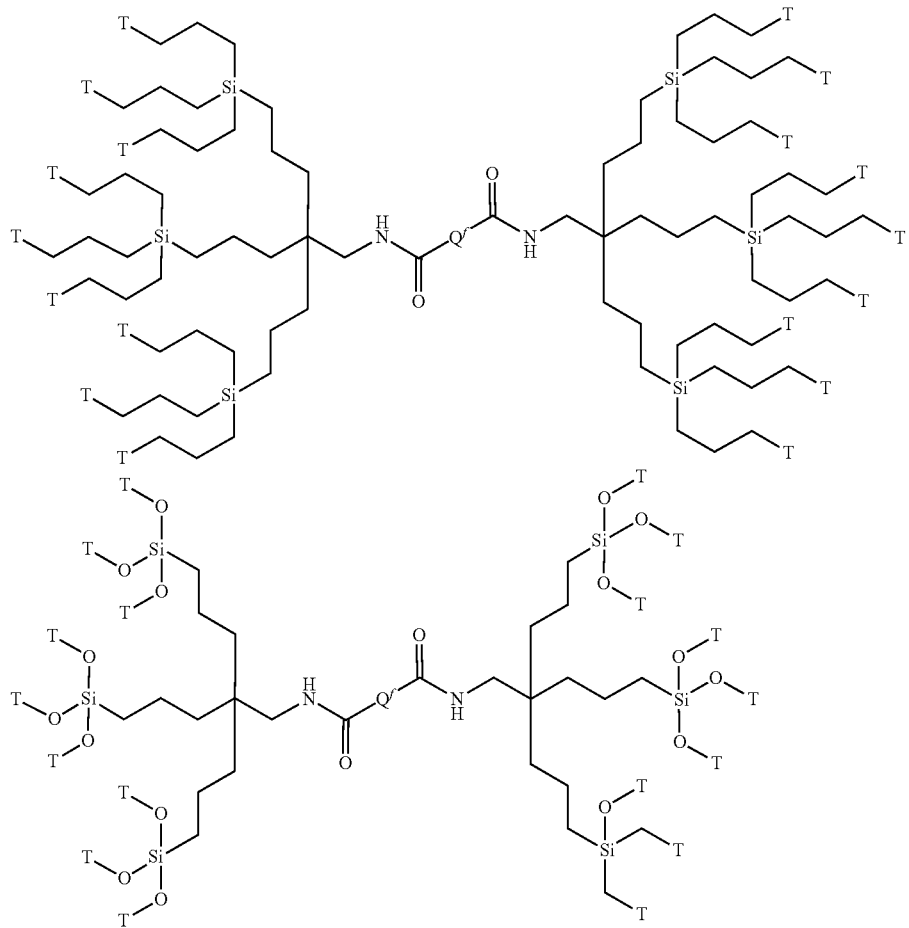

With the present compound wherein T is —Si(R)$_{3-c}$(L)$_c$ (hereinafter sometimes referred to as "the present compound having a reactive silyl group") according to an embodiment of the present invention, a surface layer excellent in fingerprint stain removability, abrasion resistance and sliding resistance can be formed.

The present compound having a reactive silyl group has a polyfluoropolyether chain, a reactive silyl group, and a specific linking group connecting the polyfluoropolyether chain and the reactive silyl group.

The polyfluoropolyether chain is preferably monovalent or bivalent. That is, the present compound may be a compound having a structure "monovalent polyfluoropolyether chain-linking group-reactive silyl group", or may be a compound having a structure "reactive silyl group-linking group-bivalent polyfluoropolyether chain-linking group-reactive silyl group".

The present compound having a reactive silyl group has the polyfluoropolyether chain. The present compound having the polyfluoropolyether chain provides a surface layer excellent in fingerprint stain removability.

The present compound having a reactive silyl group has a reactive silyl group at least at one terminal. The present compound having a reactive silyl group at its terminal is strongly chemically bonded to a substrate, whereby the resulting surface layer will be excellent in abrasion resistance.

Further, the present compound having a reactive silyl group is preferably a compound having a reactive silyl group at only one terminal. The compound having a reactive silyl group at only one terminal is less likely to aggregate, whereby the resulting surface layer will be excellent in outer appearance. Further, the surface layer will be excellent also in abrasion resistance and fingerprint stain removability.

The reactive silyl group is a group having either one or both of a hydrolyzable group and a hydroxy group bonded to the silicon atom.

The hydrolyzable group is a group converted to a hydroxy group by hydrolysis reaction. That is, the hydrolyzable silyl group becomes a silanol group (Si—OH) by hydrolysis reaction. Silanol groups will further undergo intermolecular dehydration condensation reaction to form Si—O—Si bonds. Further, a silanol group will undergo dehydration condensation reaction with a hydroxy group (substrate-OH) on the surface of a substrate to form a chemical bond (substrate-O—Si).

The hydrolyzable group may, for example, be an alkoxy group, a halogen atom, an acyl group or an isocyanate group. The alkoxy group is preferably a $C_{1-6}$ alkoxy group.

The halogen atom is preferably a chlorine atom.

The hydrolyzable group is, in that the present compound will readily be produced, preferably an alkoxy group or a halogen atom. The hydrolyzable group is, in that outgassing at the time of coating is small and the present compound will be excellent in storage stability, preferably a $C_{1-4}$ alkoxy group, and in a case where the present compound is required to have long-term storage stability, particularly preferably an ethoxy group, and in a case where the reaction time after coating is to be short, particularly preferably a methoxy group.

The structure of the present compound having a reactive silyl group other than T is the same as one described for the above present compound, and preferred structures are also the same.

Now, specific examples of the present compound having a reactive silyl group will be described.

As the compound (1A) wherein $Q^1$ is group (g2-1), the following compounds may, for example, be mentioned.

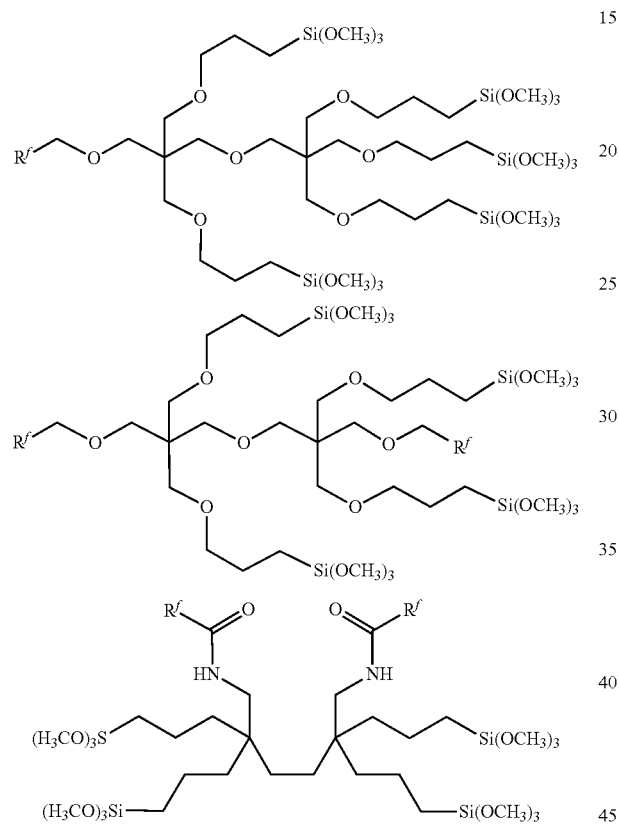

As the compound (1A) wherein $Q^1$ is group (g2-2), the following compounds may, for example, be mentioned.

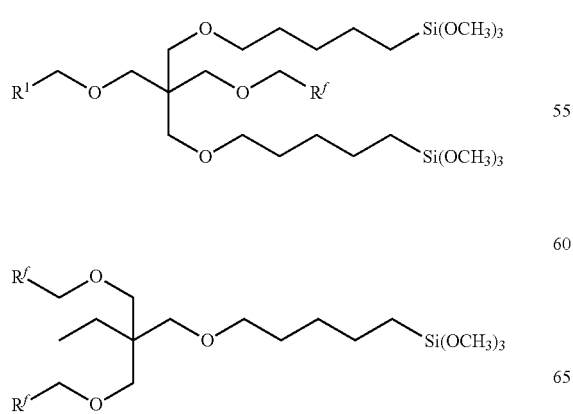

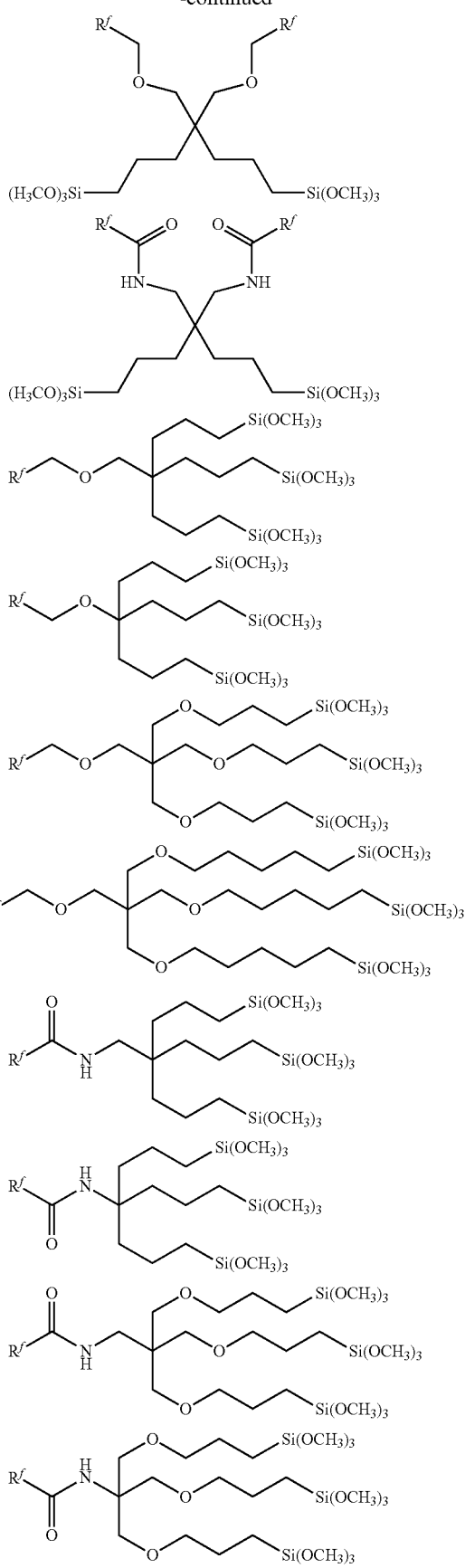

49
-continued
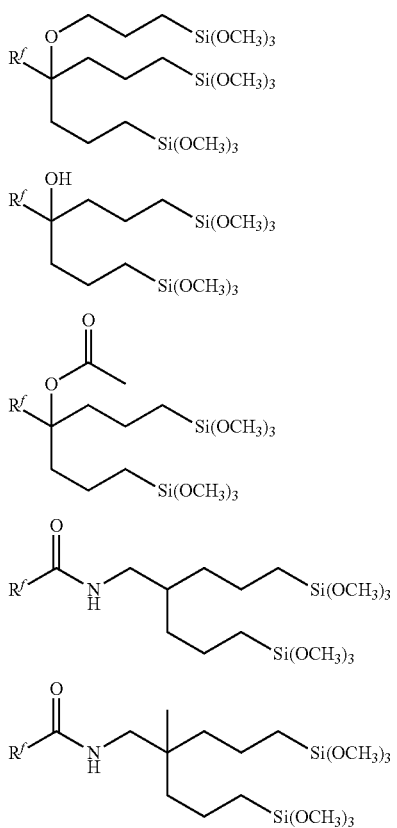
As the compound (1A) wherein $Q^1$ is group (g2-3), the following compounds may, for example, be mentioned.
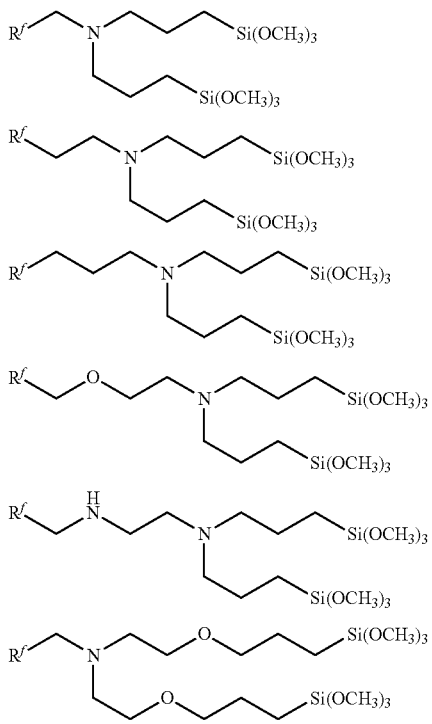
50
-continued
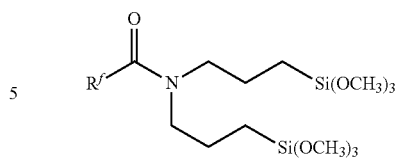
As the compound (1A) wherein $Q^1$ is group (g2-4), the following compounds may, for example, be mentioned.
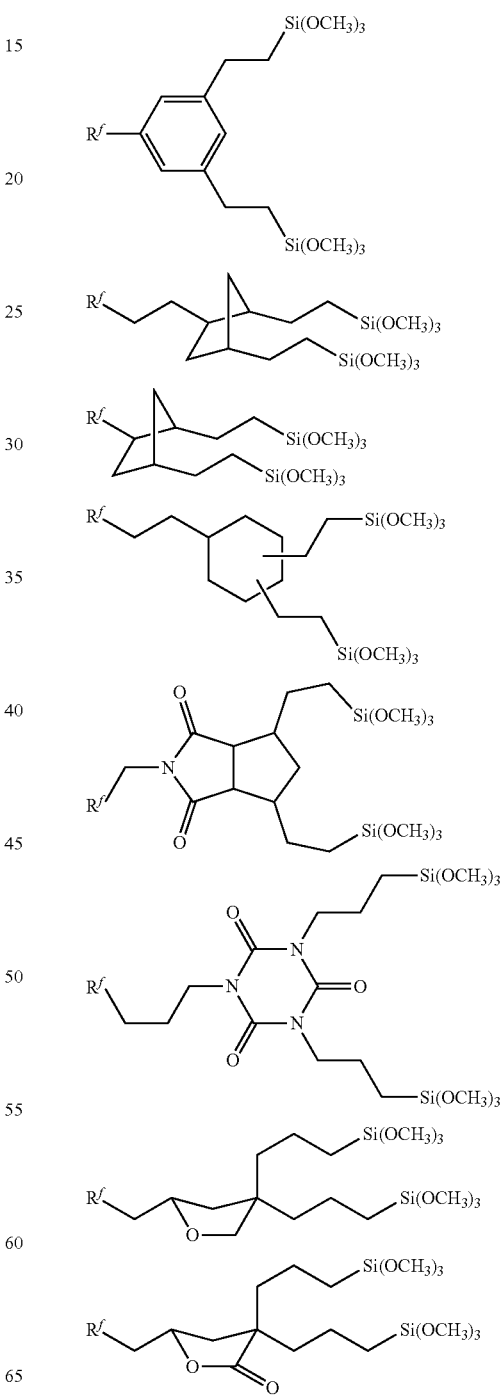

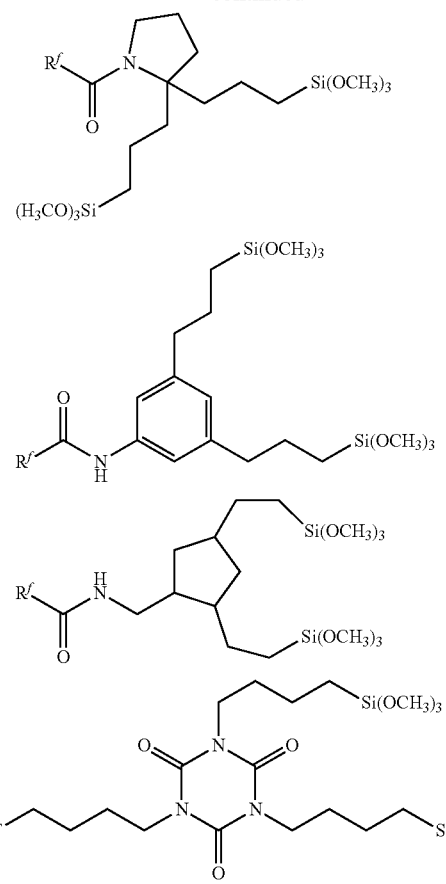

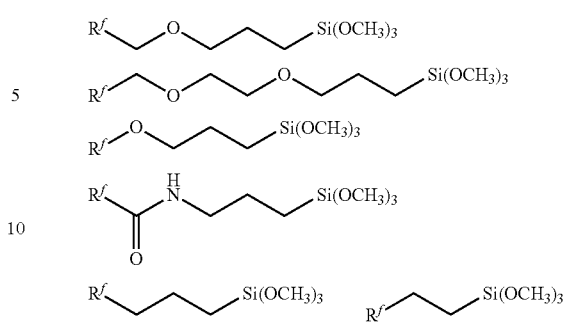

As the compound (1A) wherein $Q^1$ is group (g2-7), the following compounds may, for example, be mentioned.

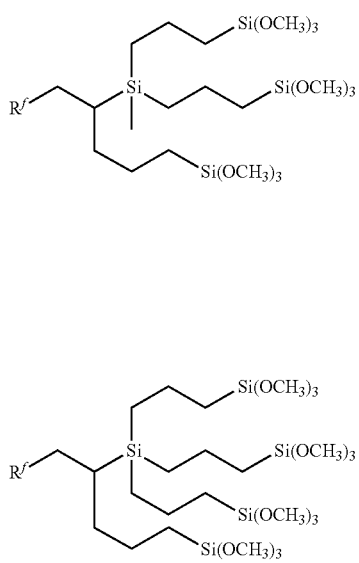

As the compound (1A) wherein $Q^1$ is group (g2-8), the following compounds may, for example, be mentioned.

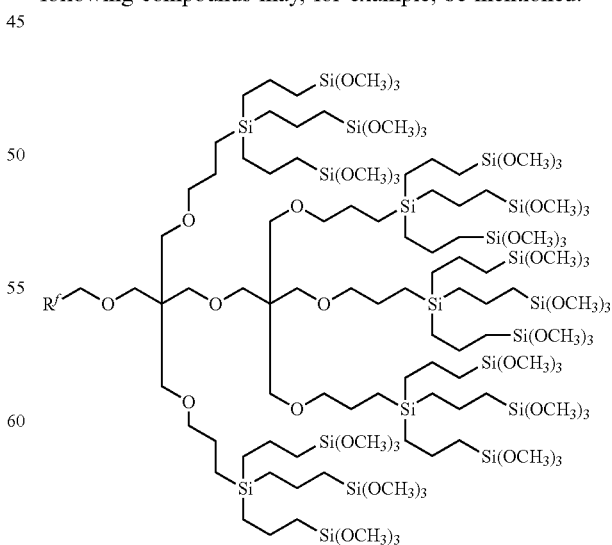

As the compound (1A) wherein $Q^1$ is group (g2-5), the following compounds may, for example, be mentioned.

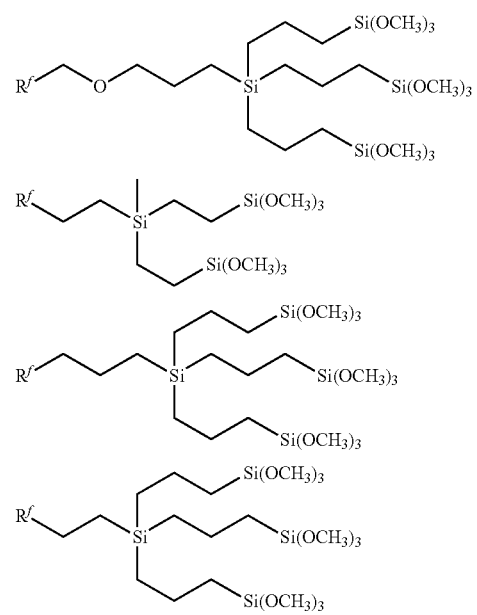

As the compound (1A) wherein $Q^1$ is group (g2-6), the following compounds may, for example, be mentioned.

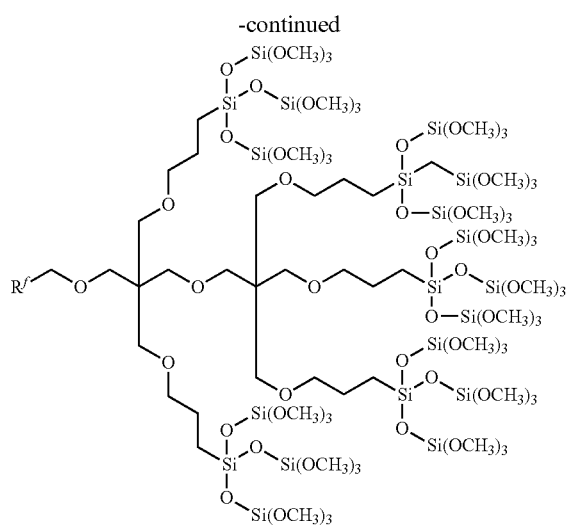
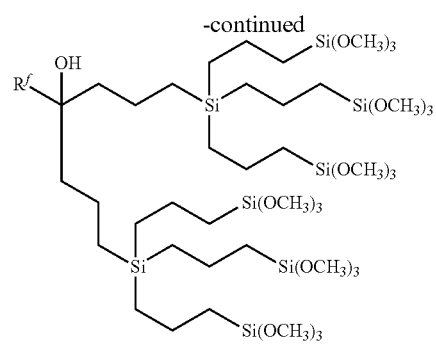
As the compound (1A) wherein $Q^1$ is group (g2-9), the following compounds may, for example, be mentioned.
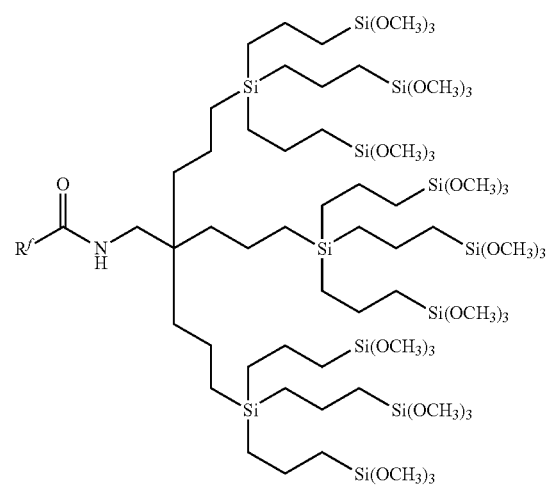
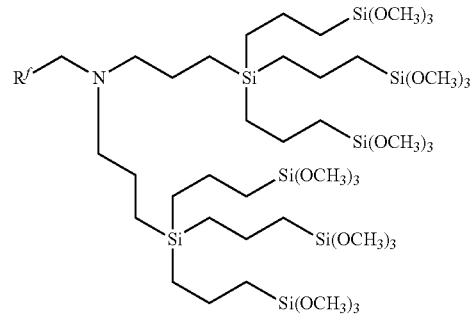
As the compound (1A) wherein $Q^1$ is group (g2-10), the following compounds may, for example, be mentioned.
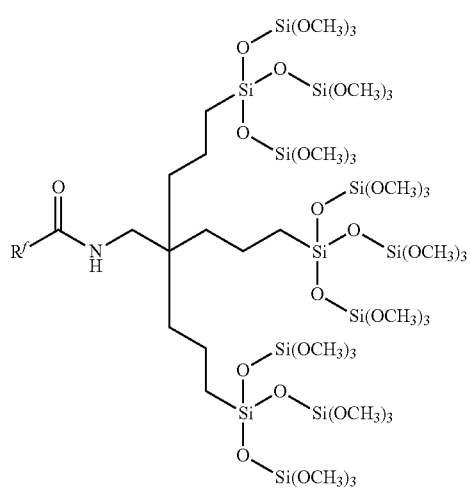
As the compound (1A) wherein $Q^1$ is group (g2-11), the following compounds may, for example, be mentioned.

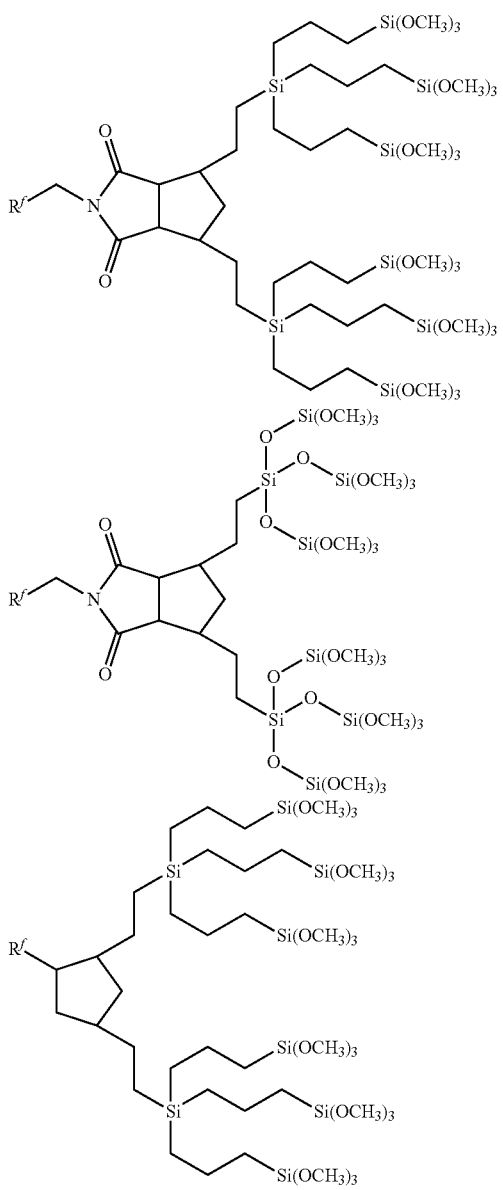
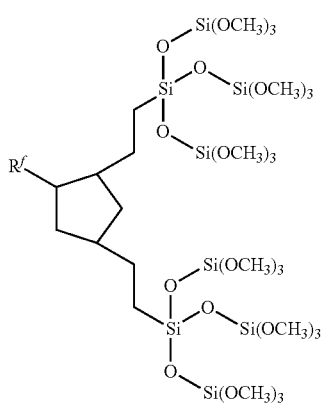
As the compound (1A) wherein $Q^1$ is group (g2-12), the following compound may, for example, be mentioned.
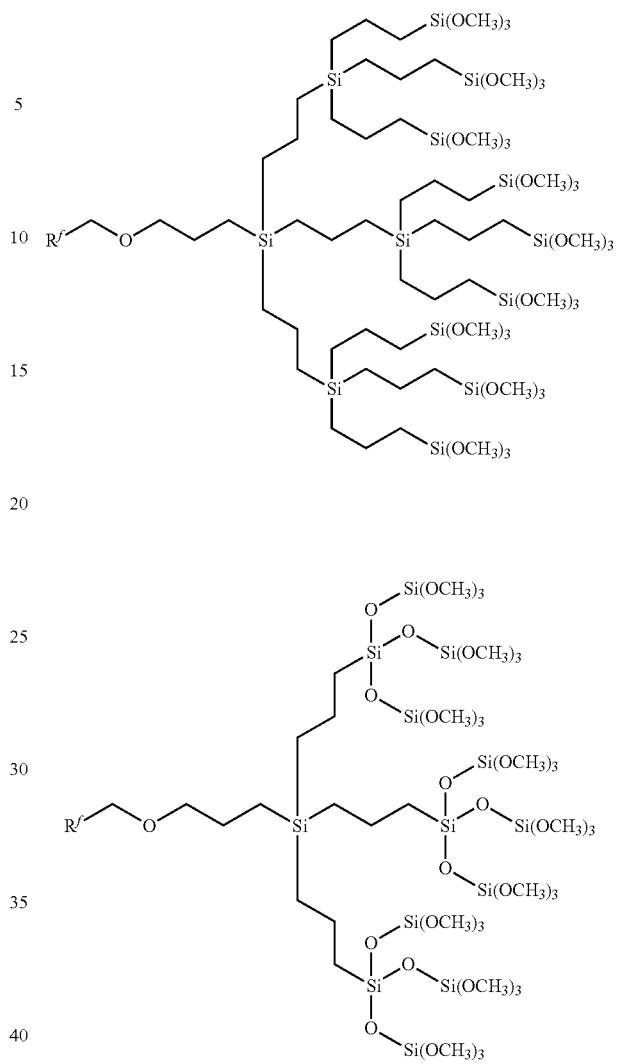
As the compound (1A) wherein $Q^1$ is group (g2-13), the following compounds may, for example, be mentioned.
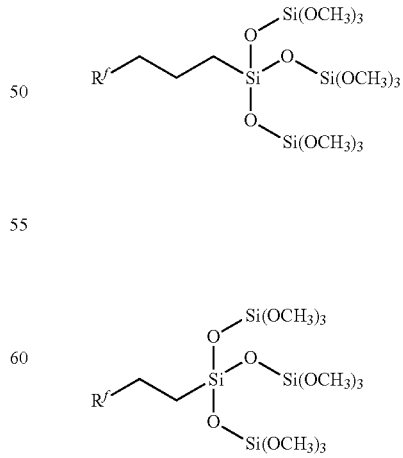
As the compound (1A) wherein $Q^1$ is group (g2-14), the following compounds may, for example, be mentioned.

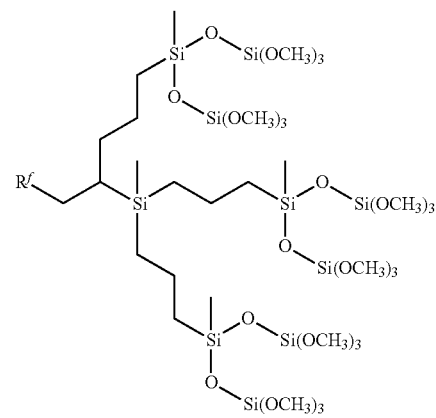

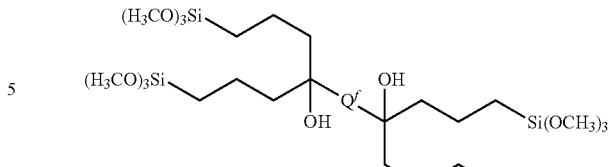

As the compound (1B) wherein $Q^2$ is group (g2-3), the following compound may, for example, be mentioned.

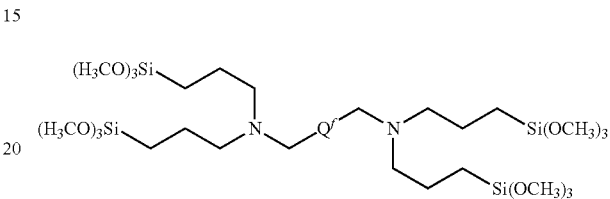

As the compound (1B) wherein $Q^2$ is group (g2-4), the following compound may, for example, be mentioned.

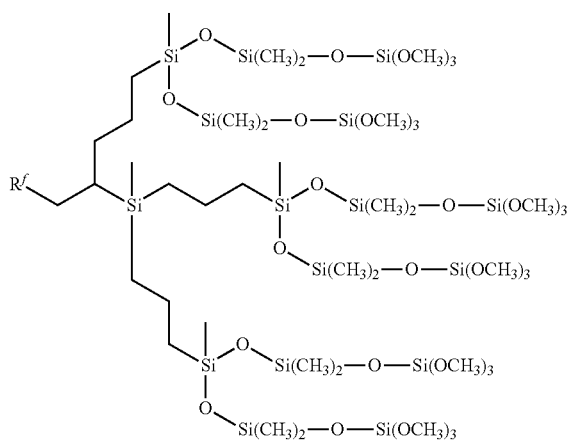

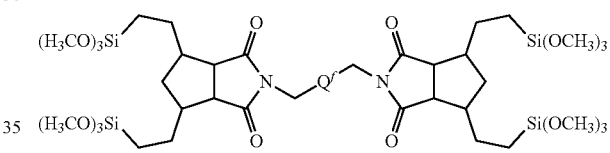

As the compound (1B) wherein $Q^2$ is group (g2-1), the following compounds may, for example, be mentioned.

As the compound (1B) wherein $Q^2$ is group (g2-5), the following compound may, for example, be mentioned.

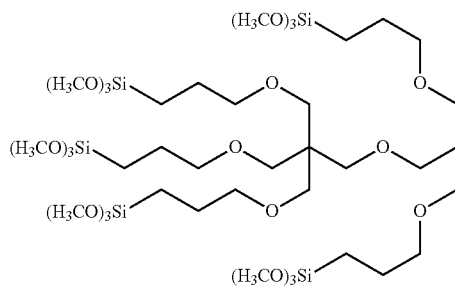

As the compound (1B) wherein $Q^2$ is group (g2-2), the following compounds may, for example, be mentioned.

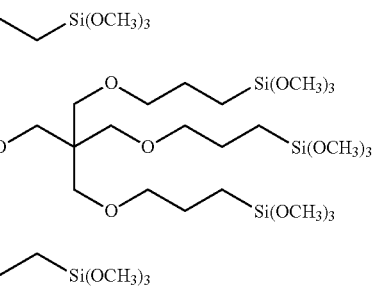

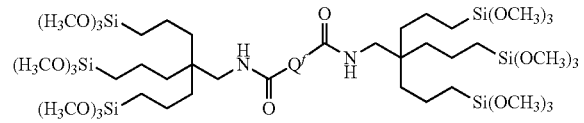

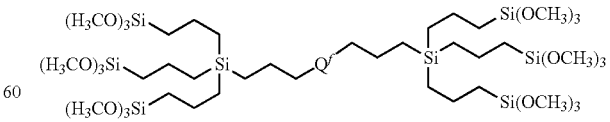

As the compound (1B) wherein $Q^2$ is group (g2-6), the following compound may, for example, be mentioned.

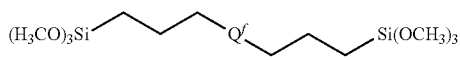

As the compound (1B) wherein Q² is group (g2-7), the following compound may, for example, be mentioned.

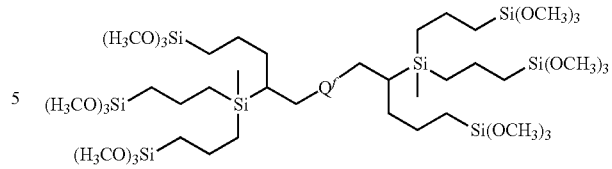

As the compound (1B) wherein Q² is group (g2-9), the following compounds may, for example, be mentioned.

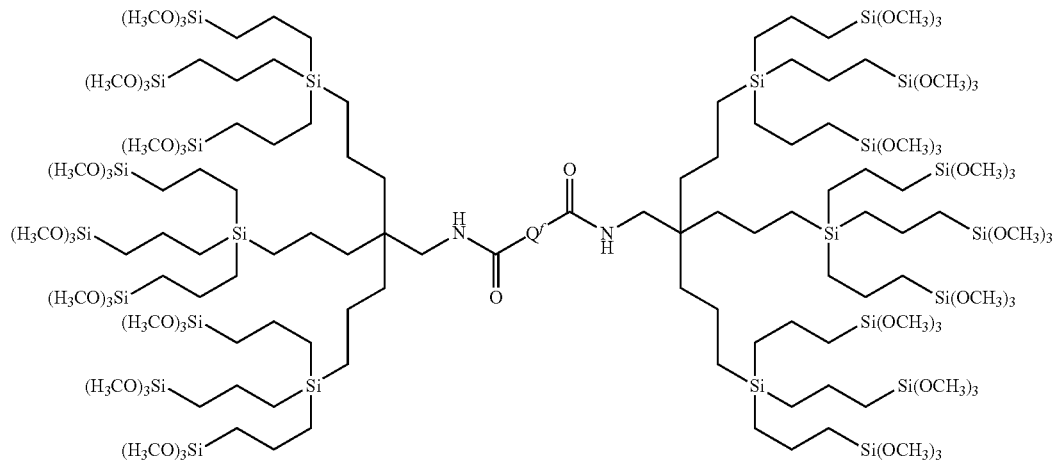

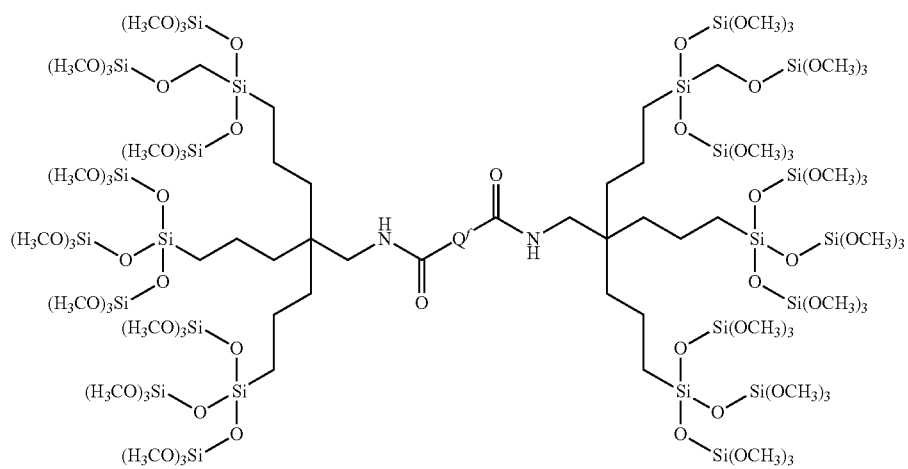

As specific examples of the present compound, the following compounds may be mentioned. In the formulae, n1 to n12 represent the number of repetition of units, and are properly adjusted within a range of from 1 to 200.

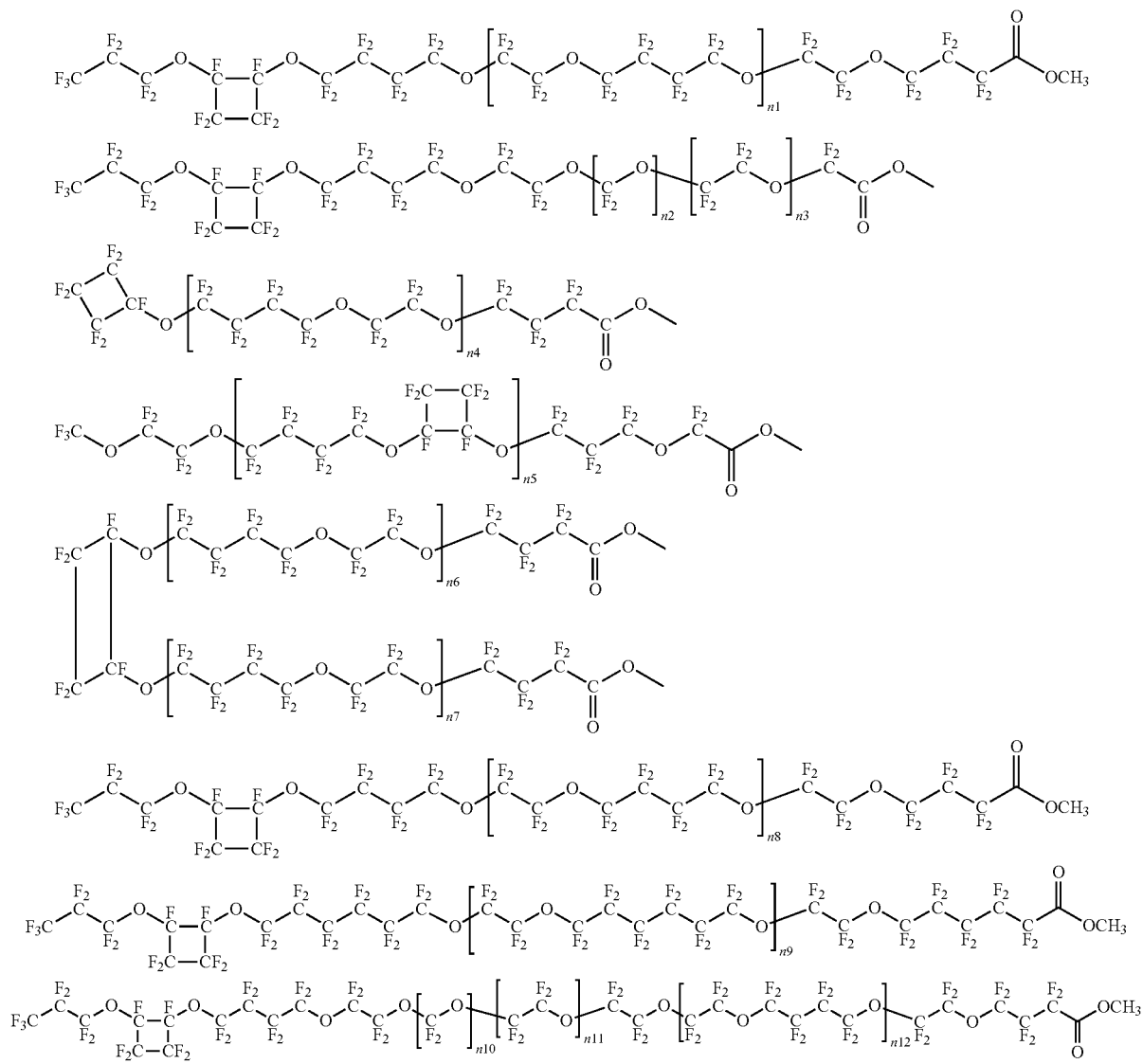

(Method for Producing Compound (1A) and Compound (1B))

As an example of the method for producing the compound (1A) and the compound (1B), a method for producing the compound (1A) and the compound (1B) having a reactive silyl group will be described. When a function-imparting group T other than the reactive silyl group is to be introduced, in the following production method, instead of compound (3a), a compound having a desired function-imparting group and a substituent capable of undergoing addition reaction to a double bond may be used. Further, the following reaction is an addition reaction to a double bond, however, it is also possible to introduce the function-imparting group T by utilizing a known reaction such as esterification or amidation.

The compound (1A) may be produced, for example, by a method of subjecting compound (2A) and compound (3a) or compound (3b) to hydrosilylation. The compound (1B) may be produced, for example, by a method of subjecting compound (2B) and compound (3a) or compound (3b) to hydrosilylation.

$$[R^f\text{—}]_{a1}Q^{10}[\text{—CH}\text{=}CH_2]_{b1} \quad (2A)$$

$$[CH_2\text{=}CH\text{—}]_{b2}Q^{20}\text{-}Q^f\text{-}Q^{20}[\text{—CH}\text{=}CH_2]_{b2} \quad (2B)$$

In the formula (2A), $Q^{10}$ is a (a1+b1) valent linking group, and reference symbols other than $Q^{10}$ are the same as the reference symbols in the formula (1A). In the formula (2B), $Q^{20}$ is a b2+1 valent linking group, the two $Q^{20}$ may be the same or different, and reference symbols other than $Q^{20}$ are the same as the reference symbols in the formula (1B).

$Q^{10}[\text{—CH}\text{=}CH_2]_{b1}$ becomes $Q^1$ in the compound (1A) after the hydrosilylation. As $Q^{10}$, the same groups as $Q^1$ may be mentioned, and the preferred embodiments are also the same. $Q^{20}[\text{—CH}\text{=}CH_2]_{b2}$ becomes $Q^2$ in the compound (2B) after the hydrosilylation. As $Q^{20}$, the same group as $Q^2$ may be mentioned, and the preferred embodiments are also the same.

$$HSi(R)_{3-c}(L)_c \quad (3a)$$

$$HSi(R^8)_{3-k}[\text{—}(OSi(R^9)_2)_p\text{—O—}Si(R)_{3-c}(L)_c]_k \quad (3b)$$

Reference symbols in the formulae (3a) and (3b) are the same as the reference symbols in the formulae (1A), (1B)

and (g3). The compound (3b) may be produced, for example, by the method disclosed in JP-A-2018-085493.

As $Q^{10}[-CH=CH_2]_{b1}$, in that the compound (1A) will readily be produced, preferred are group (g4-1) (provided that a1=d1+d3 and b1=d2+d4), group (g4-2) (provided that a1=e1 and b1=e2), group (g4-3) (provided that a1=1 and b1=2), group (g4-4) (provided that a1=h1 and b1=h2), group (g4-5) (provided that a1=i1 and b1=i2), group (g4-6) (provided that a1=1 and b1=1), and group (g4-7) (provided that a1=1 and b1=i3).

As $Q^{20}[-CH=CH_2]b2$, in that the compound (1B) will readily be produced, preferred are group (g4-1) (provided that b2=d2+d4), group (g4-2) (provided that b2=e2), group (g4-3) (provided that b2=2), group (g4-4) (provided that b2=h2), group (g4-5) (provided that b2=i2), group (g4-6) (provided that b2=1), and group (g4-7) (provided that b2=i3).

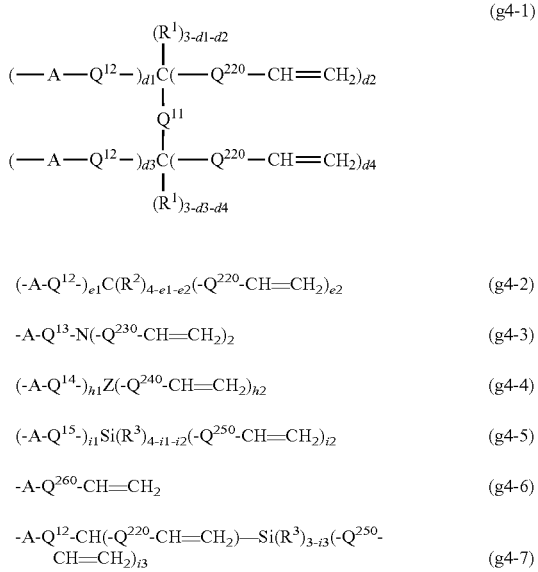

(-A-Q$^{12}$-)$_{e1}$C(R$^2$)$_{4-e1-e2}$(-Q$^{220}$-CH=CH$_2$)$_{e2}$ (g4-2)

-A-Q$^{13}$-N(-Q$^{230}$-CH=CH$_2$)$_2$ (g4-3)

(-A-Q$^{14}$-)$_{h1}$Z(-Q$^{240}$-CH=CH$_2$)$_{h2}$ (g4-4)

(-A-Q$^{15}$-)$_{i1}$Si(R$^3$)$_{4-i1-i2}$(-Q$^{250}$-CH=CH$_2$)$_{i2}$ (g4-5)

-A-Q$^{260}$-CH=CH$_2$ (g4-6)

-A-Q$^{12}$-CH(-Q$^{220}$-CH=CH$_2$)—Si(R$^3$)$_{3-i3}$(-Q$^{250}$-CH=CH$_2$)$_{i3}$ (g4-7)

In the formulae, $Q^{220}$ is an alkylene group, a group having —C(O)NR$^6$—, —C(O)—, —NR$^6$— or —O— between carbon atoms of an alkylene group having at least 2 carbon atoms, an alkylene group having —C(O)NR$^6$—, —C(O)—, —NR$^6$— or —O— at the terminal on the side not bonded to —CH=CH$_2$, or a group having —C(O)NR$^6$—, —C(O)—, —NR$^6$— or —O— between carbon atoms of an alkylene group having at least 2 carbon atoms and having —C(O)NR$^6$—, —C(O)—, —NR$^6$— or —O— at the terminal on the side not bonded to —CH=CH$_2$, and when $Q^{10}$ or $Q^{20}$ has two or more $Q^{220}$, the two or more $Q^{220}$ may be the same or different. $Q^{230}$ is an alkylene group, or a group having —C(O)NR$^6$—, —C(O)—, —NR$^6$— or —O— between carbon atoms of an alkylene group having at least 2 carbon atoms, and the two or more $Q^{230}$ may be the same or different. $Q^{240}$ is $Q^{220}$ when the atom in Z to which $Q^{240}$ is bonded is a carbon atom, or $Q^{230}$ when the atom in Z to which $Q^{240}$ is bonded is a nitrogen atom, and when $Q^{10}$ or $Q^{20}$ has two or more $Q^{240}$, the two or more $Q^{240}$ may be the same or different. $Q^{250}$ is an alkylene group, or a group having —C(O)NR$^6$—, —C(O)—, —NR$^6$— or —O— between carbon atoms of an alkylene group having at least 2 carbon atoms, and when $Q^{10}$ or $Q^{20}$ has two or more $Q^{250}$, the two or more $Q^{250}$ may be the same or different. $Q^{260}$ is an alkylene group, or a group having —C(O)NR$^6$—, —C(O)—, —NR$^6$— or —O— between carbon atoms of an alkylene group having at least 2 carbon atoms. Reference symbols other than $Q^{220}$, $Q^{230}$, $Q^{240}$, $Q^{250}$ and $Q^{260}$ are the same as the reference symbols in the formulae (g2-1) to (g2-7).

$Q^{220}$-CH=CH$_2$ becomes $Q^{22}$ in the compound (1A) and the compound (1B) after the hydrosilylation. As $Q^{220}$, the same groups as $Q^{22}$ may be mentioned, and the preferred embodiments are also the same.

$Q^{230}$-CH=CH$_2$ becomes $Q^{23}$ in the compound (1A) and the compound (1B) after the hydrosilylation. As $Q^{230}$, the same groups as $Q^{23}$ may be mentioned, and the preferred embodiments are also the same.

$Q^{240}$-CH=CH$_2$ becomes $Q^{24}$ in the compound (1A) and the compound (1B) after the hydrosilylation. As $Q^{240}$, the same groups as $Q^{24}$ may be mentioned, and the preferred embodiments are also the same.

$Q^{250}$-CH=CH$_2$ becomes $Q^{25}$ in the compound (1A) and the compound (1B) after the hydrosilylation. As $Q^{250}$, the same groups as $Q^{25}$ may be mentioned, and the preferred embodiments are also the same.

$Q^{260}$-CH=CH$_2$ becomes $Q^{26}$ in the compound (1A) and the compound (1B) after the hydrosilylation. As $Q^{260}$, the same groups as $Q^{26}$ may be mentioned, and the preferred embodiments are also the same.

As other embodiment of $Q^{10}[-CH=CH_2]_{b1}$, group (g4-8) (provided that a1=d1+d3 and b1=the total of k), group (g4-9) (provided that a1=e1 and b1=the total of k), group (g4-10) (provided that a1=1 and b1=the total of k), group (g4-11) (provided that a1=h1 and b1=the total of k), group (g4-12) (provided that a1=i1 and b1=the total of k), group (g4-13) (provided that a1=1 and b1=k), and group (g4-14) (provided that a1=1 and b1=the total of k) may be mentioned.

As other embodiment of $Q^{20}[-CH=CH_2]b2$, group (g4-8) (provided that b2=the total of k), group (g4-9) (provided that b2=the total of k), group (g4-10) (provided that b2=the total of k), group (g4-11) (provided that b2=the total of k), group (g4-12) (provided that b2=the total of k), group (g4-13) (provided that b2=k), and group (g4-14) (provided that b2=the total of k) may be mentioned.

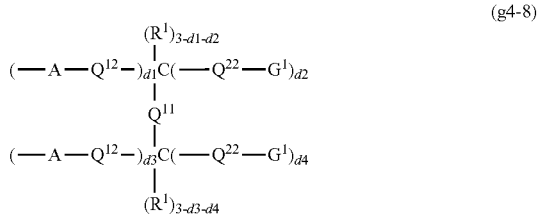

(-A-Q$^{12}$-)$_{e1}$C(R$^2$)$_{4-e1-e2}$(-Q$^{22}$-G$^1$)$_{e2}$ (g4-9)

-A-Q$^{13}$-N(-Q$^{23}$-G$^1$)$_2$ (g4-10)

(-A-Q$^{14}$-)$_{h1}$Z(-Q$^{24}$-G$^1$)$_{h2}$ (g4-11)

(-A-Q$^{15}$-)$_{i1}$Si(R$^3$)$_{4-i1-i2}$(-Q$^{25}$-G$^1$)$_{i2}$ (g4-12)

-A-Q$^{26}$-G$^1$ (g4-13)

-A-Q$^{12}$-CH(-Q$^{22}$-G$^1$)-Si(R$^3$)$_{3-i3}$(-Q$^{25}$-G$^1$)$_{i3}$ (g4-14)

In the formulae, G$^1$ is group (g5), the two or more G$^1$ which $Q^{10}[-CH=CH_2]_{b1}$ or $Q^{20}[-CH=CH_2]_{b2}$ has may be the same or different, and reference symbols other than $G^1$ are the same as the reference symbols in the formulae (g2-1) to (g2-7).

$$—Si(R^8)_{3-k}(-Q^{30}-CH=CH_2)_k \qquad (g5)$$

In the formula, $Q^{30}$ is an alkylene group, or a group having —C(O)NR$^6$—, —C(O)—, —NR$^6$— or —O— between carbon atoms of an alkylene group having at least 2 carbon atoms, the two or more $Q^{30}$ may be the same or different, and reference symbols other than $Q^{30}$ are the same as the reference symbols in the formula (g3).

$Q^{30}$-CH=CH$_2$ becomes $Q^3$ in group (g3) after the hydrosilylation. As $Q^{30}$, the same groups as $Q^3$ may be mentioned (excluding —(OSi(R$^9$)$_2$)$_p$—O—), and the preferred embodiments are also the same.

(Method for Producing Compound (2A) and Compound (2B))

The compound (2A) wherein $Q^{10}[—CH=CH_2]_{b1}$ is group (g4-1) and the compound (2B) wherein $Q^{20}[—CH=CH_2]_{b2}$ is group (g4-1) may be produce, for example, by the method disclosed in WO2017/187775 except for a change in the method for producing a precursor of the R$^f$ moiety or a precursor of the Q$^f$ moiety.

The compound (2A) wherein $Q^{10}[—CH=CH_2]_{b1}$ is group (g4-2) and the compound (2B) wherein $Q^{20}[—CH=CH_2]_{b2}$ is group (g4-2) may be produced, for example, by the method disclosed in JP-A-2015-199906, the method disclosed in Patent Document 1, the method disclosed in JP-A-2016-204656, the method disclosed in JP-A-2016-222859, the method disclosed in Patent Document 2, the method disclosed in WO2017/187775, or the method disclosed in WO2019/039226 except for a change in the method for producing a precursor of the R$^f$ moiety or a precursor of the Q$^f$ moiety.

The compound (2A) wherein $Q^{10}[—CH=CH_2]_{b1}$ is group (g4-3) and the compound (2B) wherein $Q^{20}[—CH=CH_2]_{b2}$ is group (g4-3) may be produced, for example, by the method disclosed in WO2017/038832 except for a change in the method for producing a precursor of the R$^f$ moiety or a precursor of the Q$^f$ moiety.

The compound (2A) wherein $Q^{10}[—CH=CH_2]_{b1}$ is group (g4-4) and the compound (2B) wherein $Q^{20}[—CH=CH_2]b2$ is group (g4-4) may be produced, for example by the method disclosed in WO2019/039186 except for a change in the method for producing a precursor of the R$^f$ moiety or a precursor of the Q$^f$ moiety.

The compound (2A) wherein $Q^{10}[—CH=CH_2]_{b1}$ is group (g4-5) and the compound (2B) wherein $Q^{20}[—CH=CH_2]b2$ is group (g4-5) may be produced, for example, by the method disclosed in Patent Document 1, or the method disclosed in WO2016/121211 except for a change in the method for producing a precursor of the R$^f$ moiety or a precursor of the Q$^f$ moiety.

The compound (2A) wherein $Q^{10}[—CH=CH_2]_{b1}$ is group (g4-6) and the compound (2B) wherein $Q^{20}[—CH=CH_2]b2$ is group (g4-6) may be produced, for example, by the method disclosed in JP-A-2012-072272, the method disclosed in WO2013/121984, or the method disclosed in WO2013/121986 except for a change in the method for producing a precursor of the R$^f$ moiety or a precursor of the Q$^f$ moiety.

The compound (2A) wherein $Q^{10}[—CH=CH_2]_{b1}$ is group (g4-7) and the compound (2B) wherein $Q^{20}[—CH=CH_2]_{b2}$ is group (g4-7) may be produced, for example, by the method disclosed in WO2019/163282 except for a change in the method for producing a precursor of the R$^f$ moiety or a precursor of the Q$^f$ moiety.

The compound (2A) wherein $Q^{10}[—CH=CH_2]_{b1}$ is any of group (g4-8) to group (g4-14) and the compound (2B) wherein $Q^{20}[—CH=CH_2]_{b2}$ is any of group (g4-8) to group (g4-14) may be produced, for example, by the method disclosed in WO2019/163282 except for a change in the method for producing a precursor of the R$^f$ moiety or a precursor of the Q$^f$ moiety.

As the precursor of the R$^f$ moiety in the compound (2A), for example, compound (4A) may be mentioned.

As the precursor of the Q$^f$ moiety in the compound (2B), for example, compound (4B) may be mentioned.

$$R^f\text{-}E^1 \qquad (4A)$$

$$E^1\text{-}Q^f\text{-}E^1 \qquad (4B)$$

In the formulae, $E^1$ is —CH$_2$—OH, —C(O)—X, —I, —OC(O)R$^{f5}$, —SO$_2$F, —CH$_2$—SO$_2$R$^{f5}$, —CH$_2$—NH$_2$, or —CH$_2$—O—CH$_2$CH=CH$_2$. X is a halogen atom, an alkoxy group, a hydroxy group or an amino group. R$^{f5}$ is a perfluoroalkyl group or a group having —O— between carbon atoms of a perfluoroalkyl group having at least 2 carbon atoms. Reference symbols other than $E^1$, X and R$^{f5}$ are the same as the reference symbols in the formula (2A) and the formula (2B).

As the compound (4A) and the compound (4B), for example, in a case where the after-described fluorinated compound (A) has a plurality of —O— between carbon atoms and has $E^1$ at its terminal, such a fluorinated compound (A) may be mentioned. In a case where the after-described fluorinated compound (A) does not have a plurality of —O— between carbon atoms, the compound (4A) and the compound (4B) may be produced by using the fluorinated compound (A) as a starting material, introducing at least one oxyfluoroalkylene unit e.g. by a known addition reaction to form a polyfluoropolyether chain, and as the case requires, introducing $E^1$ to the terminal of the polyfluoropolyether chain e.g. by a known method.

As a method of introducing $E^1$ to the terminal of the polyfluoropolyether chain, for example, the method disclosed in WO2009/008380, the method disclosed in WO2013/121984, the method disclosed in WO2013/121986, the method disclosed in WO2015/087902, the method disclosed in Patent Document 1, the method disclosed in WO2017/038832, the method disclosed in WO2018/143433, and the method disclosed in WO2018/216630 may be mentioned.

With the above-described present compound, which has a monovalent or bivalent polyfluoropolyether chain, a surface layer excellent in fingerprint stain removability can be formed.

Further, with the present compound, which has a reactive silyl group, a surface layer excellent in abrasion resistance can be formed.

Further, with the present compound, in which the monovalent polyfluoropolyether chain has at least one of a monovalent fluorinated cyclic structure at its free end and a bivalent fluorinated cyclic structure in its main chain, or the bivalent polyfluoropolyether chain has a bivalent fluorinated cyclic structure in its main chain, it is possible to form a surface layer excellent in sliding resistance without lowering abrasion resistance and fingerprint stain removability.

[Method for Producing Fluorinated Compound]

Now, a method for producing a fluorinated compound useful as a raw material of the present compound having a silyl group will be described. Some of the following fluorinated compounds correspond to the present compound having a function-imparting group T other than the silyl group in some cases.

As a method for producing a fluorinated compound having at least one of a monovalent 4-membered fluorinated cyclic structure and a bivalent 4-membered fluorinated cyclic structure (hereinafter sometimes referred to as "fluorinated compound (A)") according to a first embodiment, a method of reacting compound (11) and compound (12) to obtain compound (21) may be mentioned.

$$CF_2=CF-(O)_q-R^{11}-E \qquad (11)$$

$$CF_2=CF-R^{12} \qquad (12)$$

$$R^{12}-\underset{F_2C-CF_2}{\overset{F}{\underset{|}{C}}-\overset{F}{\underset{|}{C}}}-(O)_q-R^{11}-E \qquad (21)$$

In the formulae, $R^{11}$ is an alkylene group, a group having —O— between carbon atoms of an alkylene group having at least 2 carbon atoms, a fluoroalkylene group (provided that when E is —OH, the terminal on the E side is $CH_2$), or a group having —O— between carbon atoms of a fluoroalkylene group having at least 2 carbon atoms (provided that when E is —OH, the terminal on the E side is $CH_2$). $R^{12}$ is a halogen atom, a perfluoroalkyl group, or a group having —O— between carbon atoms of a perfluoroalkyl group having at least 2 carbon atoms, q is 0 or 1. E is —OH, —$OR^{14}$, —$SR^{14}$, —$C(O)OR^{14}$, —$C(O)NHR^{14}$, —$C(O)NR^{14}R^{15}$, —$SO_2X^1$, —$C(O)X^1$, or a halogen atom. $R^{14}$ and $R^{15}$ are each independently an alkyl group. $X^1$ is a halogen atom.

The number of carbon atoms in the alkylene group or the fluoroalkylene group as $R^{11}$ is, in that the fluorinated compound (A) will readily be produced, preferably from 1 to 10, more preferably from 1 to 8, particularly preferably from 2 to 6. When the alkylene group or the fluoroalkylene group has —O— between carbon atoms, the lower limit of the number of carbon atoms in such a group is 2.

$R^{11}$ may, for example, be —$CH_2$—, —$CH_2CH_2$—, —CHF—, —$CF_2CH_2$—, —$CF_2CF_2CH_2$—, —$CF_2$—, —$CF_2CF_2$—, —$CF_2CF_2OCF_2$—, —$CF(CF_3)CF_2OCF(CF_3)$—, or —$CF_2CF_2CF_2CF_2CH_2$—.

As the compound (11), for example, the following compounds may be mentioned.

$CF_2$=$CFOCF_3$,
$CF_2$=$CFOCF_2CF_3$,
$CF_2$=$CFOCF_2CF_2CF_3$,
$CF_2$=$CFOCF_2CF(CF_3)OCF_2CF_2CF_3$,
$CF_2$=$CFOCF_2CF(CF_3)OCF_2CF(CF_3)OCF_2CF_2CF_3$,
$CF_2$=$CFOCF_2CF(CF_3)OCF_2CF_2SO_2F$,
$CF_2$=$CFOCF_2CFCF_2CONH_2$,
$CF_2$=$CFOCF_2CF_2CF_2CH_2OCF_2CHFOCF_3$,
$CF_2$=$CFOCF_2CF_2CF_2CH_2OCF_2CHFOCF_2CF_3$,
$CF_2$=$CFOCF_2CF_2CF_2CH_2OCF_2CHFOCF_2CF_2CF_3$,
$CF_2$=$CFOCF_2CF_2CF_2CF_2CH_2OCF_2CHFOCF_3$,
$CF_2$=$CFOCF_2CF_2CF_2CF_2CF_2CH_2OCF_2CHFOCF_2CF_3$,
$CF_2$=$CFOCF_2CF_2CF_2CF_2CF_2CH_2OCF_2CHFOCF_2CF_2CF_3$,
$CF_2$=$CFOCF_2CF_2CF_2OCHFCF_2OCH_3$,
$CF_2$=$CFOCF_2CF_2CF_2OCHFCF_2OCH_2CH_3$,
$CF_2$=$CFOCF_2CF_2CF_2OCHFCF_2OCH_2CH_2CH_3$,
$CF_2$=$CFOCF_2CF_2CF_2OCHFCF_2OCH_2CH_2CH_2CH_3$,
$CF_2$=$CFOCF_2CF_2CF_2OCHFCF_2OCH_2CH_2CH_2CH_3$,
$CF_2$=$CFOCF_2CF_2CF_2OCHFCF_2OCH_2CH_2CH_2CH_2CH_3$,
$CF_2$=$CFOCF_2CF_2CF_2CF_2OCHFCF_2OCH_3$,
$CF_2$=$CFOCF_2CF_2CF_2CF_2OCHFCF_2OCH_2CH_3$,
$CF_2$=$CFOCF_2CF_2CF_2CF_2OCHFCF_2OCH_2CH_2CH_3$,
$CF_2$=$CFOCF_2CF_2CF_2CF_2OCHFCF_2OCH_2CH_2CH_2CH_3$,
$CF_2$=$CFOCF_2CF_2CF_2CF_2OCHFCF_2OCH_2CH_2CH_2CH_3$,
$CF_2$=$CFOCF_2CF_2CF_2CF_2OCHFCF_2OCH_2CH_2CH_2CH_2CH_3$,
$CF_2$=$CFOCF_2CF_2CF_2CF_2OCHFCF_2OCH_2CH_2CH_2CH_2CH_3$,
$CF_2$=$CFOCF_2CF_2CF_2CF_2CF_2OCHFCF_2OCH_3$,
$CF_2$=$CFOCF_2CF_2CF_2CF_2CF_2OCHFCF_2OCH_2CH_3$,
$CF_2$=$CFOCF_2CF_2CF_2CF_2CF_2OCHFCF_2OCH_2CH_3$,
$CF_2$=$CFOCF_2CF_2CF_2CF_2CF_2OCHFCF_2OCH_2CH_2$ $CH_2CH_3$,
$CF_2$=$CFOCF_2CF_2CF_2CF_2CF_2OCHFCF_2OCH_2$ $CH_2CH_2CH_3$,
$CF_2$=$CFOCF_2CF_2CF_2CF_2CF_2OCHFCF_2OCH_2CH_2$ $CH_2CH_2CH_3$,
$CF_2$=$CFOCF_2CF_2CF_2CF_2CF_2CH_2OH$,
$CF_2$=$CFOCF_2CF_2CF_2CF_2CF_2COOCH_3$,
$CF_2$=$CFOCF_2CF_2CF_2CF_2CF_2CONHCH_3$,
$CF_2$=$CFOCF_2CF_2CF_2CF_2CF_2CONH_2$,
$CF_2$=$CFOCF_2CF_2CF_2CF_2CF_2SO_2F$,
$CF_2$=$CFOCF_2C(CF_2OCF_2CF_2SO_2F)FOCF_2CF_2SO_2F$,
$CF_2$=$CFOCF_2CF_2SO_2F$,
$CF_2$=$CF_0CF_2CF_2CF_2CF_2SO_2F$,
$CF_2$=$CF$—O—$CF_2CF_2CF_2CH_2$—OH,
$CF_2$=$CF$—O—$CF_2CF_2CF_2$—$C(O)OCH_3$,
$CF_2$=$CF$—O—$CF_2CF_2CF_2$—$C(O)NHCH_3$,
$CF_2$=$CF$—O—$CF_2CF_2CF_2$—$C(O)N(CH_3)_2$,
$CF_2$=$CF$—O—$CF_2CF_2CF_2$—$SO_2F$,
$CF_2$=$CF$—O—$CF_2CF_2CF_2$—F,
$CF_2$=$CF$—O—$CF_2CF_2CF_2$—Cl,
$CF_2$=$CF$—O—$CF_2CF_2CF_2$—Br,
$CF_2$=$CF$—O—$CF_2CF_2CF_2$—I,
$CF_2$=$CF$—O—$CF_2CF_2CH_2$—$OCH_3$,
$CF_2$=$CF$—O—$CF_2CF_2CF_2$—C(O)F,
$CF_2$=$CF$—O—$CF_2CF_2CF_2OCHFCF_2$—$OCH_3$.

The number of carbon atoms in the perfluoroalkyl group as $R^{12}$ is, in that the fluorinated compound (A) will readily be produced, preferably from 1 to 10, more preferably from 1 to 8, particularly preferably from 1 to 6. When the perfluoroalkyl group has —O— between carbon atoms, the lower limit value of the number of carbon atoms in such a group is 2.

The halogen atom as $R^{12}$ is, in that the fluorinated compound (A) will readily be produced, preferably a fluorine atom or a chlorine atom.

As $R^{12}$, for example, —F, —Cl, —$CF_3$, —$CF_2CF_3$, —$CF_2CF_2OCF_3$, and —$CF(CF_3)CF_2CF_3$ may be mentioned.

As the compound (12), for example, $CF_2$=$CF_2$, $CF_2$=$CF$—$CF_3$, $CF_2$=$CF$—$CF_2CF_3$, and $CF_2$=$CF$—$CF(CF_3)_2$ may be mentioned.

The number of carbon atoms in the alkyl group as $R^{14}$ or $R^{15}$ is, in that the fluorinated compound A will readily be produced, preferably from 1 to 10, more preferably from 1 to 8, particularly preferably from 1 to 6.

$X^1$ is, in that the fluorinated compound (A) will readily be produced, preferably a fluorine atom or a chlorine atom.

The compound (21) may be produced, for example, by charging the compound (11) and the compound (12) to a reactor, followed by heating.

The reactor may, for example, a container made of a metal (such as stainless steel).

The reaction temperature is, for example, from 150 to 250° C.

The reaction time is, for example, from 50 to 300 hours.

The reaction pressure is, for example, at least atmospheric pressure and at most 2.0 MPa (gauge), and is preferably at most 0.2 MPa.

As a method for producing fluorinated compound (A) according to a second embodiment, a method of reacting compound (11) and compound (13) to obtain compound (22) may be mentioned.

(11)

(13)

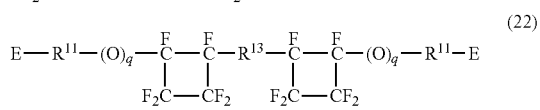
(22)

In the formulae, $R^{13}$ is a fluoroalkylene group, a fluoroalkylene group having —O— at both terminals, or a group having —O— between carbon atoms of a fluoroalkylene group having at least 2 carbon atoms. Reference symbols other than $R^{13}$ are the same as the reference symbols in the formula (11), and the preferred embodiments are also the same. The two $R^{11}$, q and E in the formula (22) may be the same or different, respectively. When the compound (11) is a single compound, in the obtainable compound (22), the two $R^{11}$, E and q are the same, respectively. Whereas when the compound (11) is a combination of a plurality of compounds, in the obtainable compound (22), the two $R^{11}$, the two E and/or the two q are different from each other.

The number of carbon atoms in the fluoroalkylene group as $R^{13}$ is, in that the fluorinated compound (A) will readily be produced, preferably from 0 to 10, more preferably from 1 to 8, particularly preferably from 1 to 6. When the fluoroalkylene group has —O— between carbon atoms, the lower limit value of the number of carbon atoms in such a fluoroalkylene group is 2.

As $R^{13}$, for example, —$CF_2$—, —$CF_2CF_2$—, —$CF(CF_3)CF_2$—, —$CF_2CH_2CF_2$—, —$OCF_2CF_2CF_2O$—, and —$CF_2OCF_2CF_2OCF_2$— may be mentioned.

As the compound (13), for example, $CF_2$=$CF$—$OCF_2CF_2CF_2O$—$CF$=$CF_2$, $CF_2$=$CF$—$OCF_2$—$CF$=$CF_2$, $CF_2$=$CF$—$OCF_2CF_2CF_2CF_2O$—$CF$=$CF_2$, $CF_2$=$CFOCF_2CF_2OCF$=$CF_2$, $CF_2$=$CFOCF_2CF_2CF_2CF_2CF_2OCF$=$CF_2$, $CF_2$=$CFOCF_2CF_2CF_2CF_2CF_2CF_2OCF$=$CF_2$, $CF_2$=$CFOCF_2OCF_2OCF$=$CF_2$, $CF_2$=$CFOCF_2CF_2OCF_2CF_2OCF$=$CF_2$, and $CF_2$=$CFOCF_2CF_2OCF_2CF_2OCF_2OCF$=$CF_2$ may be mentioned.

The compound (22) may be produced in the same manner as the compound (21).

As a method for producing fluorinated compound (A) according to a third embodiment, a method of reacting one or more compounds (11) to obtain compound (23) may be mentioned.

(11)

(23)

Reference symbols in the formula (23) are the same as the reference symbols in the formula (11), and the preferred embodiments are also the same.

The compound (23) may be produced in the same manner as the compound (21). The compound (11) may be a single compound or a combination of a plurality of compounds corresponding to the formula (11). When the compound (11) is a single compound, in the obtainable compound (23), the two $R^{11}$, E and q are the same, respectively. Whereas when the compound (11) is a combination of a plurality of compounds, in the obtainable compound (23), the two $R^{11}$, the two E and/or the two q are different from each other.

As a method for producing fluorinated compound (A) according to a fourth embodiment, a method of reacting one or more compounds (13) to obtain compound (24) may be mentioned.

$CF_2$=$CF$—$R^{13}$—$CF$=$CF_2$ (13)

(24)

r is an integer of at least 1. Reference symbols other than r are the same as the reference symbols in the formula (13), and the preferred embodiments are also the same, r is preferably an integer of from 1 to 100, particularly preferably from 2 to 20.

The compound (24) may be produced in the same manner as the compound (21). The compound (13) may be a single compound or a combination of a plurality of compounds corresponding to the formula (13). When the compound (13) is a single compound, in the obtainable compound (24), the two or more $R^{13}$ are the same. Whereas when the compound (13) is a combination of a plurality of compounds, in the obtainable compound (24), the two or more $R^{13}$ are different from each other.

As a method for producing fluorinated compound (A) according to a fifth embodiment, a method of reacting compound (11) and compound (13) to obtain compound (25) may be mentioned.

(11)

(13)

-continued

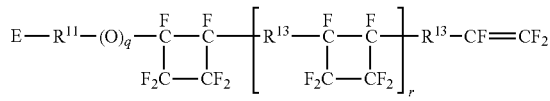
(25)

Reference symbols in the formula (25) are the same as the reference symbols in the formulae (11), (13) and (24), and the preferred embodiments are also the same.

The compound (25) may be produced in the same manner as the compound (21).

As a method for producing fluorinated compound (A) according to a sixth embodiment, a method of reacting one or more compounds (12) to obtain compound (26) may be mentioned.

(12)

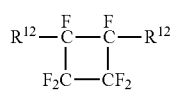
(26)

Reference symbols in the formula (26) are the same as the reference symbols in the formula (12), and the preferred embodiments are also the same.

The compound (26) may be produced in the same manner as the compound (21). The compound (12) may be a single compound or a combination of a plurality of compounds corresponding to the formula (12). When the compound (12) is a single compound, in the obtainable compound (26), the two $R^{12}$ are the same. Whereas when the compound (12) is a combination of a plurality of compounds, in the obtainable compound (23), the two $R^{11}$ are different from each other.

As a method for producing fluorinated compound (A) according to a seventh embodiment, a method of reacting compound (12) and compound (13) to obtain compound (27) may be mentioned.

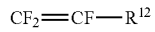
(12)

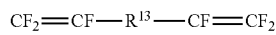
(13)

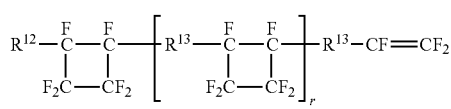
(27)

r2 is an integer of at least 1. Reference symbols other than r2 are the same as the reference symbols in the formulae (12) and (13), and the preferred embodiments are also the same. r2 is preferably an integer of from 1 to 100, particularly preferably from 2 to 20.

The compound (27) may be produced in the same manner as the compound (21).

[Fluorinated Compound-Containing Composition]

The fluorinated compound-containing composition of the present invention (hereinafter sometimes referred to as "the present composition") contains at least one type of fluorinated ether compound which is the present compound, and other fluorinated ether compound other than the present compound. The present composition may contain, as the present compound, for example, both the compound (1A) and the compound (1B). The present composition does not contain a liquid medium described hereinafter.

As other fluorinated ether compound, both compound inevitably included and compound used in combination depending upon e.g. the application may be mentioned.

As the compound used in combination with the present compound, a known fluorinated ether compound and a fluorinated oil may be mentioned.

As the fluorinated oil, for example, polytetrafluoroethylene (PTFE), an ethylene/chlorotrifluoroethylene copolymer (ECTFE), polyvinylidene fluoride (PVDF), polyvinyl fluoride (PVF), and polychlorotrifluoroethylene (PCTFE) may be mentioned.

Further, as the known fluorinated ether compound, for example, fluorinated ether compounds commercially available as a surface treatment agent may be mentioned. When the present composition contains a known fluorinated ether compound, a new effect such as a complement to properties of the present compound may sometimes be achieved.

As the known fluorinated ether compound, for example, compounds described in the following documents may be mentioned.

Perfluoropolyether-modified aminosilanes described in JP-A-H11-029585, silicon-containing organic fluorinated polymers described in Japanese Patent No. 2874715, organic silicon compounds described in JP-A-2000-144097, perfluoropolyether-modified aminosilanes described in JP-A-2000-327772, fluorinated siloxanes described in JP-A-2002-506887, organic silicone compounds described in JP-A-2008-534696, fluorinated modified hydrogenated polymers described in Japanese Patent No. 4138936, compounds described in U.S. Patent Application No. 2010/0129672, WO2014/126064 and JP-A-2014-070163, organosilicon compounds described in WO2011/060047 and WO2011/059430, fluorinated organosilane compounds described in WO2012/064649, fluoroxyalkylene group-containing polymers described in JP-A-2012-72272, fluorinated ether compounds described in WO2013/042732, WO2013/121984, WO2013/121985, WO2013/121986, WO2014/163004, JP-A-2014-080473, WO2015/087902, WO2017/038830, WO2017/038832 and WO2017/187775, perfluoro(poly)ether-containing silane compounds described in JP-A-2014-218639, WO2017/022437, WO2018/079743 and WO2018/143433, perfluoropolyether group-containing compounds described in WO2019/098230, fluoropolyether group-containing polymer-modified silanes described in JP-A-2015-199906, JP-A-2016-204656, JP-A-2016-210854 and JP-A-2016-222859, and fluorinated ether compounds described in WO2018/216630, WO2019/039226, WO2019/039341, WO2019/039186, WO2019/044479, JP-A-2019-44158, WO2019/044479 and WO2019/163282.

As commercial products of the fluorinated compound, KY-100 series (KY-178, KY-185, KY-195, etc.) manufactured by Shin-Etsu Chemical Co., Ltd., Afluid (registered trademark) S550 manufactured by AGC Inc., OPTOOL (registered trademark) DSX, OPTOOL (registered trademark) AES, OPTOOL (registered trademark) UF503, OPTOOL (registered trademark) UD509, etc., manufactured by DAIKIN INDUSTRIES, LTD. may, for example, be mentioned.

When the present compound and a known fluorinated ether compound are used in combination in the present composition, the content ratio is properly adjusted depending upon e.g. the application. The content of the present compound in the present composition is preferably from 10 to 90 mass %, more preferably from 20 to 80 mass %, further preferably from 25 to 75 mass %. Within the above range, properties of the present compound are sufficiently exhibited and in addition, properties of the fluorinated ether compound used in combination can also be sufficiently obtained.

As the compound inevitably included, a fluorinated ether compound formed as a by-product in the process for producing the present compound (hereinafter sometimes referred to as "by-product fluorinated ether compound") may be mentioned.

As the by-product fluorinated ether compound, for example, an unreacted fluorinated compound (for example, the compound (2A) or the compound (2B)), and fluorinated ether compounds formed through isomerization of some of the allyl groups into an inner olefin accompanying hydrosilylation during the production of the present compound may, for example, be mentioned.

When the present composition contains the by-product fluorinated ether compound, the by-product fluorinated ether compound may be removed by purification, however, it may be contained in the present composition within a range where the properties of the present compound are sufficiently exhibited, whereby the process for purifying the by-product fluorinated ether compound can be simplified.

When the known fluorinated ether compound is not used in combination, the content of the present compound is preferably at least 60 mass % and less than 100 mass %, more preferably at least 70 mass % and less than 100 mass %, particularly preferably at least 80 mass % and less than 100 mass % in the present composition.

The content of the by-product fluorinated ether compound is preferably more than 0 mass % and at most 40 mass %, more preferably more than 0 mass % and at most 30 mass %, particularly preferably more than 0 mass % and at most 20 mass % in the present composition.

When the content of the present compound and the content of the by-product fluorinated ether compound are within the above ranges, the resulting surface layer will be more excellent in initial water/oil repellency, abrasion resistance, fingerprint stain removability, light resistance and chemical resistance.

Further, as the inevitably included compound, additives such as an acid catalyst or a basic catalyst to promote hydrolysis and condensation reaction of the hydrolyzable silyl group may be mentioned. The acid catalyst may, for example, be hydrochloric acid, nitric acid, acetic acid, sulfuric acid, phosphoric acid, sulfonic acid, methanesulfonic acid or p-toluenesulfonic acid. The basic catalyst may, for example, be sodium hydroxide, potassium hydroxide or ammonia.

The content of such a component is preferably from 0 to 9.999 mass %, particularly preferably from 0 to 0.99 mass % in the present composition.

[Coating Liquid]

The coating liquid of the present invention (hereinafter sometimes referred to as "the present coating liquid") comprises the present compound or the present composition, and a liquid medium. The present coating liquid may be a solution or a dispersion.

The liquid medium is preferably an organic solvent. The organic solvent may be a fluorinated organic solvent, may be a non-fluorinated organic solvent, or may contain both solvents.

The fluorinated organic solvent may, for example, be a fluorinated alkane, a fluorinated aromatic compound, a fluoroalkyl ether, a fluorinated alkylamine, a fluoroalcohol, etc.

The fluorinated alkane is preferably a $C_{4-8}$ compound. Commercially available products may, for example, be $C_6F_{13}H$ (manufactured by AGC Inc., ASAHIKLIN (registered trademark) AC-2000), $C_6F_{13}C_2H_5$ (manufactured by AGC Inc., ASAFIIKLIN (registered trademark) AC-6000), and $C_2F_5CHFCHFCF_3$ (manufactured by Chemours, Vertrel (registered trademark) XF).

The fluorinated aromatic compound may, for example, be hexafluorobenzene, trifluoromethylbenzene, perfluorotoluene or bis(trifluoromethyl)benzene.

The fluoroalkyl ether is preferably a $C_{4-12}$ compound. Commercially available products may, for example, be $CF_3CH_2OCF_2CF_2FI$ (manufactured by AGC Inc., ASAHIKLIN (registered trademark) AE-3000), $C_4F_9OCH_3$ (manufactured by 3M, Novec (registered trademark) 7100), $C_4F_9OC_2H_5$ (manufactured by 3M, Novec (registered trademark) 7200), and $C_2F_5CF(OCH_3)C_3F_7$ (manufactured by 3M, Novec (registered trademark) 7300).

The fluorinated alkylamine may, for example, be perfluorotripropylamine or perfluorotributylamine, The fluoroalcohol may, for example, be 2,2,3,3-tetrafluoropropanol, 2,2,2-trifluoroethanol or hexafluoroisopropanol.

The non-fluorinated organic solvent is preferably a compound consisting solely of hydrogen atoms and carbon atoms, or a compound consisting solely of hydrogen atoms, carbon atoms and oxygen atoms, and may be a hydrocarbon, an alcohol, a ketone, an ether, or an ester.

The liquid medium may be a mixed medium having two or more types mixed.

The content of the present compound or the present composition is preferably from 0.001 to 10 mass %, particularly preferably from 0.01 to 1 mass % in the present coating liquid.

The content of the liquid medium is preferably from 90 to 99.999 mass %, particularly preferably from 99 to 99.99 mass % in the present coating liquid.

[Article]

The article of the present invention (hereinafter sometimes referred to as "the present article") has a surface layer formed of the present compound or the present composition on the surface of a substrate. The surface layer may be formed on a part of the surface of the substrate, or may be formed on the entire surface of the substrate. The surface layer may be formed on the surface of the substrate in a film form or may be dotted on the surface.

When the present compound having a silyl group is used, the surface layer contains the present compound in a state where some or all of hydrolyzable silyl groups in the present compound are hydrolyzed and the silanol groups are subjected to dehydration condensation reaction.

The thickness of the surface layer is preferably from 1 to 100 nm, particularly preferably from 1 to 50 nm. When the thickness of the surface layer is at least 1 nm, sufficient effect by the surface treatment is likely to be obtained. When the thickness of the surface layer is at most 100 nm, utilization efficiency will be high. The thickness of the surface layer can be calculated from an oscillation period of an interference pattern of reflected X-ray, obtained by X-ray reflectance method using an X-ray diffractometer for thin film analysis (manufactured by Rigaku Corporation, ATX-G).

The substrate may be a substrate which is desired to have water/oil repellency imparted. For example, a substrate to be used as touched with other article (such as a stylus) or human fingers, a substrate to be held by human hands when operated, and a substrate to be placed on other article (such as a table) may be mentioned.

The material of the substrate may, for example, be a metal, a resin, glass, sapphire, ceramic, stone or a composite material thereof. The glass may be chemically tempered. The substrate may have a primer film such as a $SiO_2$ film formed on its surface.

As the substrate, a substrate for a touch panel, a substrate for display or a spectacle lens is preferred, and a substrate for a touch panel is particularly preferred. As the material of a substrate for a touch panel, glass or a transparent resin is preferred.

Further, as the substrate, a glass or resin film to be used for an exterior portion (excluding the display portion) of a device such as a mobile phone (such as a smartphone), a personal digital assistant (such as a tablet), a gaming machine or a remote controller, is also preferred.

[Method for Producing Article]

The present article may be produced, for example, by the following method.

A method of treating the surface of a substrate by dry coating method using the present compound or the present composition, to form a surface layer formed of the compound (1A), the compound (1B) or the present composition on the surface of the substrate.

A method of applying the present coating liquid to the surface of a substrate by wet coating method, followed by drying to form a surface layer formed of the present compound or the present composition on the surface of the substrate.

As the dry coating method, a method such as vacuum deposition, CVD or sputtering may be mentioned. As the dry coating method, with a view to suppressing decomposition of the present compound and from the viewpoint of simplicity of apparatus, vacuum deposition method is preferred. At the time of vacuum deposition, a pelletized material having a metal porous product of iron, steel or the like impregnated with the present compound or the present composition may be used. A pelletized material impregnated with the present compound or the present composition, obtained by impregnating a metal porous product of iron, steel or the like with the present coating liquid and drying the liquid medium, may be used.

The wet coating method may, for example, be a spin coating method, a wipe coating method, a spray coating method, a squeegee coating method, a dip coating method, a die coating method, an ink-jet method, a flow coating method, a roll coating method, a casting method, a Langmuir-Blodgett method, or a gravure coating method.

EXAMPLES

Now, the present invention will be described in further detail with reference to Examples, but the present invention is not limited to these Examples. Hereinafter, "%" is "mass %" unless otherwise specified. Ex. 1 to 4, 7 to 10 and 13 to 16 are Examples of the present compound having a reactive silyl group, and Ex. 5, 6, 11 and 12 are Comparative Examples.

More particularly, Ex. 1-3 to 1-8, Ex. 2-2 to 2-7, Ex. 3-2 to 3-7, Ex. 4-1 to 4-6, Ex. 14-2 to 14-7, and Ex. 15-2 to 15-7 are Examples of the method for preparing the fluorinated ether compound of the present invention.

Ex. 1

Ex. 1-1

Compound (11-1) was obtained with reference to the method described in Ex. 1-1 of WO2013-121984.

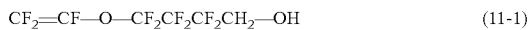

$CF_2=CF-O-CF_2CF_2CF_2CH_2-OH$ (11-1)

Ex. 1-2

Into a 100 mL metal reactor, 10 g of the compound (11-1) obtained in Ex. 1-1 was put, followed by stirring at 175° C. for 200 hours. The resulting organic phase was concentrated to obtain 6 g of compound (23-1).

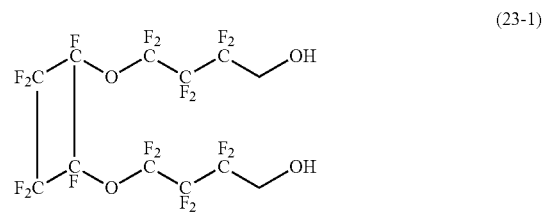

(23-1)

NMR spectrum of compound (23-1):
$^1$H-NMR (300.4 MHz, solvent: CDCl$_3$, reference: tetramethylsilane (TMS)) δ (ppm): 4.1 (4H)
$^{19}$F-NMR (282.7 MHz, solvent: CDCl$_3$, reference: CFCl$_3$) δ (ppm): −80 (2F), −85 (2F), −123 (4F), −126 (4F), −128 (2F), −131 (2F), −137 (1F), −139 (1F).

Ex. 1-3

Into a 200 mL eggplant flask, 5 g of the compound (23-1) obtained in Ex. 1-2 and 1.2 g of potassium carbonate were put, followed by stirring at 120° C., and 25 g of the compound (11-1) was added, followed by stirring at 120° C. for 2 hours. The temperature in the eggplant flask was adjusted to 25° C., and 30 g each of AC-2000 and hydrochloric acid were put, followed by liquid separation, and the organic phase was concentrated. The obtained reaction crude liquid was purified by column chromatography to obtain 21 g of compound (4-1).

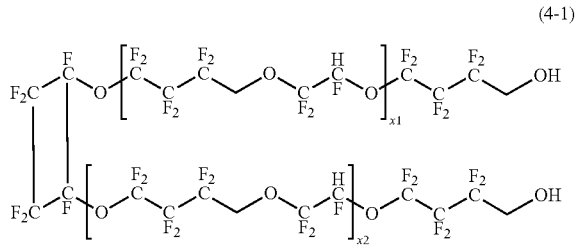

(4-1)

NMR spectrum of compound (4-1):
$^1$H-NMR (300.4 MHz, solvent: CDCl$_3$, reference: TMS) δ (ppm): 6.0 (1 OH), 4.6 (20H), 4.1 (4H).
$^{19}$F-NMR (282.7 MHz, solvent: CDCl$_3$, reference: CFCl$_3$) δ (ppm): −80 (2F), −85 (22F), −91 (20F), −120 (20F), −123 (4F), −126 (24F), −128 (2F), −131 (2F), −137 (1F), −139 (1F), −144 (10F).
Average of x1+x2: 10.

Ex. 1-4

Into a 50 mL eggplant flask, 20 g of the compound (4-1) obtained in Ex. 1-3, 7.1 g of a sodium fluoride power, 20 g of AC-2000 and 20 g of $CF_3CF_2CF_2OCF(CF_3)COF$ were added. In a nitrogen atmosphere, the mixture was stirred at 50° C. for 24 hours. The temperature in the flask was adjusted to 25° C., and the sodium fluoride powder was removed by filtration. Excess $CF_3CF_2CF_2OCF(CF_3)COF$ and AC-2000 were distilled off under reduced pressure to obtain 24 g of compound (4-2).

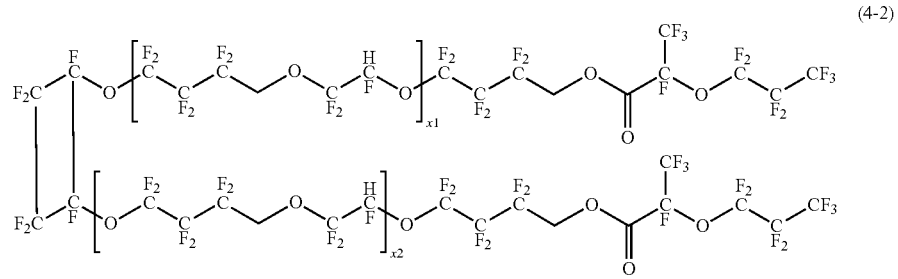

(4-2)

NMR spectrum of compound (4-2):
$^1$H-NMR (300.4 MHz, solvent: $CDCl_3$, reference: TMS) δ (ppm): 6.0 (10H), 5.0 (4H), 4.6 (20H).
$^{19}$F-NMR (282.7 MHz, solvent: $CDCl_3$, reference: $CFCl_3$) δ (ppm): −79 (4F), −80 (2F), −81 (6F), −82 (6F), −85 (22F), −91 (20F), −119 (4F), −120 (20F), −126 (24F), −128 (2F), −129 (4F), −131 (2F), −131 (2F), −137 (1F), −139 (1F), −144 (10F).
Average of x1+x2: 10.

Ex. 1-5

Into a 500 mL metal reactor, 250 mL of $ClCF_2CFClCF_2OCF_2CF_2Cl$ (hereinafter referred to as "CFE-419") was put, followed by bubbling with nitrogen gas, and by bubbling with 20 vol % fluorine gas diluted with nitrogen gas. A CFE-419 solution (concentration: 10%, compound (4-2): 20 g) of the compound (4-2) obtained in Ex. 1-4 was charged over a period of 3 hours. The ratio of the rate (mol/hour) of introduction of fluorine gas to the rate (mol/hour) of introduction of hydrogen atoms in the compound (4-2) was controlled to be 2:1. After the charge of the compound (4-2), a CFE-419 solution (concentration: 0.1%, benzene: 0.1 g) of benzene was intermittently charged. After the charge of benzene, bubbling with fluorine gas was conducted, and finally the system in the reactor was sufficiently replaced with nitrogen gas. The solvent was distilled off to obtain 21 g of compound (4-3).

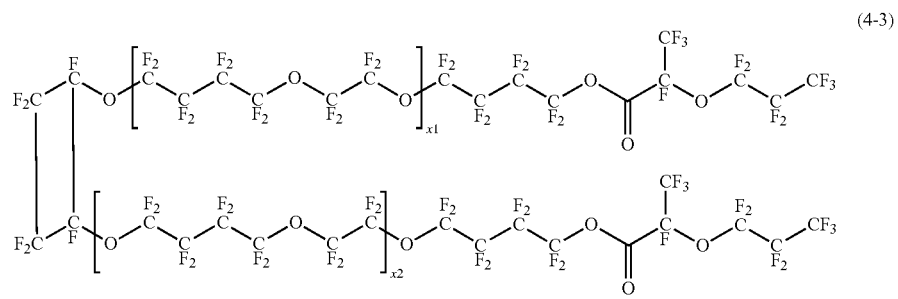

(4-3)

NMR spectrum of compound (4-3):
$^{19}$F-NMR (282.7 MHz, solvent: CDCl$_3$, reference: CFCl$_3$) δ (ppm): −79 (4F), −80 (2F), −81 (6F), −82 (6F), −83 (46F), −87 (40F), −124 (48F), −128 (2F), −129 (4F), −131 (2F), −131 (2F), −137 (1F), −139 (1F).
Average of x1+x2: 10.

Ex. 1-6

Into a 50 mL eggplant flask, 20 g of the compound (4-3) obtained in Ex. 1-5, 1.8 g of sodium fluoride and 20 mL of AC-2000 were put, followed by stirring in an ice bath. 1.4 g of methanol was put, followed by stirring at 25° C. for 1 hour. The mixture was subjected to filtration, and the filtrate was purified by column chromatography to obtain 14 g of compound (4-4).

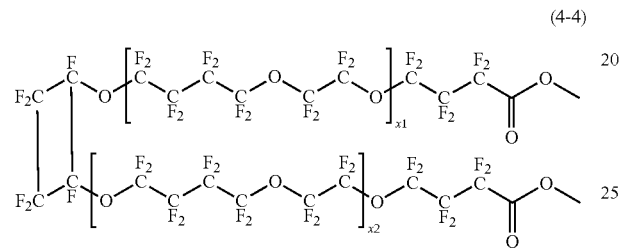
(4-4)

NMR spectrum of compound (4-4):

$^1$H-NMR (300.4 MHz, solvent: CDCl$_3$, reference: TMS) δ (ppm): 4.2 (6H).

$^{19}$F-NMR (282.7 MHz, solvent: CDCl$_3$, reference: CFCl$_3$) δ (ppm): −80 (2F), −83 (42F), −87 (40F), −119 (4F), −124 (44F), −128 (2F), −131 (2F), −137 (1F), −139 (1F).

Average of x1+x2: 10.

Ex. 1-7

Into a 50 mL eggplant flask, 12 g of the compound (4-4) obtained in Ex. 1-6, 1.5 g of H$_2$NCH$_2$C(CH$_2$CH=CH$_2$)$_3$ and 12 mL of AC-2000 were put, followed by stirring at 0° C. for 24 hours. The reaction crude liquid was purified by column chromatography to obtain 9 g of compound (2-1).

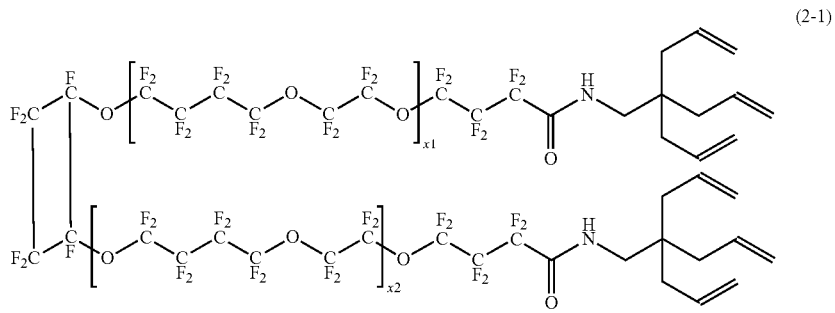
(2-1)

NMR spectrum of compound (2-1):
$^1$H-NMR (300.4 MHz, solvent: CDCl$_3$, reference: TMS) δ (ppm): 6.1 (6H), 5.2 (12H), 3.4 (4H), 2.1 (12H).
$^{19}$F-NMR (282.7 MHz, solvent: CDCl$_3$, reference: CFCl$_3$) δ (ppm): −80 (2F), −83 (42F), −87 (40F), −120 (4F), −124 (44F), −128 (2F), −131 (2F), −137 (1F), −139 (1F).
Average of x1+x2: 10.

Ex. 1-8

Into a 50 mL eggplant flask, 1 g of the compound (2-1) obtained in Ex. 1-7, 0.21 g of trimethoxysilane, 0.001 g of aniline, 1.0 g of AC-6000 and 0.0033 g of a platinum//1,3-divinyl-1,1,3,3-tetramethyldisiloxane complex were put, followed by stirring at 25° C. overnight. The solvent and the like were distilled off under reduced pressure to obtain 1.2 g of compound (1-1).

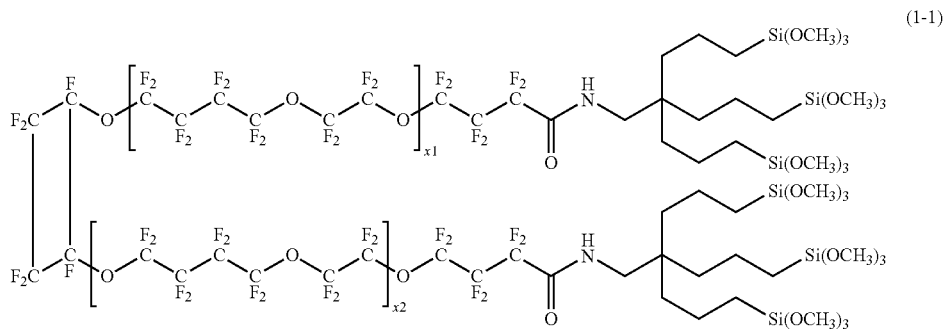

NMR spectrum of compound (1-1):
¹H-NMR (300.4 MHz, solvent: CDCl₃, reference: TMS) δ (ppm): 3.6 (54H), 3.4 (4H), 1.3 (24H), 0.9 (12H).
¹⁹F-NMR (282.7 MHz, solvent: CDCl₃, reference: CFCl₃) δ (ppm): −80 (2F), −83 (42F), −87 (40F), −120 (4F), −124 (44F), −128 (2F), −131 (2F), −137 (1F), −139 (1F).
Average of x1+x2: 10.

Ex. 2

Ex. 2-1

Into a 100 mL metal reactor, 20 g of the compound (11-1) obtained in Ex. 1-1 was put, and 7.2 g of CF₂=CF₂ was put, followed by stirring at 180° C. for 300 hours. The resulting organic phase was concentrated to obtain 8 g of compound (21-1).

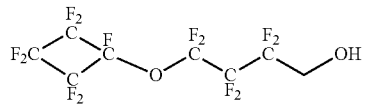

NMR spectrum of compound (21-1):
¹H-NMR (300.4 MHz, solvent: CDCl₃, reference: TMS) δ (ppm): 4.1 (2H).
¹⁹F-NMR (282.7 MHz, solvent: CDCl₃, reference: CFCl₃) δ (ppm): −80 (2F), −123 (2F), −126 (2F), −128 (2F), −130 (4F), −137 (1F).

Ex. 2-2

20 g compound (4-5) was obtained in the same manner as in Ex. 1-3 except that the compound (23-1) was changed to 3.4 g of the compound (21-1) obtained in Ex. 2-1 and that the amount of potassium carbonate was changed to 0.6 g.

(4-5)

NMR spectrum of compound (4-5):
¹H-NMR (300.4 MHz, solvent: CDCl₃, reference: TMS) δ (ppm): 6.0 (1 OH), 4.6 (20H), 4.1 (2H).
¹⁹F-NMR (282.7 MHz, solvent: CDCl₃, reference: CFCl₃) δ (ppm): −80 (2F), −85 (20F), −91 (20F), −120 (20F), −123 (2F), −126 (22F), −128 (2F), −130 (4F), −137 (1F), −144 (10F).
Average of x: 10.

Ex. 2-3

18 g of compound (4-6) was obtained in the same manner as in Ex. 1-4 except that the compound (4-1) was changed to 16 g of the compound (4-5) obtained in Ex. 2-2, that the amount of the sodium fluoride powder was changed to 3.5 g and that the amount of CF₃CF₂CF₂OCF(CF₃)COF was changed to 10 g.

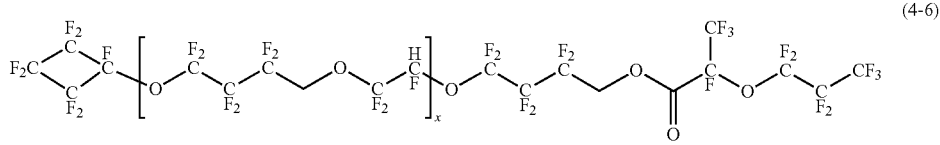

NMR spectrum of compound (4-6):
¹H-NMR (300.4 MHz, solvent: CDCl₃, reference: TMS) δ (ppm): 6.0 (1 OH), 5.0 (2H), 4.6 (20H).
¹⁹F-NMR (282.7 MHz, solvent: CDCl₃, reference: CFCl₃) δ (ppm): −79 (2F), −80 (2F), −81 (3F), −82 (3F), −85 (20F), −91 (20F), −119 (2F), −120 (20F), −126 (22F), −128 (2F), −129 (2F), −130 (4F), −131 (1F), −137 (1F), −144 (10F).
Average of x: 10.

Ex. 2-4

19 g of compound (4-7) was obtained in the same manner as in Ex. 1-5 except that the compound (4-2) was changed to 18 g of the compound (4-6) obtained in Ex. 2-3.

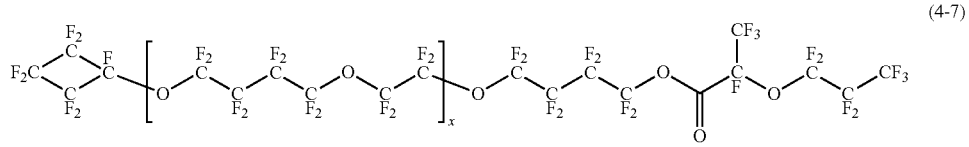
(4-7)

NMR spectrum of compound (4-7):
$^{19}$F-NMR (282.7 MHz, solvent: CDCl$_3$, reference: CFCl$_3$) δ (ppm): −79 (2F), −80 (2F), −81 (3F), −82 (3F), −83 (42F), −87 (40F), −124 (44F), −128 (2F), −129 (2F), −130 (4F), −131 (1F), −137 (1F).
Average of x: 10.

Ex. 2-5

14 g of compound (4-8) was obtained in the same manner as in Ex. 1-6 except that the compound (4-3) was changed to 19 g of the compound (4-7) obtained in Ex. 2-4.

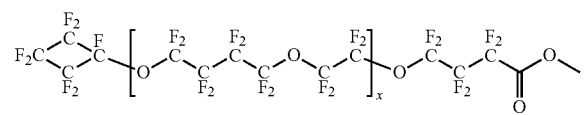
(4-8)

NMR spectrum of compound (4-8):
$^1$H-NMR (300.4 MHz, solvent: CDCl$_3$, reference: TMS) δ (ppm): 4.2 (3H).
$^{19}$F-NMR (282.7 MHz, solvent: CDCl$_3$, reference: CFCl$_3$) δ (ppm): −80 (2F), −83 (40F), −87 (40F), −119 (2F), −124 (42F), −128 (2F), −130 (4F), −137 (1F).
Average of x: 10.

Ex. 2-6

10 g of compound (2-2) was obtained in the same manner as in Ex. 1-7 except that compound (4-4) was changed to 14 g of the compound (4-8) obtained in Ex. 2-5.

NMR spectrum of compound (2-2):
$^1$H-NMR (300.4 MHz, solvent: CDCl$_3$, reference: TMS) δ (ppm): 6.1 (3H), 5.2 (6H), 3.4 (2H), 2.1 (6H).
$^{19}$F-NMR (282.7 MHz, solvent: CDCl$_3$, reference: CFCl$_3$) δ (ppm): −80 (2F), −83 (40F), −87 (40F), −120 (2F), −124 (42F), −128 (2F), −130 (4F), −137 (1F).
Average of x: 10.

Ex. 2-7

1.1 g of compound (1-2) was obtained in the same manner as in Ex. 1-8 except that compound (2-1) was changed to 1 g of the compound (2-2) obtained in Ex. 2-6.

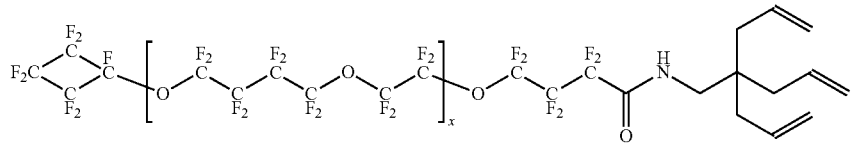
(1-2)

NMR spectrum of compound (1-2):
$^1$H-NMR (300.4 MHz, solvent: CDCl$_3$, reference: TMS) δ (ppm): 3.6 (27), 3.4 (2H), 1.3 (12H), 0.9 (6H).
$^{19}$F-NMR (282.7 MHz, solvent: CDCl$_3$, reference: CFCl$_3$) δ (ppm): −80 (2F), −83 (40F), −87 (40F), −120 (2F), −124 (42F), −128 (2F), −130 (4F), −137 (1F).
Average of x: 10.

Ex. 3

Ex. 3-1

Into a 500 mL eggplant flask, 39.4 g of CF$_2$=CFOCF$_2$CF$_2$CF$_2$CF$_2$OCF=CF$_2$, 3.2 g of methanol and 13.8 g of potassium carbonate were put, followed by stirring at 40° C. for 2 hours. Hydrochloric acid was added, followed by liquid separation, and the resulting organic phase was dehydrated over magnesium sulfate. Magnesium sulfate was removed by filtration, and the crude liquid was distilled to obtain 17.0 g of compound (11-2).

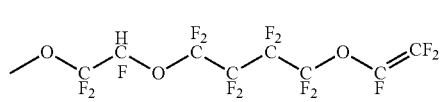
(11-2)

NMR spectrum of compound (11-2):
¹H-NMR (300.4 MHz, solvent: CDCl₃, reference: TMS) δ (ppm): 6.0 (1H), 3.4 (3H).
¹⁹F-NMR (282.7 MHz, solvent: CDCl₃, reference: CFCl₃) δ (ppm): −82 (4F), −90 (2F), −114 (1F), −122 (1F), −124 (4F), −135 (1F), −144 (1F).

Ex. 3-2

Into a 200 mL metal reactor, 15 g of the compound (11-2) obtained in Ex. 3-1 was put, and 138 g of CF₂=CFOCF₂CF₂CF₂OCF=CF₂ was put, followed by stirring at 160° C. for 300 hours. The temperature in the reactor was adjusted to 25° C., and 9.8 g of the compound (11-1) obtained in Ex. 1-1 was put, followed by stirring at 180° C. for 100 hours. The temperature in the reactor was adjusted to 25° C., and the obtained reaction crude liquid was purified by column chromatography to obtain 9.8 g of compound (4-9).

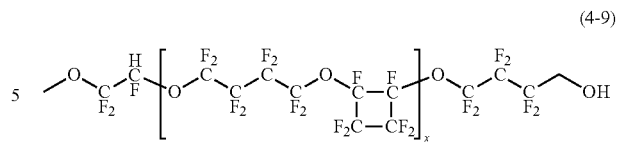
(4-9)

NMR spectrum of compound (4-9):
¹H-NMR (300.4 MHz, solvent: CDCl₃, reference: TMS) δ (ppm): 6.0 (1H), 4.0 (2H), 3.4 (3H).
¹⁹F-NMR (282.7 MHz, solvent: CDCl₃, reference: CFCl₃) δ (ppm): −82 (44F), −85 (2F), −90 (2F), −123 (2F), −124 (44F), −126 (2F), −128 (22F), −131 (22F), −137 (11F), −139 (11F), −144 (1F).
Average of x: 11.

Ex. 3-3

10 g of compound (4-10) was obtained in the same manner as in Ex. 1-4 except that the compound (4-1) was changed to 9 g of the compound (4-9) obtained in Ex. 3-2, that the amount of the sodium fluoride powder was changed to 0.4 g and that the amount of CF₃CF₂CF₂OCF(CF₃)COF was changed to 3.2 g.

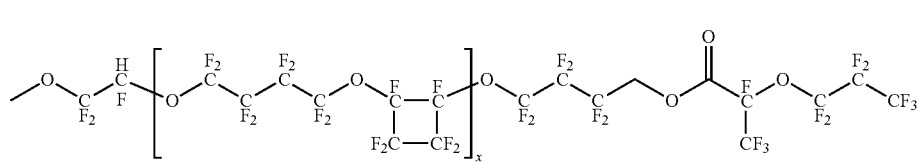
(4-10)

NMR spectrum of compound (4-10):
¹H-NMR (300.4 MHz, solvent: CDCl₃, reference: TMS) δ (ppm): 6.0 (1H), 5.0 (2H), 3.4 (3H).
¹⁹F-NMR (282.7 MHz, solvent: CDCl₃, reference: CFCl₃) δ (ppm): −79 (2F), −81 (3F), −82 (47F), −85 (2F), −90 (2F), −119 (2F), −124 (44F), −126 (2F), −128 (22F), −129 (2F), −131 (23F), −137 (11F), −139 (11F), −144 (1F).
Average of x: 11.

Ex. 3-4

9.2 g of compound (4-11) was obtained in the same manner as in Ex. 1-5 except that the compound (4-2) was changed to 10 g of the compound (4-10) obtained in Ex. 3-3, and that the time over which the CFE-419 solution of the compound (4-10) was charged was changed to 2 hours.

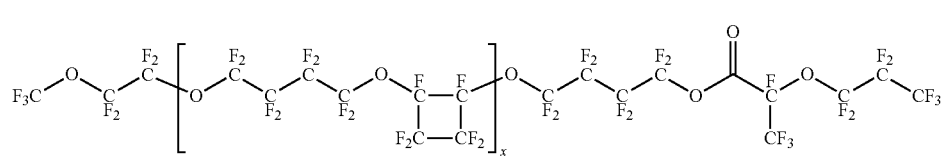
(4-11)

NMR spectrum of compound (4-11):

¹⁹F-NMR (282.7 MHz, solvent: CDCl₃, reference: CFCl₃) δ (ppm): −55 (3F), −79 (2F), −81 (3F), −82 (51F), −87 (4F), −124 (48F), −128 (22F), −129 (2F), −131 (23F), −137 (11F), −139 (11F).

Average of x: 11.

Ex. 3-5

Into a 50 mL eggplant flask, 9 g of the compound (4-11) obtained in Ex. 3-4, 0.4 g of sodium fluoride and 10 mL of AC-2000 were put, followed by stirring in an ice bath. 0.3 g of methanol was put, followed by stirring at 25° C. for 1 hour. The mixture was subjected to filtration, and the filtrate was purified by column chromatography to obtain 6.7 g of compound (4-12).

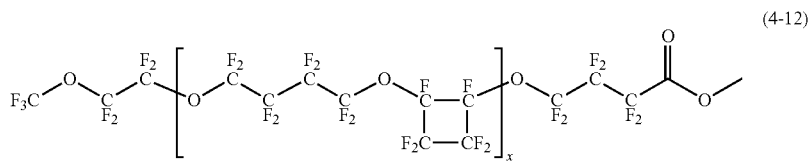

(4-12)

NMR spectrum of compound (4-12):
¹H-NMR (300.4 MHz, solvent: CDCl₃, reference: TMS) δ (ppm): 4.2 (3H).
¹⁹F-NMR (282.7 MHz, solvent: CDCl₃, reference: CFCl₃) δ (ppm): −55 (3F), −82 (46F), −87 (4F), −119 (2F), −124 (46F), −128 (22F), −131 (22F), −137 (11F), −139 (11F).
Average of x: 11.

Ex. 3-6

Into a 50 mL eggplant flask, 6 g of the compound (4-12) obtained in Ex. 3-5, 0.4 g of H₂NCH₂C(CH₂CH=CH₂)₃ and 6 mL of AC-2000 were put, followed by stirring at 0° C. for 24 hours. The reaction crude liquid was purified by column chromatography to obtain 4.3 g of compound (2-3).

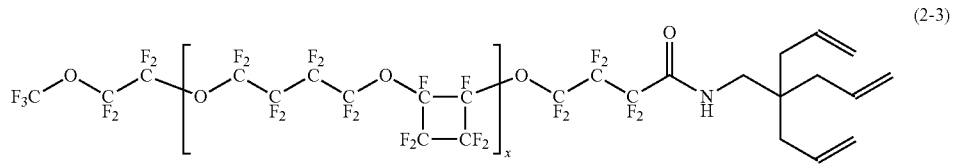

(2-3)

NMR spectrum of compound (2-3):
¹H-NMR (300.4 MHz, solvent: CDCl₃, reference: TMS) δ (ppm): 6.1 (3H), 5.2 (16H), 3.4 (2H), 2.1 (6H).
¹⁹F-NMR (282.7 MHz, solvent: CDCl₃, reference: CFCl₃) δ (ppm): −55 (3F), −82 (46F), −87 (4F), −120 (2F), −124 (46F), −128 (22F), −131 (22F), −137 (11F), −139 (11F).
Average of x: 11.

Ex. 3-7

1.2 g of compound (1-3) was obtained in the same manner as in Ex. 1-8 except that the compound (2-1) was changed to 1 g of the compound (2-3) obtained in Ex. 3-6.

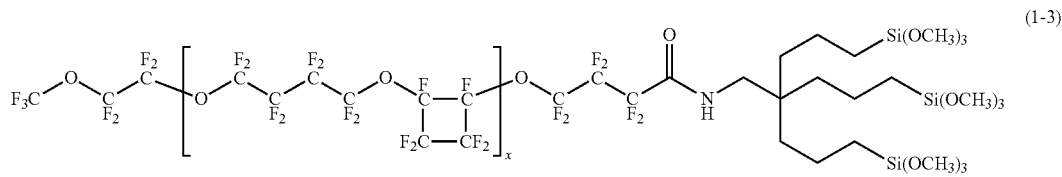

(1-3)

NMR spectrum of compound (1-3):

$^1$H-NMR (300.4 MHz, solvent: CDCl$_3$, reference: TMS) δ (ppm): 3.6 (27H), 3.4 (2H), 1.3 (12H), 0.9 (6H).

$^{19}$F-NMR (282.7 MHz, solvent: CDCl$_3$, reference: CFCl$_3$) δ (ppm): −55 (3F), −82 (46F), −87 (4F), −120 (2F), −124 (46F), −128 (22F), −131 (22F), −137 (11F), −139 (11F).

Average of x: 11.

Ex. 4

Ex. 4-1

Into a 500 mL metal reactor, 394 g of CF$_2$=CFOCF$_2$CF$_2$CF$_2$CF$_2$OCF=CF$_2$ was put, followed by stirring at 180° C. for 200 hours. The temperature in the reactor was adjusted to 25° C., and 55.6 g of the compound (11-1) obtained in Ex. 1-1 was put, followed by stirring at 180° C. for 100 hours. The temperature in the reactor was adjusted to 25° C., and the obtained reaction crude liquid was purified by column chromatography to obtain 45.0 g of compound (4-13).

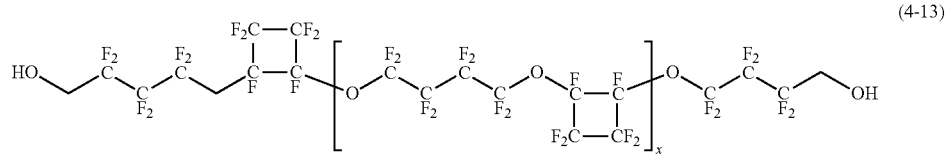

(4-13)

NMR spectrum of compound (4-13):
$^1$H-NMR (300.4 MHz, solvent: CDCl$_3$, reference: TMS) δ (ppm): 4.0 (4H).
$^{19}$F-NMR (282.7 MHz, solvent: CDCl$_3$, reference: CFCl$_3$) δ (ppm): −82 (40F), −85 (4F), −123 (4F), −124 (40F), −126 (4F), −128 (22F), −131 (22F), −137 (11F), −139 (11F).
Average of x: 10.

Ex. 4-2

22.8 g of compound (4-14) was obtained in the same manner as in Ex. 1-4 except that the compound (4-1) was changed to 20 g of the compound (4-13) obtained in Ex. 4-1, that the amount of the sodium fluoride powder was changed to 1.7 g and that the amount of CF$_3$CF$_2$CF$_2$OCF(CF$_3$)COF was changed to 14.8 g.

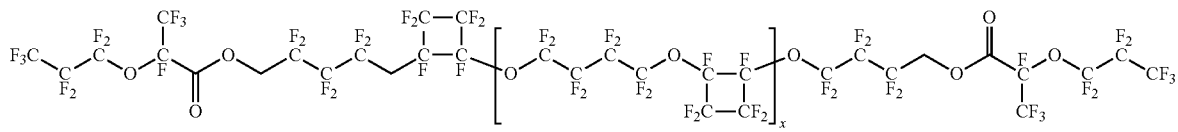

(4-14)

NMR spectrum of compound (4-14):
$^1$H-NMR (300.4 MHz, solvent: CDCl$_3$, reference: TMS) δ (ppm): 5.0 (4H).
$^{19}$F-NMR (282.7 MHz, solvent: CDCl$_3$, reference: CFCl$_3$) δ (ppm): −79 (4F), −81 (6F), −82 (46F), −85 (4F), −119 (4F), −124 (40F), −126 (4F), −128 (22F), −129 (4F), −131 (24F), −137 (11F), −139 (11F).
Average of x: 10.

Ex. 4-3

19.3 g of compound (4-15) was obtained in the same manner as in Ex. 1-5 except that the compound (4-2) was changed to 19.3 g of the compound (4-14) obtained in Ex. 4-2 and that the time over which the CFE-419 solution of the compound (4-14) was charged was changed to 5 hours.

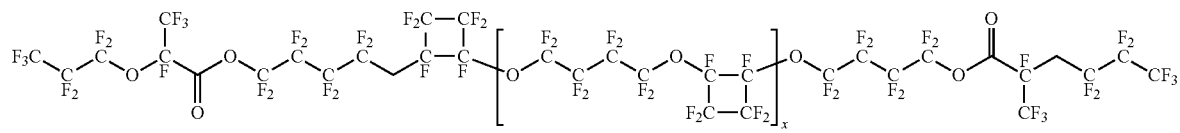

(4-15)

NMR spectrum of compound (4-15):
$^{19}$F-NMR (282.7 MHz, solvent: CDCl$_3$, reference: CFCl$_3$) δ (ppm): −79 (4F), −81 (6F), −82 (50F), −124 (48F), −128 (22F), −129 (4F), −131 (24F), −137 (11F), −139 (11F).
Average of x: 10.

Ex. 4-4

Into a 50 mL eggplant flask, 19.3 g of the compound (4-15) obtained in Ex. 4-3, 1.6 g of sodium fluoride and 20 mL of AC-2000 were put, followed by stirring in an ice bath. 1.2 g of methanol was put, followed by stirring at 25° C. for 1 hour. The mixture was subjected to filtration, and the filtrate was purified by column chromatography to obtain 13.5 g of compound (4-16).

(4-16)

NMR spectrum of compound (4-16):
$^1$H-NMR (300.4 MHz, solvent: CDCl$_3$, reference: TMS) δ (ppm): 4.2 (6H).
$^{19}$F-NMR (282.7 MHz, solvent: CDCl$_3$, reference: CFCl$_3$) δ (ppm): −82 (40F), −119 (4F), −124 (44F), −128 (22F), −131 (22F), −137 (11F), −139 (11F).
Average of x: 10.

Ex. 4-5

Into a 50 mL eggplant flask, 10.0 g of the compound (4-16) obtained in Ex. 4-4, 1.5 of H$_2$NCH$_2$C(CH$_2$CH=CH$_2$)$_3$ and 10 mL of AC-2000 were put, followed by stirring at 0° C. for 24 hours. The reaction crude liquid was purified by column chromatography to obtain 7.4 g of compound (2-4).

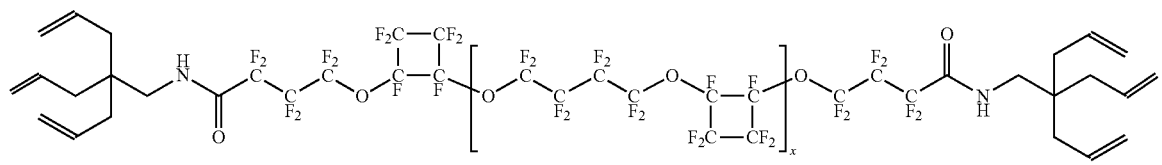

(2-4)

NMR spectrum of compound (2-4):
$^1$H-NMR (300.4 MHz, solvent: CDCl$_3$, reference: TMS) δ (ppm): 6.1 (6H), 5.2 (32H), 3.4 (4H), 2.1 (12H).
$^{19}$F-NMR (282.7 MHz, solvent: CDCl$_3$, reference: CFCl$_3$) δ (ppm): −82 (40F), −120 (4F), −124 (44F), −128 (22F), −131 (22F), −137 (11F), −139 (11F).
Average of x: 10.

Ex. 4-6

1.2 g of compound (1-4) was obtained in the same manner as in Ex. 1-8 except that the compound (2-1) was changed to 1 g of the compound (2-4) obtained in Ex. 4-5.

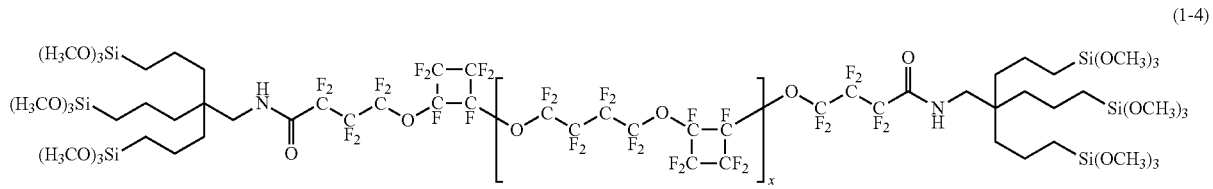

(1-4)

NMR spectrum of compound (1-4):
$^1$H-NMR (300.4 MHz, solvent: CDCl$_3$, reference: TMS) δ (ppm): 3.6 (54H), 3.4 (4H), 1.3 (24H), 0.9 (12H).
$^{19}$F-NMR (282.7 MHz, solvent: CDCl$_3$, reference: CFCl$_3$) δ (ppm): -82 (40F), -120 (4F), -124 (44F), -128 (22F), -131 (22F), -137 (11F), -139 (11F).
Average of x: 10.

Ex. 5

Compound (10-1) was obtained in accordance with the method described in Ex. 11 in Patent Document 2.
Average of x: 11.

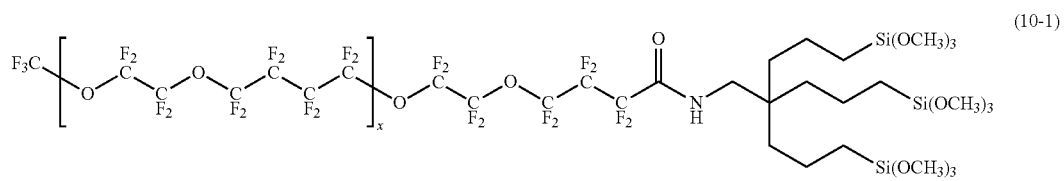

(10-1)

Ex. 6

Ex. 6-1

Into a 200 mL eggplant flask, 16.2 g of HOCH$_2$CF$_2$CF$_2$CH$_2$OH and 13.8 g of potassium carbonate were put, followed by stirring at 120° C., and 278 g of the compound (11-1) obtained in Ex. 1-1 was put, followed by stirring at 120° C. for 2 hours. Th temperature in the eggplant flask was adjusted to 25° C., and 50 g each of AC-2000 and hydrochloric acid were put, followed by liquid separation, and the organic phase was concentrated. The obtained reaction crude liquid was purified by column chromatography to obtain 117.7 g of compound (5-1).

NMR spectrum of compound (5-1):

$^1$H-NMR (300.4 MHz, solvent: CDCl$_3$, reference: TMS) δ (ppm): 6.0 (12H), 4.6 (20H), 4.2 (4H), 4.1 (4H).

$^{19}$F-NMR (282.7 MHz, solvent: CDCl$_3$, reference: CFCl$_3$) δ (ppm): -85 (24F), -90 (24F), -120 (20F), -122 (4F), -123 (4F), -126 (24F), -144 (12F).

Average of x1+x2: 10.

Ex. 6-2

24 g of compound (5-2) was obtained in the same manner as in Ex. 1-4 except that the compound (4-1) was changed to 20 g of the compound (5-1) obtained in Ex. 6-1, that the amount of the sodium fluoride powder was changed to 2.4 g and that the amount of CF$_3$CF$_2$CF$_2$OCF(CF$_3$)COF was changed to 18.8 g.

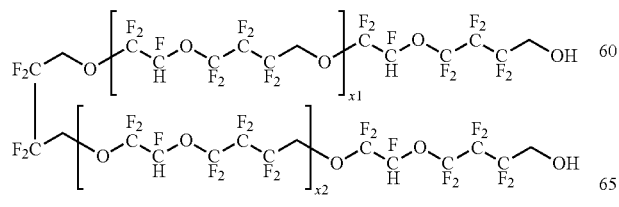

(5-1)

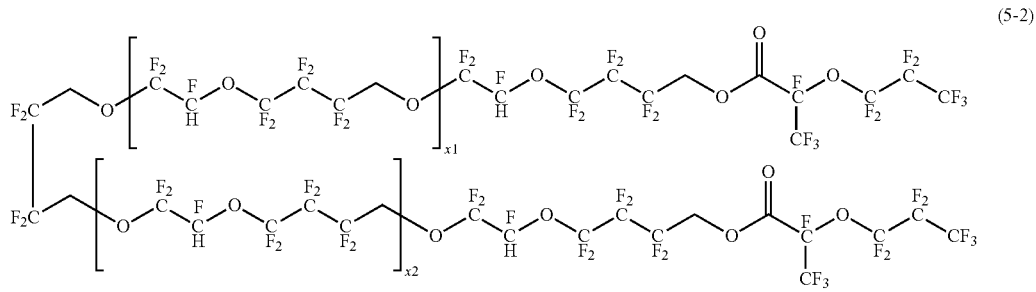

(5-2)

NMR spectrum of compound (5-2):
¹H-NMR (300.4 MHz, solvent: CDCl₃, reference: TMS) δ (ppm): 6.0 (12H), 5.0 (4H), 4.6 (20H), 4.2 (4H).
¹⁹F-NMR (282.7 MHz, solvent: CDCl₃, reference: CFCl₃) δ (ppm): −79 (4F), −81 (6F), −82 (6F), −85 (24F), −90 (24F), −119 (4F), −120 (20F), −122 (4F), −126 (24F), −129 (4F), −131 (2F), −144 (12F).
Average of x1+x2: 10.

Ex. 6-3

25.3 g of compound (5-3) was obtained in the same manner as in Ex. 1-5 except that the compound (4-2) was changed to 24 g of the compound (5-2) obtained in Ex. 6-2 and that the time over which the CFE-419 solution of the compound (5-2) was charged was changed to 6 hours.

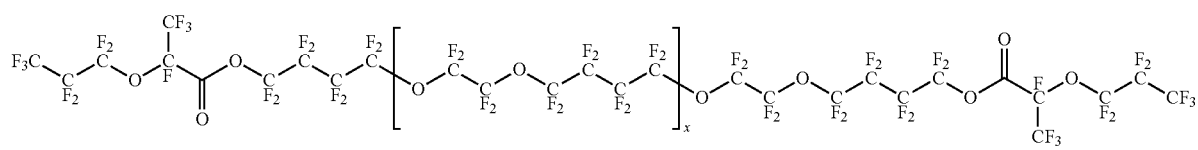

(5-3)

NMR spectrum of compound (5-3):
¹⁹F-NMR (282.7 MHz, solvent: CDCl₃, reference: CFCl₃) δ (ppm): −79 (4F), −81 (6F), −82 (6F), −83 (48F), −87 (44F), −124 (48F), −129 (4F), −131 (2F).
Average of x: 11.

Ex. 6-4

Into a 50 mL eggplant flask, 25.3 g of the compound (5-3) obtained in Ex. 6-3, 2.2 g of sodium fluoride and 25 mL of AC-2000 were put, followed by stirring in an ice bath. 1.7 g of methanol was put, followed by stirring at 25° C. for 1 hour. The mixture was subjected to filtration, and the filtrate was purified by column chromatography to obtain 15 g of compound (5-4).

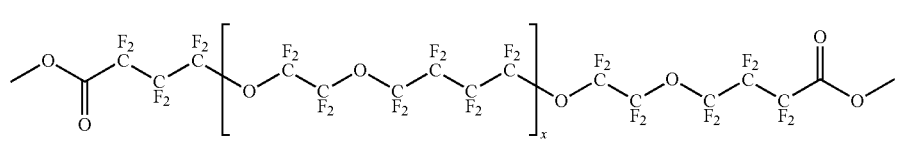

(5-4)

NMR spectrum of compound (5-4):
¹H-NMR (300.4 MHz, solvent: CDCl₃, reference: TMS) δ (ppm): 4.2 (6H).
¹⁹F-NMR (282.7 MHz, solvent: CDCl₃, reference: CFCl₃) δ (ppm): −83 (44F), −87 (44F), −119 (4F), −124 (44F).
Average of x: 11.

Ex. 6-5

Into a 50 mL eggplant flask, 15 g of the compound (5-4) obtained in Ex. 6-4, 3.2 g of H2 NCH$_2$C(CH$_2$CH=CH$_2$)$_3$ and 15 mL of AC-2000 were put, followed by stirring at 0° C. for 24 hours. The reaction crude liquid was purified by column chromatography to obtain 11.2 g of compound (20-2).

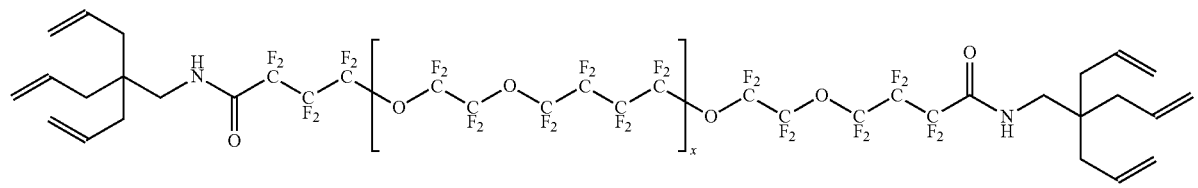

(20-2)

NMR spectrum of compound (20-2):
$^1$H-NMR (300.4 MHz, solvent: CDCl$_3$, reference: TMS) δ (ppm): 6.1 (6H), 5.2 (12H), 3.4 (4H), 2.1 (12H).
$^{19}$F-NMR (282.7 MHz, solvent: CDCl$_3$, reference: CFCl$_3$) δ (ppm): −83 (44F), −87 (44F), −120 (4F), −124 (44F).
Average of x: 11.

Ex. 6-6

1.2 g of compound (10-2) was obtained in the same manner as in Ex. 1-8 except that the compound (2-1) was changed to 1 g of the compound (20-2) obtained in Ex. 6-5.

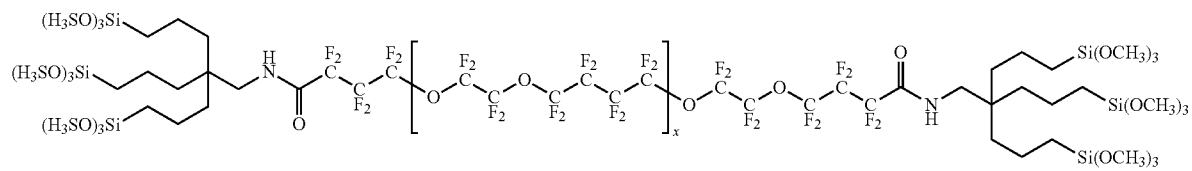

(10-2)

NMR spectrum of compound (10-2):
$^1$H-NMR (300.4 MHz, solvent: CDCl$_3$, reference: TMS) δ (ppm): 3.6 (54H), 3.4 (4H), 1.3 (24H), 0.9 (12H).
$^{19}$F-NMR (282.7 MHz, solvent: CDCl$_3$, reference: CFCl$_3$) δ (ppm): −83 (44F), −87 (44F), −120 (4F), −124 (44F).
Average of x: 11.

Ex. 7 to 13: Production and Evaluation of Article

Using the compound obtained in each of Ex. 1 to 6, or a composition having the compounds obtained in Ex. 1 and 6 (compound (1-1) and compound (10-1) mixed in a mass ratio of 1:1, a substrate was surface-treated to obtain an article in each of Ex. 7 to 13. As the surface treatment method, in each Ex., the following dry coating method and wet coating method were respectively employed. As the substrate, chemically tempered glass was used. With respect to the obtained article, evaluations were conducted by the following methods. The results are shown in Table 1.

(Dry Coating Method)

The dry coating was conducted by using a vacuum deposition apparatus (manufactured by ULVAC Co., VTR 350M) (vacuum deposition method). 0.5 g of the compound obtained in each of Ex. 1 to 6 was filled in a boat made of molybdenum in the vacuum deposition apparatus, and inside of the vacuum deposition apparatus was evacuated of air to a level of at most 1×10$^{-3}$ Pa. The boat on which the compound was placed was heated at a temperature raising rate of at most 10° C./min, and at the time when the vapor deposition rate by a quartz oscillator film thickness meter exceeded 1 nm/sec, the shutter was opened to initiate film deposition on the surface of a substrate. When the film thickness became about 50 nm, the shutter was closed to terminate film deposition on the surface of the substrate. The substrate on which the compound was deposited, was subjected to heat treatment at 200° C. for 30 minutes, followed by washing with dichloropentafluoropropane (manufactured by AGC Inc., AK-225) to obtain an article having a surface layer on the surface of the substrate.

(Wet Coating Method)

The compound obtained in each of Ex. 1 to 6, and C$_4$F$_9$C$_2$H$_5$ (manufactured by 3M, Novec (registered trademark) 7200) as a medium, were mixed to prepare a coating liquid having a solid content concentration of 0.05%. A substrate was dipped in the coating liquid and allowed to stand for 30 minutes, whereupon the substrate was taken out (dip coating method). The coating film was dried at 200° C. for 30 minutes and washed with AK-225, to obtain an article having a surface layer on the surface of the substrate.

(Evaluation Methods)

<Method for Measuring Contact Angle>

The contact angle of about 2 μL of distilled water or n-hexadecane placed on the surface of the surface layer, was measured by using a contact angle measuring apparatus (manufactured by Kyowa Interface Science Co., Ltd., DM-500). Measurements were conducted at five different points on the surface of the surface layer, and the average value was calculated. For the calculation of the contact angle, a method was employed.

<Initial Contact Angle>

With respect to the surface layer, the initial water contact angle and the initial n-hexadecane contact angle were measured by the above-described measuring method. The evaluation standards are as follows.

Initial Water Contact Angle:
⊚ (excellent): at least 115 degrees.
○ (good): at least 110 degrees and less than 115 degrees.
Δ (acceptable): at least 100 degrees and less than 110 degrees,
x (poor): less than 100 degrees.
Initial n-Hexadecane Contact Angle:
⊚ (excellent): at least 66 degrees.
○ (good): at least 65 degrees and less than 66 degrees.
Δ (acceptable): at least 63 degrees and less than 65 degrees.
x (poor): less than 63 degrees.

<Light Resistance>

To the surface layer, by means of a tabletop xenon arc lamp type accelerated light resistance testing machine (manufactured by Toyo Seiki Seisaku-sho, Ltd., SUNTEST XLS+), light (650 W/m$^2$, 300 to 700 nm) was applied at a black panel temperature of 63° C. for 1,000 hours, whereupon the water contact angle was measured. The smaller the decrease in water contact angle after the accelerated light resistance test, the smaller the decrease in performance due to light, and the better the light resistance. The evaluation standards are as follows.
⊚ (excellent): The change in water contact angle after the accelerated light resistance test is at most 2 degrees.
○ (good): The change in water contact angle after the accelerated light resistance test is more than 2 degrees and at most 5 degrees.
Δ (acceptable): The change in water contact angle after the accelerated light resistance test is more than 5 degrees and at most 10 degrees.
x (poor): The change in water contact angle after the accelerated light resistance test is more than 10 degrees.

<Abrasion Resistance (Steel Wool)>

With respect to the surface layer, in accordance with JIS L0849: 2013 (ISO 105-X12: 2001), using a reciprocating traverse testing machine (manufactured by KNT Co.), steel wool Bon Star (#0000) was reciprocated 15,000 times under a pressure of 98.07 kPa at a speed of 320 cm/min, whereupon the water contact angle was measured by the above method. The smaller the decrease in water repellency (water contact angle) after the friction, the smaller the decrease in performance due to friction, and the better the abrasion resistance. The evaluation standards are as follows.
⊚ (excellent): The change in water contact angle after reciprocation of 15,000 times is at most 2 degrees.
○ (good): The change in water contact angle after reciprocation of 15,000 times is more than 2 degrees and at most 5 degrees.
Δ (acceptable): The change in water contact angle after reciprocation of 15,000 times is more than 5 degrees and at most 10 degrees.
x (poor): The change in water contact angle after reciprocation of 15,000 times is more than 10 degrees.

<Chemical Resistance (Alkali Resistance)>

The article was immersed in a 1N aqueous sodium hydroxide solution (pH: 14) for hours, then washed with water and air-dried, whereupon the water contact angle was measured by the above method. The smaller the decrease in water contact angle after the test, the smaller the decrease in performance due to alkali, and the better the alkali resistance. The evaluation standards are as follows.
⊚ (excellent): The change in water contact angle after the alkali resistance test is at most 2 degrees.
○ (good): The change in water contact angle after the alkali resistance test is more than 2 degrees and at most 5 degrees.
Δ (acceptable): The change in water contact angle after the alkali resistance test is more than 5 degrees and at most 10 degrees.
x (poor): The change in water contact angle after the alkali resistance test is more than 10 degrees.

<Chemical Resistance (Salt Water Resistance)>

The salt spray test was carried out in accordance with JIS H8502. That is, the article was exposed to salt atmosphere in a salt spray tester (manufactured by Suga Test Instruments Co., Ltd.) for 300 hours, and then, the water contact angle was measured by the above method. The smaller the decrease in water contact angle after the test, the smaller the decrease in performance due to salt water, and the better the salt water resistance. The evaluation standards are as follows.
⊚ (excellent): The change in water contact angle after the salt spray test is at most 2 degrees.
○ (good): The change in water contact angle after the salt spray test is more than 2 degrees and at most 5 degrees.
Δ (acceptable): The change in water contact angle after the salt spray test is more than 5 degrees and at most 10 degrees.
x (poor): The change in water contact angle after the salt spray test is more than degrees.

<Sliding Resistance>

The dynamic friction coefficient of the surface layer to an artificial skin (manufactured by Idemitsu Technofine Co., Ltd., PBZ13001) was measured by means of a load variation type friction abrasion test system (manufactured by Shinto Scientific Co., Ltd., HHS2000) under conditions of a contact area of 3 cm×3 cm and a load of 0.98N. The larger the dynamic friction coefficient, the better the sliding resistance. The evaluation standards are as follows.
⊚ (excellent): The dynamic friction coefficient is at least 0.6.
○ (good): The dynamic friction coefficient is at least 0.5 and less than 0.6.
Δ (acceptable): The dynamic friction coefficient is at least 0.4 and less than 0.5.
x (poor): The dynamic friction coefficient is less than 0.4.

<Fingerprint Stain Removability>

An artificial fingerprint liquid (liquid consisting of oleic acid and squalene) was deposited on a flat surface of a silicon rubber plug, and then, extra oil was wiped off by a nonwoven fabric (manufactured by Asahi Kasei Corporation, BEMCOT (registered trademark) M-3), to prepare a stamp for fingerprint. The fingerprint stamp was placed on the surface layer and pressed under a load of 9.8 N for 10 seconds. The haze at a portion having a fingerprint put, was measured by a haze meter and taken as an initial value. With respect to the portion having a fingerprint put, using a reciprocating traverse testing machine (manufactured by KNT Co.) having tissue paper attached, wiping was carried out under a load of 4.9 N. The value of haze was measured every one reciprocation for wiping, and the number of wiping times until the haze became at most 10% of the initial value, was measured. The smaller the number of wiping times, the easier the removal of fingerprint stain, and the better the fingerprint stain removability. The evaluation standards are as follows.
⊚ (excellent): The number of wiping times is at most 3 times.
○ (good): The number of wiping times is from 4 to 5 times.
Δ (acceptable): The number of wiping times is from 6 to 8 times.
x (poor): The number of wiping times is at least 9 times.

TABLE 1

| | | | Ex. | | | | | | |
|---|---|---|---|---|---|---|---|---|---|
| | | | 7 | 8 | 9 | 10 | 11 | 12 | 13 |
| | | | | | | Fluorinated ether compound | | | |
| | | | Compound (1-1) | Compound (1-2) | Compound (1-3) | Compound (1-4) | Compound (10-1) | Compound (10-2) | Compound (1-1) + Compound (10-1) |
| Dry coating | Initial contact angle | Water | ⊚ | ⊚ | ⊚ | ⊚ | ⊚ | ⊚ | ⊚ |
| | | n-Hexadecane | ⊚ | ⊚ | ⊚ | ⊚ | ⊚ | ⊚ | ⊚ |
| | Light resistance | | ○ | ○ | ○ | ○ | Δ | Δ | ○ |
| | Abrasion resistance | | ⊚ | ○ | ○ | ⊚ | X | Δ | ⊚ |
| Wet coating | Initial contact angle | Water | ⊚ | ⊚ | ⊚ | ⊚ | ⊚ | ⊚ | ⊚ |
| | | n-Hexadecane | ⊚ | ⊚ | ⊚ | ⊚ | ⊚ | ⊚ | ⊚ |
| | Light resistance | | ○ | ○ | ○ | ○ | Δ | ○ | ○ |
| | Abrasion resistance | | ⊚ | ○ | ○ | ⊚ | X | Δ | ⊚ |
| | Chemical resistance | Alkali resistance | ○ | ○ | ○ | ○ | Δ | Δ | ○ |
| | | Salt water resistance | ⊚ | ○ | ○ | ⊚ | Δ | Δ | ⊚ |
| | Sliding resistance | | ⊚ | ○ | ○ | ⊚ | X | X | ○ |
| | Fingerprint stain removability | | ○ | ⊚ | ⊚ | ○ | ⊚ | ○ | ⊚ |

It was confirmed that in Ex. 7 to 10 in which the present compound was used, the initial water/oil repellency, light resistance, abrasion resistance, chemical resistance, sliding resistance and fingerprint stain removability were excellent.

In Ex. 11 and 12 in which a conventional fluorinated ether compound was used, abrasion resistance, lubricity, light resistance and chemical resistance were inferior. Whereas in Ex. 13 in which the present composition comprising the present compound and a conventional fluorinated ether compound in combination was used, sliding resistance and fingerprint stain removability improved as compared with Ex. 11, and sufficient effects of the present compound were exhibited.

Further, various fluorinated ether compounds (the present compounds) were prepared. Preparation Examples are shown below.

Ex. 14

Ex. 14-1

Into a 100 mL metal reactor, 20 g of the compound (11-1) obtained in Ex. 1-1 was put, and 19.1 g of $CF_2=CFOCF_2CF_2CF_3$ was put, followed by stirring at 180° C. for 300 hours. The resulting organic phase was concentrated and purified by distillation to obtain 5.9 g of compound (33-1).

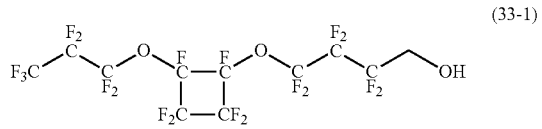

(33-1)

NMR spectrum of compound (33-1):
$^1$H-NMR (300.4 MHz, solvent: $CDCl_3$, reference: TMS) δ (ppm): 4.1 (2H).
$^{19}$F-NMR (282.7 MHz, solvent: $CDCl_3$, reference: $CFCl_3$) δ (ppm): −81 (3F), −82 (4F), −123 (2F), −126 (2F), −128 (4F), −129 (2F), −137 (2F).

Ex. 14-2

12 g of compound (33-2) was obtained in the same manner as in Ex. 1-3 except that the compound (23-1) was changed to 4.9 g of the compound (33-1) obtained in Ex. 14-1 and that the amount of potassium carbonate was changed to 0.5 g.

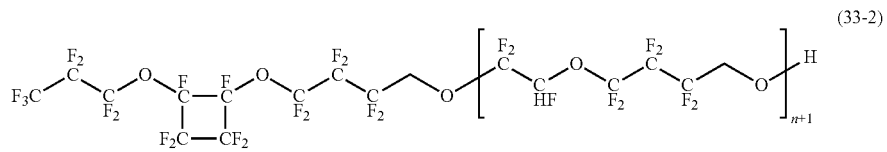

(33-2)

NMR spectrum of compound (33-2):
$^1$H-NMR (300.4 MHz, solvent: $CDCl_3$, reference: TMS) δ (ppm): 6.0 (1 OH), 4.6 (20H), 4.1 (2H).
$^{19}$F-NMR (282.7 MHz, solvent: $CDCl_3$, reference: $CFCl_3$) δ (ppm): −81 (3F), −82 (24F), −90 (20F), −120 (20F), −123 (2F), −126 (22F), −128 (4F), −129 (2F), −137 (2F), −144 (10F).
Average of n+1: 10.

Ex. 14-3

11 g of compound (33-3) was obtained in the same manner as in Ex. 1-4 except that the compound (4-1) was changed to 10 g of the compound (33-2) obtained in Ex. 14-2, the amount of the sodium fluoride powder was changed to 0.6 g and that the amount of $CF_3CF_2CF_2OCF(CF_3)COF$ was changed to 5 g.

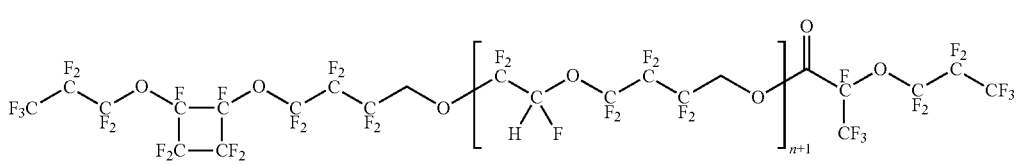
(33-3)

NMR spectrum of compound (33-3):
$^1$H-NMR (300.4 MHz, solvent: CDCl$_3$, reference: TMS) δ (ppm): 6.0 (1 OH), 5.0 (2H), 4.6 (20H).
$^{19}$F-NMR (282.7 MHz, solvent: CDCl$_3$, reference: CFCl$_3$) δ (ppm): −81 (6F), −82 (26F), −83 (3F), −90 (20F), −119 (2F), −120 (20F), −126 (22F), −128 (4F), −129 (4F), −132 (1F), −137 (2F), −144 (10F).
Average of n+1: 10.

Ex. 14-4

12 g of compound (33-4) was obtained in the same manner as in Ex. 1-5 except that the compound (4-2) was changed to 10 g of the compound (33-3) obtained in Ex. 14-3.

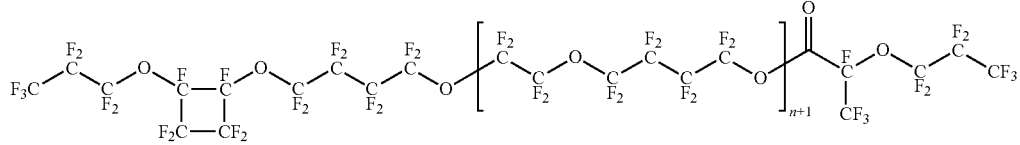
(33-4)

NMR spectrum of compound (33-4):
$^{19}$F-NMR (282.7 MHz, solvent: CDCl$_3$, reference: CFCl$_3$) δ (ppm): −81 (6F), −82 (6F), −83 (3F), −84 (42F), −90 (40F), 124 (44F), −128 (4F), −129 (4F), −132 (1F), −137 (2F).
Average of n+1: 10.

Ex. 14-5

11 g of the compound (33-5) was obtained in the same manner as in Ex. 1-6 except that the compound (4-3) was changed to 12 g of the compound (33-4) obtained in Ex. 14-4.

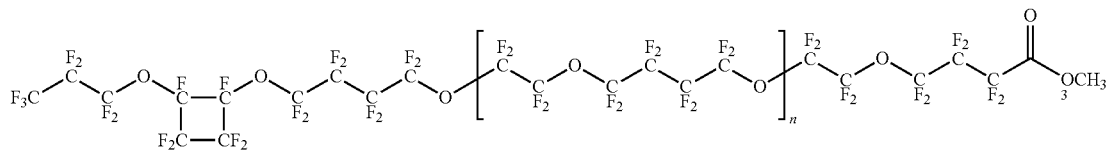
(33-5)

NMR spectrum of compound (33-5):
$^1$H-NMR (300.4 MHz, solvent: CDCl$_3$, reference: TMS) δ (ppm): 4.2 (3H).
$^{19}$F-NMR (282.7 MHz, solvent: CDCl$_3$, reference: CFCl$_3$) δ (ppm): −81 (3F), −82 (4F), −84 (40F), −90 (40F), −118 (2F), 124 (42F), −128 (4F), −129 (2F), −137 (2F).
Average of n: 9.

Ex. 14-6

12 of the compound (33-6) was obtained in the same manner as in Ex. 1-7 except that the compound (4-4) was changed to 12 g of the compound (33-5) obtained in Ex. 14-5.

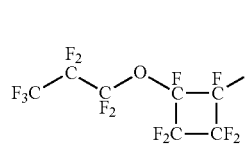 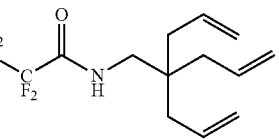

(33-6)

NMR spectrum of compound (33-6):
$^{1}$H-NMR (300.4 MHz, solvent: CDCl$_3$, reference: TMS) δ (ppm): 6.1 (3H), 5.2 (6H), 3.4 (2H), 2.1 (6H).

$^{19}$F-NMR (282.7 MHz, solvent: CDCl$_3$, reference: CFCl$_3$) δ (ppm): −81 (3F), −82 (4F), −84 (40F), −90 (40F), −120 (2F), 124 (42F), −128 (4F), −129 (2F), −137 (2F).

Average of n: 9.

Ex. 14-7

1.1 of the compound (33-7) was obtained in the same manner as in Ex. 1-8 except that the compound (2-1) was changed to 1 g of the compound (33-6) obtained in Ex. 14-6.

water, and the resulting organic layer was recovered. The solvent and the like were distilled off under reduced pressure to obtain 9.9 g of compound (34-1).

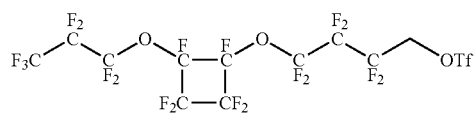

(34-1)

wherein OTf represents —OSO$_2$CF$_3$.

NMR spectrum of compound (34-1):
$^{1}$H-NMR (300.4 MHz, solvent: CDCl$_3$, reference: TMS) δ (ppm): 5.0 (2H).

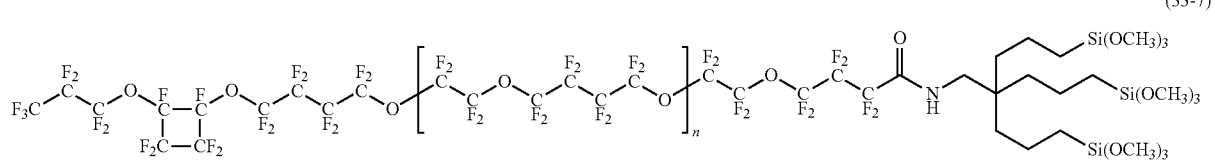

(33-7)

NMR spectrum of compound (33-7):
$^{1}$H-NMR (300.4 MHz, solvent: CDCl$_3$, reference: TMS) δ (ppm): 3.6 (27), 3.4 (2H), 1.3 (12H), 0.9 (6H).
$^{19}$F-NMR (282.7 MHz, solvent: CDCl$_3$, reference: CFCl$_3$) δ (ppm): −81 (3F), −82 (4F), −84 (40F), −90 (40F), −120 (2F), 124 (42F), −128 (4F), −129 (2F), −137 (2F).
Average of n: 9.

Ex. 15

Ex. 15-1

Into a 50 mL eggplant flask, 10 g of the compound (33-1) obtained in Ex. 14-1, 15.6 g of trifluoromethanesulfonic acid anhydride, 5.6 g of triethylamine and 10 g of 1,3-bistrifluoromethylbenzene were mixed and reacted at 40° C. for 3 hours. The crude liquid after the reaction was washed with $^{19}$F-NMR (282.7 MHz, solvent: CDCl$_3$, reference: CFCl$_3$) δ (ppm): −74 (3F), −81 (3F), −82 (4F), −119 (2F), −126 (2F), −128 (4F), −129 (2F), −137 (2F).

Ex. 15-2

Into a 50 mL eggplant flask, 10 g of the compound (34-1) obtained in Ex. 15-1, 13.1 g of cesium carbonate, 59 g of 1,3-bistrifluoromethylbenzene and 59 g of FLUOROLINK (registered trademark) D4000 manufactured by Solvay Solexis were mixed and reacted at 80° C. for 6 hours. The crude liquid after the reaction was washed with hydrochloric acid, and the resulting organic layer was recovered. The solvent and the like were distilled off under reduced pressure and purified by column chromatography to obtain 20 g of compound (34-2).

In the following compounds (34-2) to (34-7), -[CF$_{2O}$]$_{c1}$—[CF$_2$CF$_{2O}$]$_{c2}$— represents a random copolymer chain of C1 (CF$_2$O) and C2 (CF$_2$CF$_2$O).

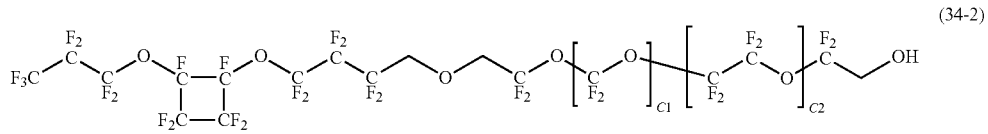

(34-2)

NMR spectrum of compound (34-2):
$^1$H-NMR (300.4 MHz, solvent: CDCl$_3$, reference: TMS) δ (ppm): 5.0 (2H), 4.2 (2H), 3.9 (2H).
$^{19}$F-NMR (282.7 MHz, solvent: CDCl$_3$, reference: CFCl$_3$) δ (ppm): −55 (44F), −80 (2F), −81 (5F), −82 (4F), −90 (96F), −119 (2F), −126 (2F), −128 (4F), −129 (2F), −137 (2F).
Average of C1: 22. Average of C2: 24.

Ex. 15-3

12 g of compound (34-3) was obtained in the same manner as in Ex. 1-5 except that the compound (4-2) was changed to 20 g of the compound (34-2) obtained in Ex. 15-2.

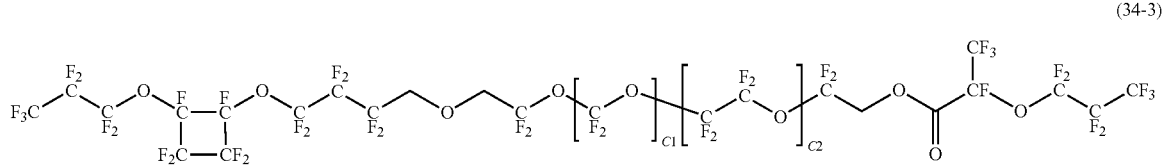

(34-3)

NMR spectrum of compound (34-3):
$^1$H-NMR (300.4 MHz, solvent: CDCl$_3$, reference: TMS) δ (ppm): 5.0 (2H), 4.7 (2H), 4.2 (2H).
$^{19}$F-NMR (282.7 MHz, solvent: CDCl$_3$, reference: CFCl$_3$) δ (ppm): −55 (44F), −80 (2F), −81 (8F), −82 (6F), −83 (3F), −90 (96F), −119 (2F), −126 (2F), −128 (4F), −129 (4F), −132 (1F), −137 (2F).
Average of C1: 22. Average of C2: 24.

Ex. 15-4

12 g of compound (34-4) was obtained in the same manner as in Ex. 1-5 except that the compound (4-2) was changed to 12 g of the compound (34-3) obtained in Ex. 15-3.

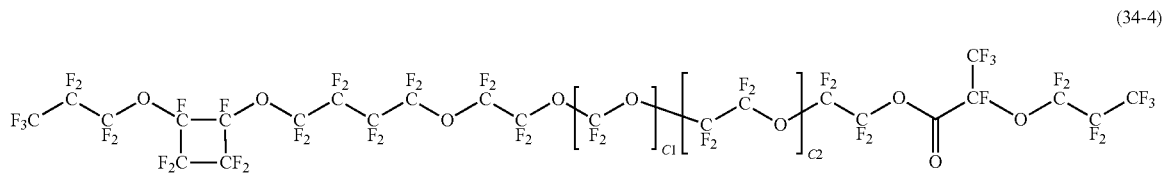

(34-4)

NMR spectrum of compound (34-4):
$^{19}$F-NMR (282.7 MHz, solvent: CDCl$_3$, reference: CFCl$_3$) δ (ppm): −55 (44F), −81 (6F), −82 (8F), −83 (3F), −90 (100F), −124 (4F), −128 (4F), −129 (4F), −132 (1F), −137 (2F).
Average of C1: 22. Average of C2: 24.

Ex. 15-5

19 g of compound (34-5) was obtained in the same manner as in Ex. 1-6 except that the compound (4-3) was changed to 20 g of the compound (34-4) obtained in Ex. 15-4.

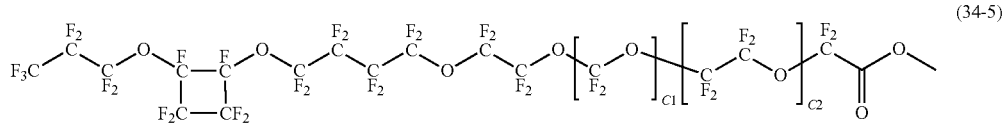

(34-5)

NMR spectrum of compound (34-5):
¹H-NMR (300.4 MHz, solvent: CDCl₃, reference: TMS) δ (ppm): 4.2 (3H).
¹⁹F-NMR (282.7 MHz, solvent: CDCl₃, reference: CFCl₃) δ (ppm): −55 (44F), −80 (2F), −81 (3F), −82 (6F), −90 (96F), −124 (4F), −128 (4F), −129 (2F), −137 (2F).
Average of C1: 22. Average of C2: 24.

Ex. 15-6

15 of compound (34-6) was obtained in the same manner as in Ex. 1-7 except that the compound (4-4) was changed to 19 g of the compound (34-5) obtained in Ex. 15-5.

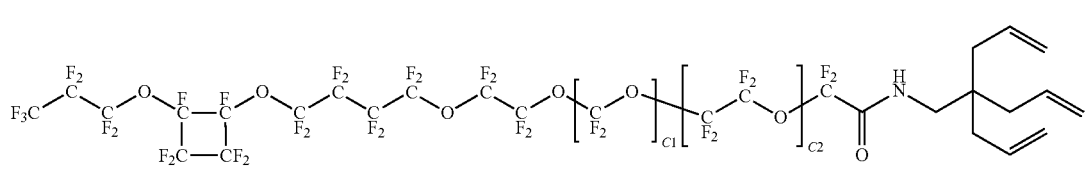

(34-6)

NMR spectrum of compound (34-6):
¹H-NMR (300.4 MHz, solvent: CDCl₃, reference: TMS) δ (ppm): 6.1 (3H), 5.2 (6H), 3.4 (2H), 2.1 (6H).
¹⁹F-NMR (282.7 MHz, solvent: CDCl₃, reference: CFCl₃) δ (ppm): −55 (44F), −79 (2F), −81 (3F), −82 (6F), −90 (96F), −124 (4F), −128 (4F), −129 (2F), −137 (2F).
Average of C1: 22. Average of C2: 24.

Ex. 15-7

1.1 g of compound (34-7) was obtained in the same manner as in Ex. 1-8 except that the compound (2-1) was changed to 1 g of the compound (34-6) obtained in Ex. 15-6.

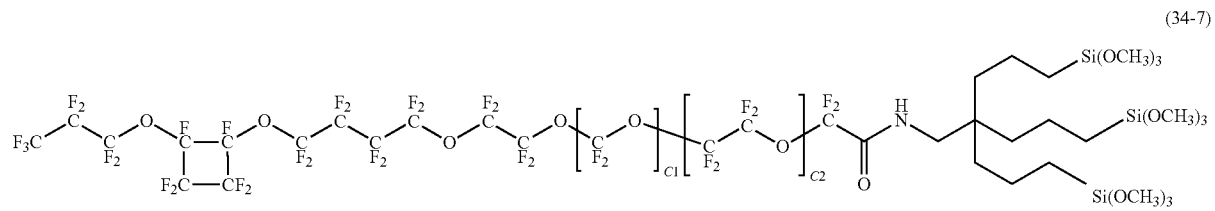

(34-7)

NMR spectrum of compound (34-7):
¹H-NMR (300.4 MHz, solvent: CDCl₃, reference: TMS) δ (ppm): 3.6 (27), 3.4 (2H), 1.3 (12H), 0.9 (6H).
¹⁹F-NMR (282.7 MHz, solvent: CDCl₃, reference: CFCl₃) δ (ppm): −55 (44F), −79 (2F), −81 (3F), −82 (6F), −90 (96F), −124 (4F), −128 (4F), −129 (2F), −137 (2F).
Average of C1: 22. Average of C2: 24.

Ex. 16

Ex. 16-1

Into a 200 mL eggplant flask, 10.0 g of 1,4-cyclohexanedimethanol and 19.2 g of potassium carbonate were put, followed by stirring at 120° C., and 192.8 g of the compound (11-1) obtained in Ex. 1-1 was added, followed by stirring at 120° C. for 2 hours. The temperature in the eggplant flask was adjusted to 25° C., and 100 g each of AC-2000 and hydrochloric acid were put, followed by liquid separation, and the organic phase was concentrated. The obtained reaction crude liquid was purified by column chromatography to obtain 96.6 g of compound (35-1).

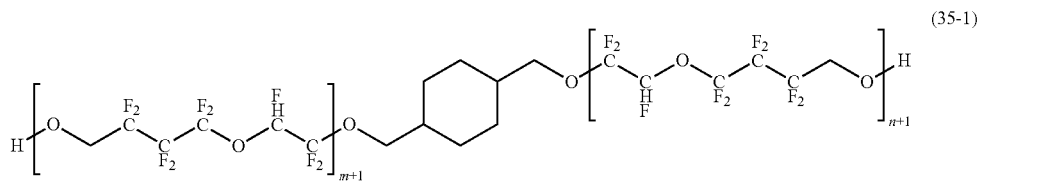

(35-1)

NMR spectrum of compound (35-1):
$^1$H-NMR (300.4 MHz, solvent: CDCl$_3$, reference: TMS) δ (ppm): 6.0 (1 OH), 4.6 (16H), 4.1 (4H), 3.3 (4H), 1.9 (2H), 1.5 (8H).
$^{19}$F-NMR (282.7 MHz, solvent: CDCl$_3$, reference: CFCl$_3$) δ (ppm): −82 (20F), −90 (20F), −120 (16F), −123 (4F), −126 (20F), −144 (10F).
Average of (m+1)+(n+1): 10.

Ex. 16-2

100.8 g of compound (35-2) was obtained in the same manner as in Ex. 1-4 except that the compound (4-1) was changed to 90 g of the compound (35-1) obtained in Ex. 16-1, that the amount of the sodium fluoride powder was changed to 5.4 g and that the amount of CF$_3$CF$_2$CF$_2$OCF(CF$_3$)COF was changed to 85.8 g.

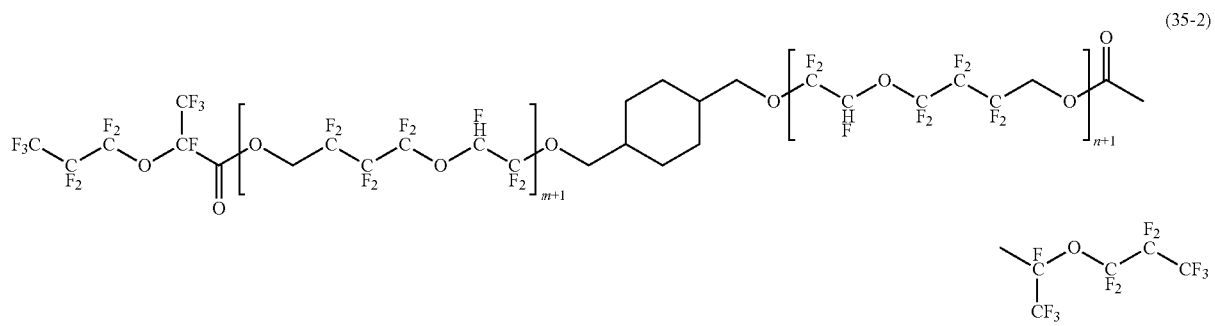
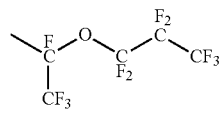

(35-2)

NMR spectrum of compound (35-2):
$^1$H-NMR (300.4 MHz, solvent: CDCl$_3$, reference: TMS) δ (ppm): 6.0 (1 OH), 5.0 (4H), 4.6 (16H), 3.3 (4H), 1.9 (2H), 1.5 (8H).
$^{19}$F-NMR (282.7 MHz, solvent: CDCl$_3$, reference: CFCl$_3$) δ (ppm): −81 (6F), −82 (24F), −83 (6F), −90 (20F), −119 (4F), −120 (16F), −126 (20F), −129 (4F), −132 (2F), −144 (10F).
Average of (m+1)+(n+1): 10.

Ex. 16-3

45.3 g of compound (35-3) was obtained in the same manner as in Ex. 1-5 except that the compound (4-2) was changed to 40 g of the compound (35-2) obtained in Ex. 16-2 and that the time over which the CFE-419 solution of the compound 5-2 was charged was changed to 8 hours.

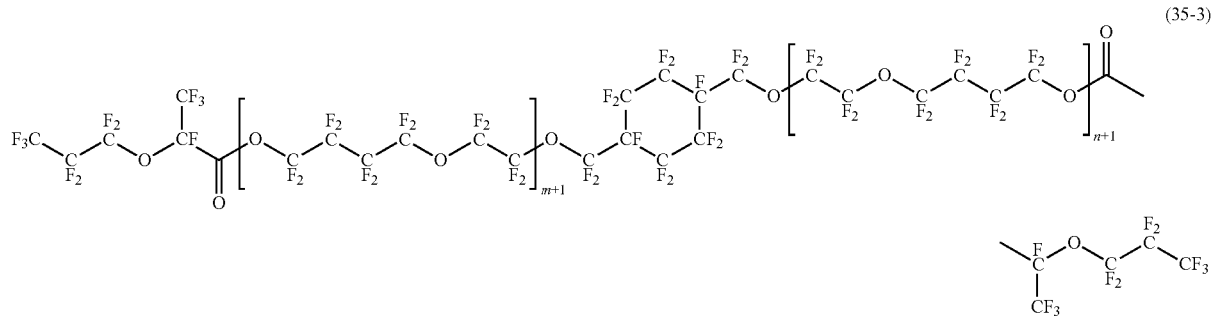

(35-3)

NMR spectrum of compound (35-3):

$^{19}$F-NMR (282.7 MHz, solvent: CDCl$_3$, reference: CFCl$_3$) δ (ppm): −81 (6F), −82 (4F), −83 (6F), −84 (40F), −90 (40F), −93 (4F), −124 (20F), −127 (8F), −129 (4F), −132 (2F), −184 (2F).

Average of (m+1)+(n+1): 10.

Ex. 6-4

Into a 50 mL eggplant flask, 40.0 g of the compound (35-3) obtained in Ex. 16-3, 3.4 g of sodium fluoride and 40 mL of AC-2000 were put, followed by stirring in an ice bath. 2.6 g of methanol was put, followed by stirring at 25° C. for 1 hour. The mixture was subjected to filtration, and the filtrate was purified by column chromatography to obtain 31.3 g of compound (35-4).

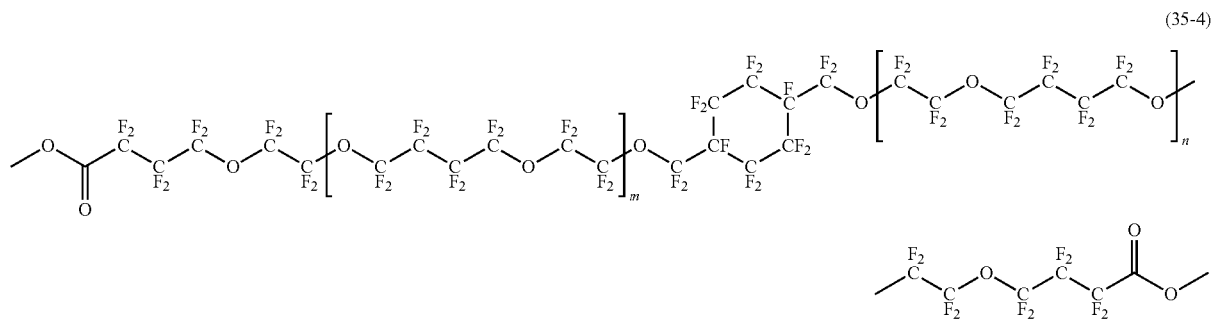

(35-4)

NMR spectrum of compound (35-4):
$^1$H-NMR (300.4 MHz, solvent: CDCl$_3$, reference: TMS) δ (ppm): 4.2 (6H).
$^{19}$F-NMR (282.7 MHz, solvent: CDCl$_3$, reference: CFCl$_3$) δ (ppm): −84 (36F), −90 (40F), −93 (4F), −118 (4F), −124 (16F), −127 (8F), −184 (2F).
Average of m+n: 8.

Ex. 16-5

Into a 50 mL eggplant flask, 20 g of the compound (35-4) obtained in Ex. 16-4, 2.3 g of H2 NCH$_2$C(CH$_2$CH=CH$_2$)$_3$ and 15 mL of AC-2000 were put, followed by stirring at 0° C. for 24 hours. The reaction crude liquid was purified by column chromatography to obtain 12.7 g of compound (35-5).

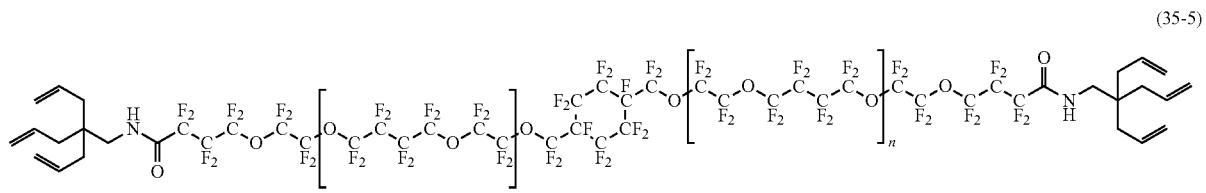

(35-5)

NMR spectrum of compound (35-5):
$^1$H-NMR (300.4 MHz, solvent: CDCl$_3$, reference: TMS) δ (ppm): 6.1 (6H), 5.2 (12H), 3.4 (4H), 2.1 (12H).
$^{19}$F-NMR (282.7 MHz, solvent: CDCl$_3$, reference: CFCl$_3$) δ (ppm): −84 (36F), −90 (40F), −93 (4F), −120 (4F), −124 (16F), −127 (8F), −184 (2F).
Average of m+n: 8.

Ex. 16-6

1.1 g of compound (35-6) was obtained in the same manner as in Ex. 1-8 except that the compound (2-1) was changed to 1 g of the compound (35-5) obtained in Ex. 16-5.

(35-6)

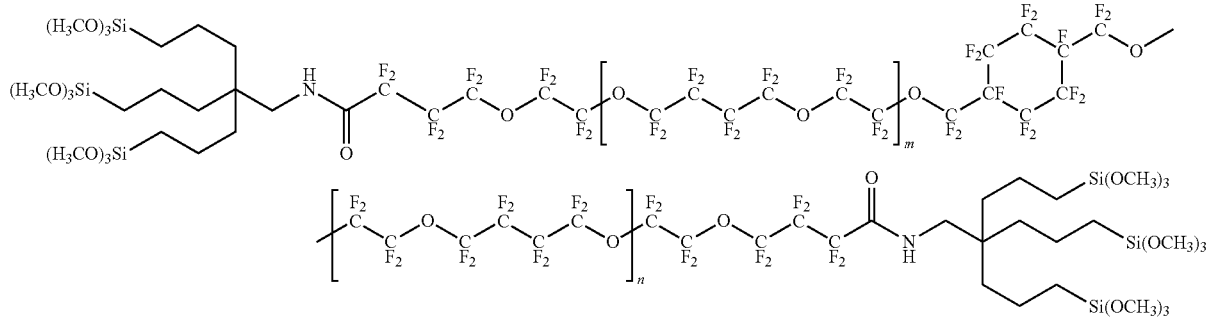

NMR spectrum of compound (35-6):
$^1$H-NMR (300.4 MHz, solvent: CDCl$_3$, reference: TMS) δ (ppm): 3.6 (54H), 3.4 (4H), 1.3 (24H), 0.9 (12H).
$^{19}$F-NMR (282.7 MHz, solvent: CDCl$_3$, reference: CFCl$_3$) δ (ppm): −84 (36F), −90 (40F), −93 (4F), −120 (4F), −124 (16F), −127 (8F), −184 (2F).
Average of m+n: 8.

INDUSTRIAL APPLICABILITY

The fluorinated ether compound of the present invention is useful for various applications for which it is required to impart lubricity and water/oil repellency. For example, it may be used for a display input device such as a touch panel, surface protective coating on a transparent glass or transparent plastic member, kitchen antifouling coating, water repellent moisture proof coating or antifouling coating on electronic device, a heat exchanger or a battery, toiletry antifouling coating, coating on a member which requires liquid repellency while conducting electricity, water repellent/waterproof/water sliding coating on a heat exchanger, or a surface low friction coating on the inside of a vibrating strainer or a cylinder, etc. More specific examples of application include a front protective plate, an antireflection plate, a polarizing plate, an antiglare plate or a surface thereof having an antireflection film, of a display, an apparatus having a display input device of which the screen is operated by human fingers or hands, such as a touch panel sheet or a touch panel display of an apparatus such as a mobile phone or a personal digital assistant, a decorative building material for restroom, bathroom, lavatory, kitchen and the like, waterproof coating for a wiring board, water repellent/waterproof coating on a heat exchanger, water repellent coating on a solar cell, waterproof/water repellent coating on a printed wiring board, waterproof/water repellent coating for an electronic equipment casing or an electronic member, insulating property-improving coating on a power transmission line, waterproof/water repellent coating on a filter, waterproof coating on an electromagnetic wave absorption material or a sound-absorbing material, antifouling coating for bathroom, kitchen instrument and toiletry, water repellent/waterproof/water sliding coating on a heat exchanger, surface low-friction coating on the inside of a vibrating strainer or a cylinder, surface protective coating on a machine component, a vacuum apparatus component, a bearing component, an automobile component, an industrial tool, etc.

This application is a continuation of PCT Application No. PCT/JP2020/003794, filed on Jan. 31, 2020, which is based upon and claims the benefit of priority from Japanese Patent Application No. 2019-022079 filed on Feb. 8, 2019 and Japanese Patent Application No. 2019-220995 filed on Dec. 6, 2019. The contents of those applications are incorporated herein by reference in their entireties.

What is claimed is:
1. A fluorinated ether compound of formula (1A):

$$[R^f-]_{a1}Q^1[-T]_{b1} \quad (1A)$$

wherein $R^f$ is a monovalent group the bond terminal of which is constituted by a carbon atom, which comprises a first partial structure of formula (1) and a second partial structure of formula (2):

wherein $R^{f12}$ is a C$_{1-6}$ fluoroalkylene group, and $R^{f13}$ is a group having a fluorinated cyclic structure which may have a hetero atom, and wherein $R^f$ comprises at least five first partial structures or comprises at least two second partial structures, and when there are two or more $R^f$, the two or more $R^f$ may be the same or different, $Q^1$ is a (a1+b1) valent linking group,
T is —$R^{f6}$, —Ar, —OR$^{10}$, —SR$^{10}$, —NOR$^{10}$, —C(=O)R$^{10}$, —N(R$^{10}$)$_2$, —N$^+$(R$^{10}$)$_3$X$^3$, —C≡N, —C(=NR$^{10}$)—R$^{10}$, —N$^+$≡N, —N=NR$^{10}$, —C(=O)OR$^{10}$, —C(=O)OX$^2$, —C(=O)OX$^4$, —C(=O)OC(=O)R$^{10}$, —SO$_2$R$^{10}$, —SO$_3$H, —SO$_3$X$^2$, —O—P(=O)(—OR$^{10}$)$_2$, —O—P(=O)(—OR$^{10}$)(—OX$^2$), —N=C=O, —Si(R)$_{3-c}$(L)$_c$, —C(R$^{10}$)=C(R$^{10}$)$_2$, —C=C(R$^{10}$), —C(=O)N(R$^{10}$)$_2$, —N(R$^{10}$)C(=O)R$^{10}$, —Si(R$^{10}$)$_2$—O—Si(R$^{10}$)$_3$, —NH—C(=O)R$^{10}$, —C(=O)NHR$^{10}$, —I, or a group containing

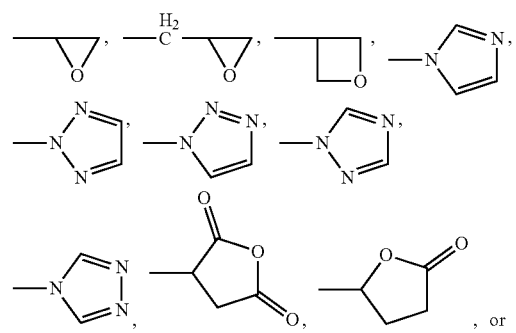

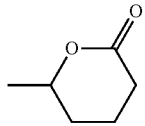

R^{f6} is a $C_{1-6}$ fluoroalkyl group, $R^{10}$ is a hydrogen atom, a $C_{1-6}$ alkyl or fluoroalkyl group, or an aryl group which may have a substituent, and when there are two or more $R^{10}$, the two or more $R^{10}$ may be the same or different, Ar is an aryl group which may have a substituent, $X^2$ is an alkali metal ion or an ammonium ion, $X^3$ is a halide ion, $X^4$ is a halogen atom, R is an alkyl group, L is a hydrolyzable group or a hydroxy group, and the two or more L in T may be the same or different, a1 is an integer of at least 1, b1 is an integer of at least 2, and c is 2 or 3, provided that the two or more T may be the same or different.

2. The fluorinated ether compound according to claim 1, wherein $R^f$ is a group represented by the following formula (g1a):

$$R^{f1}—(OR^{f2})_m(OR^{f3})_n— \quad (g1a)$$

wherein $R^{f1}$ is a $C_{1-20}$ fluoroalkyl group or a monovalent fluorinated hydrocarbon group having a fluorinated cyclic structure, $R^{f2}$ is a $C_{1-6}$ fluoroalkylene group provided that to the carbon atom at the terminal on the $Q^1$ side of $R^{f2}$ bonded to $Q^1$, at least one fluorine atom is bonded, $R^{f3}$ is a bivalent fluorinated hydrocarbon group having a fluorinated cyclic structure (provided that to the carbon atom at the terminal on the $Q^1$ side of $R^{f3}$ bonded to $Q^1$, at least one fluorine atom is bonded), n is an integer of from 0 to 500 when $R^{f1}$ has a fluorinated cyclic structure, or an integer of from 1 to 500 when $R^{f1}$ has no fluorinated cyclic structure, and when n is at least 2, $(OR^{f3})_n$ may consist of two or more types of $OR^{f3}$, when n is 0, m is an integer of from 5 to 500, and when n is at least 1, m is an integer of from 2 to 500, provided that when m is at least 2, $(OR^{f2})_m$ may consist of two or more types of $OR^{f2}$, and the bonding order of m $(OR^{f2})$ and n $(OR^{f3})$ is not limited.

3. The fluorinated ether compound according to claim 1, wherein $Q^1$ is a group represented by the formula (g2-1) provided that a1=d1+d3 and b1=d2+d4, a group represented by the formula (g2-2) provided that a1=e1 and b1=e2, a group represented by the formula (g2-3) provided that a1=1 and b1=2), a group represented by the formula (g2-4) provided that a1=h1 and b1=h2, a group represented by the formula (g2-5) provided that a1=i1 and b1=i2, or a group represented by the formula (g2-7) provided that a1=1 and b1=i3;

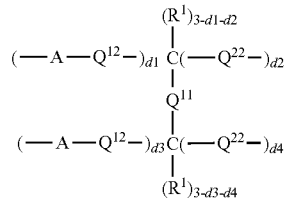

$(-A-Q^{12}-)_{e1}C(R^2)_{4-e1-e2}(-Q^{22}-)_{e2}$ (g2-2)

$-A-Q^{13}-N(-Q^{23}-)_2$ (g2-3)

$(-A-Q^{14}-)_{h1}Z(-Q^{24}-)_{h2}$ (g2-4)

$(-A-Q^{15}-)_{i1}Si(R^3)_{4-i1-i2}(-Q^{25}-)_{i2}$ (g2-5)

$-A-Q^{12}-CH(-Q^{22}-)-Si(R^3)_{3-i3}(-Q^{25}-)_{i3}$ (g2-7)

wherein in the formulae (g2-1) to (g2-5) and (g2-7), the A side is bonded to $R^f$, and the $Q^{22}$, $Q^{23}$, $Q^{24}$, $Q^{25}$ $Q^{26}$ side is bonded to T, A is a single bond, —C(O)NR^6—, —C(O)—, —OC(O)O—, —NHC(O)O—, —NHC(O)NR^6—, —O— or —SO_2NR^6—, $Q^{11}$ is a single bond, —O—, an alkylene group or a group having —C(O)NR^6—, —C(O)—, —NR^6— or —O— between carbon atoms of an alkylene group having at least 2 carbon atoms, $Q^{12}$ is a single bond, an alkylene group or a group having —C(O)NR^6—, —C(O)—, —NR^6— or —O— between carbon atoms of an alkylene group having at least 2 carbon atoms, and when $Q^1$ has two or more $Q^{12}$, the two or more $Q^{12}$ nay be the same or different, $Q^{13}$ is a single bond (provided that A is —C(O)—), an alkylene group, a group having —C(O)NR^6—, —C(O)—, —NR^6— or —O— between carbon atoms of an alkylene group having at least 2 carbon atoms, or an alkylene group having —C(O)— at the terminal on the N side, $Q^{14}$ is $Q^{12}$ when the atom in Z to which $Q^{14}$ is bonded is a carbon atom, or $Q^{13}$ when the atom in Z to which $Q^{14}$ is bonded is a nitrogen atom, and when $Q^1$ has two or more $Q^{14}$, the two or more $Q^{14}$ nay be the same or different, $Q^{15}$ is an alkylene group or a group having —C(O)NR^6—, —C(O)—, —NR^6— or —O— between carbon atoms of an alkylene group having at least 2 carbon atoms, and when $Q^1$ has two or more $Q^{15}$ the two or more $Q^{15}$ nay be the same or different, $Q^{22}$ is an alkylene group, a group having —C(O)NR^6—, —C(O)—, —NR^6— or —O— between carbon atoms of an alkylene group having at least 2 carbon atoms, an alkylene group having —C(O)NR^6—, —C(O)—, —NR^6— or —O— at the terminal on the side not bonded to T, or a group having —C(O)NR^6—, —C(O)—, —NR^6— or —O— between carbon atoms of an alkylene group having at least 2 carbon atoms and having —C(O)NR^6—, —C(O)—, —NR^6— or —O— at the terminal on the side not bonded to T, and when $Q^1$ has two or more $Q^{22}$, the two or more $Q^{22}$ may be the same or different, $Q^{23}$ is an alkylene group or a group having —C(O)NR^6—, —C(O)—, —NR^6— or —O— between carbon atoms of an alkylene group having at least 2 carbon atoms, and the two $Q^{23}$ may be the same or different, $Q^{24}$ is $Q^{22}$ when the atom in Z to which $Q^{24}$ is bonded is a carbon atom, or $Q^{23}$ when the atom in Z to which $Q^{24}$ is bonded is a nitrogen atom, and when $Q^1$ has two or more $Q^{24}$, the two or more $Q^{24}$ may be the same or different, $Q^{25}$ is an alkylene group or a group having —C(O)NR$^6$—, —C(O)—, —NR$^6$— or —O— between carbon atoms of an alkylene group having at least 2 carbon atoms, and when $Q^1$ has two or more $Q^{25}$, the two or more $Q^{25}$ may be the same or different, Z is a group having a (a1+b1) valent cyclic structure having a carbon atom or a nitrogen atom to which $Q^{14}$ is directly bonded and having a carbon atom or a nitrogen atom to which $Q^{24}$ is directly bonded, $R^1$ is a hydrogen atom or an alkyl group, and when $Q^1$ has two or more $R^1$, the two or more $R^1$ may be the same or different, $R^2$ is a hydrogen atom, a hydroxy group, an alkyl group or an acyloxy group, $R^3$ is an alkyl group, $R^6$ is a hydrogen atom, a $C_{1-6}$ alkyl group or a phenyl group, d1 is an integer of from 0 to 3, d2 is an integer of from 0 to 3, and d1+d2 is an integer of from 1 to 3, d3 is an integer of from 0 to 3, d4 is an integer of from 0 to 3, and d3+d4 is an integer of from 1 to 3, d1+d3 is an integer of from 1 to 5 in $Q^1$, d2+d4 is an integer of from 2 to 5 in $Q^1$, e1+e2 is 3 or 4, e1 is an integer of from 1 to 3 in $Q^1$, e2 is an integer of from 2 to 3 in $Q^1$, h1 is an integer of at least 1 in $Q^1$, h2 is an integer of at least 2, i1+i2 is 3 or 4, i1 is an integer of from 1 to 3 in $Q^1$, i2 is an integer of from 2 to 3 in $Q^1$, and i3 is 2 or 3.

4. The fluorinated ether compound according to claim 1, wherein the fluorinated cyclic structure is a four-membered ring.

5. The fluorinated ether compound according to claim 1, which has a number average molecular weight of at least 2,500.

6. The fluorinated ether compound according to claim 1, wherein T is —Si(R)$_{3-c}$(L)$_c$, wherein R is an alkyl group, L is a hydrolyzable group or a hydroxy group, and the two or more L in T may be the same or different, and c is 2 or 3.

7. A fluorinated ether composition comprising at least one fluorinated ether compound as defined in claim 1, and at least one other fluorinated ether compound.

8. A coating liquid comprising the fluorinated ether composition as defined in claim 7, and a liquid medium.

9. A method for producing an article, which comprises applying the coating liquid as defined in claim 8 to a surface of a substrate by wet coating method, followed by drying to form a surface layer formed of the fluorinated ether composition on the surface of the substrate.

10. An article comprising a substrate and a surface layer formed of the fluorinated ether composition as defined in claim 7 on a surface of the substrate.

11. The article according to claim 10, which has the surface layer on a surface of a member constituting a plane of a touch panel to be touched with fingers.

12. A method for producing an article, which comprises treating a surface of a substrate by dry coating method using the fluorinated ether composition as defined in claim 7 to form a surface layer formed of the fluorinated ether composition on the surface of the substrate.

13. A coating liquid comprising the fluorinated ether compound as defined in claim 1, and a liquid medium.

14. A method for producing an article, which comprises applying the coating liquid as defined in claim 13 to a surface of a substrate by wet coating method, followed by drying to form a surface layer formed of the fluorinated ether compound on the surface of the substrate.

15. An article comprising a substrate and a surface layer formed of the fluorinated ether compound as defined in claim 1 on a surface of the substrate.

16. The article according to claim 15, which has the surface layer on a surface of a member constituting a plane of a touch panel to be touched with fingers.

17. A method for producing an article, which comprises treating a surface of a substrate by dry coating method using the fluorinated ether compound as defined in claim 1 to form a surface layer formed of the fluorinated ether compound on the surface of the substrate.

18. A fluorinated ether compound of formula (1B):

$$[T\text{-}]_{b2}Q^2\text{-}Q^f\text{-}Q^2[\text{-}T]_{b2} \quad (1B)$$

wherein $Q^f$ is a bivalent group both the bond terminals of which are constituted by a carbon atom, which comprises a first partial structure of formula (1) and a second partial structure of formula (2):

$$-OR^{f12}- \quad (1)$$

$$-OR^{f13}- \quad (2)$$

wherein $R^{f12}$ is a $C_{1-6}$ fluoroalkylene group, and $R^{f13}$ is a group having a fluorinated cyclic structure which may have a hetero atom;

and wherein $Q^f$ comprises at least five first partial structures or comprises at least two second partial structures, $Q^2$ is a b2+1 valent linking group, and the two $Q^2$ may be the same or different, T is —R$^{f6}$, —Ar, —OR$^{10}$, —SR$^{10}$, —NOR$^{10}$, —C(=O)R$^{10}$, —N(R$^{10}$)$_2$, —N$^+$(R$^{10}$)$_3$X$^3$, —C≡N, —C(=NR$^{10}$)—R$^{10}$, —N$^+$≡N, —N=NR$^{10}$, —C(=O)OR$^{10}$, —C(=O)OX$^2$, —C(=O)OX$^4$, —C(=O)OC(=O)R$^{10}$, —SO$_2$R$^{10}$, —SO$_3$H, —SO$_3$X$^2$, —O—P(=O)(—OR$^{10}$)$_2$, —O—P(=O)(—OR$^{10}$)(—OX$^2$), —N=C=O, —Si(R)$_{3-c}$(L)$_c$, —C(R$^{10}$)=C(R$^{10}$)$_2$, —C≡C(R$^{10}$), —C(=O)N(R$^{10}$)$_2$, —N(R$^{10}$)C(=O)R$^{10}$, —Si(R$^{10}$)$_2$—O—Si(R$^{10}$)$_3$, —NH—C(=O)R$^{10}$, —C(=O)NHR$^{10}$, —I, or a group containing

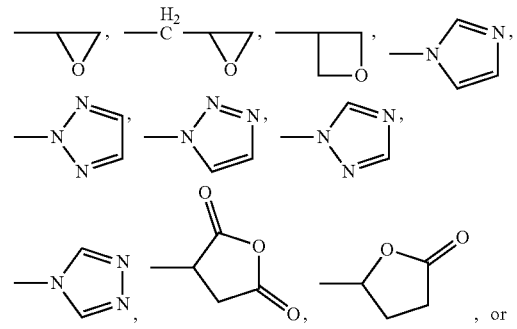

-continued

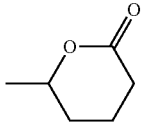

$R^{f6}$ is a $C_{1-6}$ fluoroalkyl group,
$R^{10}$ is a hydrogen atom, a $C_{1-6}$ alkyl or fluoroalkyl group, or an aryl group which may have a substituent, and when there are two or more $R^{10}$, the two or more $R^{10}$ may be the same or different,
Ar is an aryl group which may have a substituent,
$X^2$ is an alkali metal ion or an ammonium ion,
$X^3$ is a halide ion,
$X^4$ is a halogen atom,
R is an alkyl group,
L is a hydrolyzable group or a hydroxy group, and the two or more L in T may be the same or different,
b2 is an integer of at least 2, and the two b2 may be the same or different,
c is 2 or 3, and
the two or more T may be the same or different.

19. The fluorinated ether compound according to claim 18, wherein $Q^f$ is a group represented by the following formula (g1b):

wherein $R^{f2}$ is a $C_{1-6}$ fluoroalkylene group provided that to the carbon atom at the terminal on the $Q^2$ side of $R^{f2}$ bonded to $Q^2$, at least one fluorine atom is bonded,
$R^{f3}$ is a bivalent fluorinated hydrocarbon group having a fluorinated cyclic structure provided that to the carbon atom at the terminal on the $Q^2$ side of $R^{f3}$ bonded to $Q^2$, at least one fluorine atom is bonded,
$R^{f4}$ is a $C_{1-6}$ fluoroalkylene group or a bivalent fluorinated hydrocarbon group having a fluorinated cyclic structure provided that to the carbon atom at the terminal on the $Q^2$ side of $R^{f4}$, at least one fluorine atom is bonded,
n is an integer of from 0 to 500 when $R^{f4}$ has a fluorinated cyclic structure, or an integer of from 1 to 500 when $R^{f4}$ has no fluorinated cyclic structure, and when n is at least 2, $(OR^{f3})_n$ may consist of two or more types of $OR^{f3}$,
when n is 0, m is an integer of from 5 to 500, and
when n is at least 1, m is an integer of from 2 to 500,
provided that when m is at least 2, $(OR^{f2})_m$ may consist of two or more types of $OR^{f2}$, and
the bonding order of m $(OR^{f2})$ and n $(OR^{f3})$ is not limited.

20. The fluorinated ether compound according to claim 18, wherein $Q^2$ is a group represented by the formula (g2-1) provided that b2=d2+d4, a group represented by the formula (g2-2) provided that b2=e2, a group represented by the formula (g2-3) provided that b2=2, a group represented by the formula (g2-4) provided that b2=h2, a group represented by the formula (g2-5) provided that b2=i2, or a group represented by the formula (g2-7) provided that b2=i3:

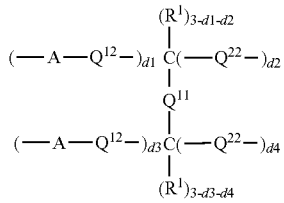

(g2-1)

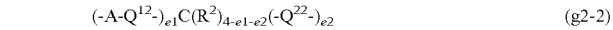  (g2-2)

  (g2-3)

  (g2-4)

  (g2-5)

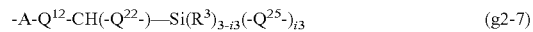  (g2-7)

wherein in the formulae (g2-1) to (g2-7), the A side is bonded to $Q^f$, and the $Q^{22}$, $Q^{23}$, $Q^{24}$, and $Q^{25}$ side is bonded to T,
A is a single bond, —C(O)NR$^6$—, —C(O)—, —OC(O)O—, —NHC(O)O—, —NHC(O)NR$^6$—, —O— or —SO$_2$NR$^6$—,
$Q^{11}$ is a single bond, —O—, an alkylene group or a group having —C(O)NR$^6$—, —C(O)—, —NR$^6$— or —O— between carbon atoms of an alkylene group having at least 2 carbon atoms,
$Q^{12}$ is a single bond, an alkylene group or a group having —C(O)NR$^6$—, —C(O)—, —NR$^6$— or —O— between carbon atoms of an alkylene group having at least 2 carbon atoms, and when $Q^2$ has two or more $Q^{12}$, the two or more $Q^{12}$ may be the same or different,
$Q^{13}$ is a single bond provided that A is —C(O)—, an alkylene group, a group having —C(O)NR$^6$—, —C(O)—, —NR$^6$— or —O— between carbon atoms of an alkylene group having at least 2 carbon atoms, or an alkylene group having —C(O)— at the terminal on the N side,
$Q^{14}$ is $Q^{12}$ when the atom in Z to which $Q^{14}$ is bonded is a carbon atom, or $Q^{13}$ when the atom in Z to which $Q^{14}$ is bonded is a nitrogen atom, and when $Q^2$ has two or more $Q^{14}$, the two or more $Q^{14}$ may be the same or different,
$Q^{15}$ is an alkylene group or a group having —C(O)NR$^6$—, —C(O)—, —NR$^6$— or —O— between carbon atoms of an alkylene group having at least 2 carbon atoms, and when $Q^2$ has two or more $Q^{15}$, the two or more $Q^{15}$ may be the same or different,
$Q^{22}$ is an alkylene group, a group having —C(O)NR$^6$—, —C(O)—, —NR$^6$— or —O— between carbon atoms of an alkylene group having at least 2 carbon atoms, an alkylene group having —C(O)NR$^6$—, —C(O)—, —NR$^6$— or —O— at the terminal on the side not bonded to T, or a group having —C(O)NR$^6$—, —C(O)—, —NR$^6$— or —O— between carbon atoms of an alkylene group having at least 2 carbon atoms and having —C(O)NR$^6$—, —C(O)—, —NR$^6$— or —O— at the terminal on the side not bonded to T, and when $Q^2$ has two or more $Q^{22}$, the two or more $Q^{22}$ may be the same or different,
$Q^{23}$ is an alkylene group or a group having —C(O)NR$^6$—, —C(O)—, —NR$^6$— or —O— between carbon atoms of an alkylene group having at least 2 carbon atoms, and the two $Q^{23}$ may be the same or different,
$Q^{24}$ is $Q^{22}$ when the atom in Z to which $Q^{24}$ is bonded is a carbon atom, or $Q^{23}$ when the atom in Z to which $Q^{24}$ is bonded is a nitrogen atom, and when $Q^2$ has two or more $Q^{24}$, the two or more $Q^{24}$ may be the same or different,
$Q^{25}$ is an alkylene group or a group having —C(O)NR$^6$—, —C(O)—, —NR$^6$— or —O— between carbon atoms of an alkylene group having at least 2 carbon atoms, and when $Q^2$ has two or more $Q^{25}$, the two or more $Q^{25}$ may be the same or different, Z is a group having a b2+1 valent cyclic structure having a carbon atom or a nitrogen atom to which $Q^{14}$ is directly bonded and having a carbon atom or a nitrogen atom to which $Q^{24}$ is directly bonded, $R^1$ is a hydrogen atom or an alkyl group, and when $Q^2$ has two or more $R^1$, the two or more $R^1$ may be the same or different, $R^2$ is a hydrogen atom, a hydroxy group, an alkyl group or an acyloxy group, $R^3$ is an alkyl group, $R^6$ is a hydrogen atom, a $C_{1-6}$ alkyl group or a phenyl group, d1 is an integer of from 0 to 3, d2 is an integer of from 0 to 3, and d1+d2 is an integer of from 1 to 3, d3 is an integer of from 0 to 3, d4 is an integer of from 0 to 3, and d3+d4 is an integer of from 1 to 3, d1+d3 is 1 in $Q^2$, d2+d4 is an integer of from 3 to 5 in $Q^2$, e1+e2 is 3 or 4, e1 is 1 in $Q^2$, e2 is 2 or 3 in $Q^2$, h1 is 1 in $Q^2$, h2 is an integer of at least 2, i1+i2 is 3 or 4, i1 is 1 in $Q^2$, i2 is 2 or 3 in $Q^2$, and i3 is 2 or 3.

21. The fluorinated ether compound according to claim 18, wherein the fluorinated cyclic structure is a four-membered ring.

22. The fluorinated ether compound according to claim 18, which has a number average molecular weight of at least 2,500.

23. A fluorinated ether composition comprising at least one fluorinated ether compound as defined in claim 18, and at least one other fluorinated ether compound.

24. A coating liquid comprising the fluorinated ether composition as defined in claim 23, and a liquid medium.

25. An article comprising a substrate and a surface layer formed of the fluorinated ether composition as defined in claim 23 on a surface of the substrate.

26. The article according to claim 25, which has the surface layer on a surface of a member constituting a plane of a touch panel to be touched with fingers.

27. A method for producing an article, which comprises treating a surface of a substrate by dry coating method using the fluorinated ether composition as defined in claim 23 to form a surface layer formed of the fluorinated ether composition on the surface of the substrate.

28. A coating liquid comprising the fluorinated ether compound as defined in claim 18, and a liquid medium.

29. A method for producing an article, which comprises applying the coating liquid as defined in claim 28 to a surface of a substrate by wet coating method, followed by drying to form a surface layer formed of the fluorinated ether compound on the surface of the substrate.

30. A method for producing an article, which comprises applying the coating liquid as defined in claim 28 to a surface of a substrate by wet coating method, followed by drying to form a surface layer formed of the fluorinated ether composition on the surface of the substrate.

31. An article comprising a substrate and a surface layer formed of the fluorinated ether compound as defined in claim 18 on a surface of the substrate.

32. The article according to claim 31, which has the surface layer on a surface of a member constituting a plane of a touch panel to be touched with fingers.

33. A method for producing an article, which comprises treating a surface of a substrate by dry coating method using the fluorinated ether compound as defined in claim 18 to form a surface layer formed of the fluorinated ether compound on the surface of the substrate.

* * * * *